(12) United States Patent
Morelli et al.

(10) Patent No.: US 11,225,481 B2
(45) Date of Patent: Jan. 18, 2022

(54) XANTHINE DERIVATIVE INHIBITORS OF BET PROTEINS

(71) Applicants: Centre national de la recherche scientifique, Paris (FR); INSTITUT NATIONAL DE LA SANTE ET DE LA RECHERCHE MEDICALE (INSERM), Paris (FR); Université d'Aix-Marseille, Marseilles (FR); Institut Jean Paoli & Irene Calmettes, Marseilles (FR)

(72) Inventors: Xavier Morelli, Marseilles (FR); Sébastien Combes, Marseilles (FR); Jean-Claude Guillemot, Marseilles (FR); Stéphanie Betzi, Marseilles (FR); Yves Collette, Marseilles (FR); Philippe Roche, Marseilles (FR); Adrien Lugari, Lyons (FR); Sabine Milhas, Pavie (FR); Brigitt Raux, Marseilles (FR); Iuliia Voitovich, Marseilles (FR)

(73) Assignees: CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITÉ D'AIX-MARSEILLE, Marseilles (FR); INSTITUT JEAN PAOLI & IRENE CALMETTES, Marseilles (FR)

( * ) Notice: Subject to any disclaimer, the term of this patent is extended or adjusted under 35 U.S.C. 154(b) by 1 day.

(21) Appl. No.: 16/067,471

(22) PCT Filed: Dec. 27, 2016

(86) PCT No.: PCT/EP2016/082731
§ 371 (c)(1),
(2) Date: Jun. 29, 2018

(87) PCT Pub. No.: WO2017/114843
PCT Pub. Date: Jul. 6, 2017

(65) Prior Publication Data
US 2019/0292186 A1 Sep. 26, 2019

(30) Foreign Application Priority Data

Dec. 29, 2015 (EP) .................................... 15307163

(51) Int. Cl.
*C07D 519/00* (2006.01)
*C07D 473/04* (2006.01)
*A61P 35/02* (2006.01)
*C07D 473/06* (2006.01)

(52) U.S. Cl.
CPC ............ *C07D 473/04* (2013.01); *A61P 35/02* (2018.01); *C07D 473/06* (2013.01); *C07D 519/00* (2013.01)

(58) Field of Classification Search
CPC .. C07D 473/06; C07D 519/00; C07D 473/10; C07D 473/16; C07D 473/18; C07D 473/20; C07D 473/22; C07D 473/24; A61K 31/522; A61P 35/02
USPC ............... 544/267, 260, 266, 269, 268, 270; 514/263.1, 263.2, 263.35
See application file for complete search history.

(56) References Cited

U.S. PATENT DOCUMENTS

| | | | |
|---|---|---|---|
| 4,289,776 A | * | 9/1981 | Mohler ..................... A61P 9/08 514/263.36 |
| 4,871,194 A | | 10/1989 | Kawashima et al. |
| 4,942,143 A | * | 7/1990 | Ohsaki ...................... A61P 9/08 514/222.8 |
| 7,906,520 B2 | | 3/2011 | Woolf et al. |
| 9,925,197 B2 | | 3/2018 | Albrecht et al. |
| 2005/0197341 A1 | | 9/2005 | Woolf et al. |
| 2011/0207753 A1 | | 8/2011 | Woolf et al. |
| 2013/0210826 A1 | | 8/2013 | Woolf et al. |
| 2014/0296243 A1 | | 10/2014 | Albrech et al. |
| 2014/0296246 A1 | | 10/2014 | Aktoudianakis et al. |
| 2015/0148344 A1 | | 5/2015 | Babaoglu et al. |

(Continued)

FOREIGN PATENT DOCUMENTS

| WO | WO-2015080707 | 6/2015 | |
|---|---|---|---|
| WO | WO2016115360 | * 7/2016 | ......... A61K 31/4245 |

(Continued)

OTHER PUBLICATIONS

Simcic et al. Si 24117; CA 167:326508,2014. CAPLUS Abstract provided.*

(Continued)

*Primary Examiner* — Jeffrey H Murray
(74) *Attorney, Agent, or Firm* — B. Aaron Schulman, Esq.; Stites & Harbison, PLLC

(57) ABSTRACT

This invention relates to xanthine derivative compounds that are inhibitors of BET bromodomains proteins, the method of preparation thereof and applications thereof.

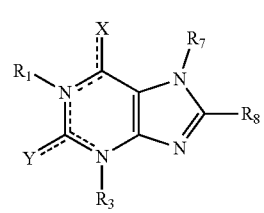

(I)

18 Claims, 1 Drawing Sheet

(56) References Cited

U.S. PATENT DOCUMENTS

2017/0143724 A1 5/2017 Grases Freixedas et al.
2017/0166569 A1 6/2017 Ye et al.

FOREIGN PATENT DOCUMENTS

WO WO-2017021435 A1 * 2/2017 ........... A61K 31/522
WO WO-2017114843 7/2017

OTHER PUBLICATIONS

Aleksandrova et al. Ukrainskii Khimicheskii Zhurnal(Russian Edition) 79(5), 67-73, 2013; CA 159:698600, 2013. CAPLUS Abstract provided.*
Eckstein et al. Pharmazeutische Zentralhalle fuer Deutschland 102( )6, 367-71, 1963;; CA 62: 82548, 1965. CAPLUS Abstract provided.*
Gui et al. J. Am. Chem. Soc. 2014, 136(13), 4853-4856.*
Aninye et.al, Steroids 77, 596-601,2012.*
Dietz et al. Journal of Medicinal Chemistry, 1966, 9(4), 500-506.*
Onodera et al. J. Chem. Inf. Model.,., 2007, 47(4), 1609-1618.*
Andrieu et al. Drug Discovery Today: Technologies, vol. 19, 45-50, 2016.*
Freshney et al.,Culture of Animal Cells, A Manual of Basic Technique, Alan R. Liss, Inc., 1983, New York, p. 4.*
Dermer et al., Bio/Technology, 1994, 12:320.*
Cecil Textbook of Medicine, edited by Bennet, J.C., and Plum F., 20th edition,vol. 1, 1004-101 O, 1996.*
Golub et al., Science, 286, 531-537, 1999.*
PubChem Search Results—pccompound 1-23, Create Date Sep. 16, 2004 through Create Date Dec. 1, 2012. PubChem Search Results provided.*
Michael, et al, "Alkylpurines as Immunepotentiating Agents. Synthesis and Antiviral Activity Certain Alkylguanines", 1993, pp. 3431-3436, vol. 36, J. Med. Chem.
Zhang, et al, "Discovery of Novel Vascular Endothelial Growth Factor Receptor 2 Inhibitors: A Virtual Screening Approach", 2012, pp. 893-901, vol. 80, Chem Biol Drug Des.
Yun, et al, "The identification, analysis and structure-based development of novel inhibitors of 6-hydroxymethyl-7,8-dihydropterin pyrophosphokinase", 2014, pp. 2157-2165, vol. 22, Bioorg. Med. Chem.
International Search Report for PCT/EP2016/082731, completed Feb. 8, 2017.
Written Opinion of the International Searching Authority for PCT/EP2016/082731, completed Feb. 8, 2017.
Sakai R et al: "Effects of Alkyl Substitutions of Xanthine Skeleton on Bronchodilation", Journal of Medicinal Chemistry, American Chemical Society, US, vol. 35, Jan. 1, 1992(Jan. 1, 1992), pp. 4039-4044, XP000918836, ISSN: 0022-2623, DOI: 10.1021/JM00100A008 tables I, II; compounds 1,6,11,13,18,20,25,27,29.
E. A. Rogozin et al: "Inhibitory effects of caffeine analogues on neoplastic transformation: structure-activity relationship", Carcinogenesis., vol. 29, No. 6, Apr. 15, 2008(Apr. 15, 2008), pp. 1228-1234, XP055230059, GB ISSN: 0143-3334, DOI: 10.1093/carcin/bgn016 tables I,II; compounds 1,3,4,7,10,14,16,20,24,28,44.
Sarah Picaud et al: "9 H-Purine Scaffold Reveals Induced-Fit Pocket Plasticity of the BRD9 Bromodomain", Journal of Medicinal Chemistry, vol. 58, No. 6,Mar. 26, 2015(Mar. 26, 2015), pp. 2718-2736, XP055266266, US ISSN: 0022-2623, DOI: 10.1021/jm501893k Chart 2; figure 1.

* cited by examiner

XANTHINE DERIVATIVE INHIBITORS OF BET PROTEINS

INTRODUCTION

This invention relates to xanthine derivative compounds that are inhibitors of BET bromodomains proteins, the method of preparation thereof and applications thereof.

BACKGROUND OF THE INVENTION

Bromodomains (BRD) are protein domains called protein interaction modules that preferentially bind ε-N-acetylated lysine residues through structurally well-defined pockets. BRDs are found in 8 protein families which include a total of 46 nuclear or cytoplasmic proteins in human with diverse structures and functions, including chromatin-modifying enzymes, helicases, chromatin remodelers, transcriptional co-activators and mediators, and the bromodomain and extra-terminal domain (BET) family of proteins.[1-3] BET proteins (BRD2, BRD3, BRD4, and the testis-specific BRDT) have a conserved modular architecture including two N-terminal tandem BRDs (BD1 and BD2). The BETs play a central role in chromatin biology by acting as tissue-specific recruitment platforms that tether complexes to acetylated histones and chromatin, facilitating the assembly of the transcriptional machinery and controlling gene expression in inflammation, viral infection and cancer biology. For example, BRD2 is specifically recruited to acetylated histones H3 and H4 and this interaction is linked to active transcription and mitosis.[4,5] BRD2 and BRD3 are required for permissive RNA polymerase II transcription through acetylated nucleosomes[6] and it has been suggested that BRD4 binds acetylated histones using primarily its first bromodomain (BD1).[7,8] The BD2 domain also recognizes and interacts with the acetylated region of cyclin Ti which forms a complex with the positive transcription elongation factor b and is crucial for the sustained presence of Pol II in active genes and for transcription initiation and elongation,[9] thereby regulating the expression of cell proliferation supporting genes, including c-Myc and its target genes.[10]

BET proteins are often deregulated in diseases, their transcription-regulating activity being altered and thus affecting numerous growth-promoting genes and cytokines. BET proteins are known to be deregulated in cancer[11] and the recent disclosure of pan-BET inhibitors (multi-targeted BET inhibitors) that attenuate BRD function has allowed the validation of these drug targets, shedding light on their roles in such diseases. Interestingly, BRD4 occupies "super-enhancers" and its inhibition leads to significant reduction of the transcript levels of only a few hundred genes,[12] in a cell-, disease- and context-specific manner. Alongside, preclinical targeting of BETs has had initial successes, particularly in oncology. For example, in a phase I acute leukemia study, (6S)-4-(4-chlorophenyl)-N-(4-hydroxyphenyl)-2,3,9-trimethyl-6H-thieno[3,2-f][1,2,4]triazolo[4,3-a][1,4]diazepine-6-acetamide (OTX015),[13-16] a thienodiazepine, induced remissions, including complete remission in two patients with refractory disease, and 2-[4-(2-hydroxyethoxy)-3,5-dimethylphenyl]-5,7-dimethoxy-4(3H)-quinazolinone (RVX-208),[8,17] a quinazolone derivative of resveratrol that binds preferentially to the BD2 domain of BRD2 and BRD3 has already been tested in hundreds of patients in phase II clinical trials for the treatment of atherosclerosis, providing proof-of-concept that selective inhibition within the BET family is feasible.

A permanent wavering in drug discovery is related to the development of pan- or selective (single targeted-) inhibitor. Indeed, pan-BET inhibition might remain an issue regarding the impact on numerous transcriptional pathways and the individual tissue specific functions of BET members. However, there are potential drawbacks concerning the use of pan-BET inhibitors with strong risks of 'off-target' effects and/or appearance of resistances.

Therefore, the selective targeting of individual BET and the discrimination between BD1 and BD2 present an opportunity to achieve more selective transcriptional effects.

In the absence of selective probes dedicated to single bromodomains it is still not clear which BET should be the main target of pharmaceutical (worldwide) efforts. The current challenge thus still lies in the identification of bromodomains BRD(Xi) selective inhibitors.

The Inventors investigated the key structural feature responsible for the selectivity of a xanthine-based (BET) family inhibitor identified through a mid-throughput screening (MTS).

They have now found xanthine derivatives that are highly selective bromodomains inhibitors. Those compounds bind with an affinity in the low micromolar range, yet exert suitable unexpected selectivity in vitro, against the other members of the bromodomains and extra-terminal domains (BET) family. They also pinpointed the specific structural elements of BET protein having a key role in the selectivity. In particular they found that specific substituents on xanthine derivative compounds allow fine-tuning the selectivity of the xanthine compounds among the BET proteins.

Thus, the xanthine derivative compounds according to the present invention are interesting because they are used as selective inhibitors and as pan-BET inhibitors.

Moreover, the generation of such probes allows an evaluation of the biological role for each bromodomain and comforts the growing interest of the development of selective vs pan-BET inhibitors for the clinic trials of related-diseases-treatments.

SUMMARY OF THE INVENTION

The present invention relates to a BET protein inhibitor which is a xanthine derivative compound of general formula (I)

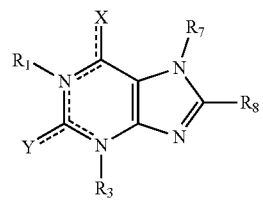

Formula (I)

wherein,

X is an oxygen atom, —$OR_a$, a sulphur atom, —$SR_b$, a nitrogen atom, —$NR_c$, or —$NR_cR_d$;

wherein $R_a$, $R_b$, Re and $R_d$ each independently represent:
- a hydrogen atom,
- a $C_1$-$C_6$ alkyl, optionally substituted,
- a ($C_5$-$C_{12}$)aryl-($C_1$-$C_6$)alkyl, said aryl being optionally substituted, or
- a ($C_1$-$C_6$)alkyl-($C_5$-$C_{12}$)aryl, optionally substituted;

Y is a nitrogen atom, —$NR_eR_f$, an oxygen atom, $OR_g$ or a linker-ligand for the E3 ubiquitin ligase;
    wherein $R_e$, $R_f$ and $R_g$ each independently represent:
        a hydrogen atom,
        a $C_1$-$C_6$ alkyl, optionally substituted,
        a $C_5$-$C_{12}$ aryl, optionally substituted,
        a ($C_5$-$C_{12}$)aryl-($C_1$-$C_6$)alkyl, said aryl being optionally substituted,
        a ($C_1$-$C_6$)alkyl-($C_5$-$C_{12}$)aryl, optionally substituted,
        —C(O)$OR_h$, or
        —C(O)$R_h$;
$R_1$ represents a hydrogen atom or a lone pair;
$R_3$ represents:
    a lone pair,
    a hydrogen atom,
    a $C_1$-$C_6$ alkyl, optionally substituted,
    a $C_5$-$C_{12}$ aryl, optionally substituted,
    a ($C_5$-$C_{12}$)aryl-($C_1$-$C_6$)alkyl, said aryl being optionally substituted,
    a ($C_1$-$C_6$)alkyl-($C_5$-$C_{12}$)aryl, optionally substituted,
    —C(O)$OR_i$,
    —C(O)$R_i$, or
    a linker-ligand for the E3 ubiquitin ligase;
$R_7$ represents:
    a lone pair,
    a hydrogen atom,
    a $C_1$-$C_6$ alkyl, optionally substituted,
    a $C_5$-$C_{12}$ aryl, optionally substituted,
    a ($C_5$-$C_{12}$)aryl-($C_1$-$C_6$)alkyl, said aryl being optionally substituted,
    a ($C_1$-$C_6$)alkyl-($C_5$-$C_{12}$)aryl, optionally substituted,
    —C(O)$OR_j$, or
    —C(O)$R_j$;
wherein $R_h$, $R_i$ and $R_j$ each independently represent a hydrogen atom, a $C_1$-$C_6$ alkyl optionally substituted, a $C_5$-$C_{12}$ aryl optionally substituted, a ($C_5$-$C_{12}$)aryl-($C_1$-$C_6$)alkyl optionally substituted, a ($C_1$-$C_6$)alkyl-($C_5$-$C_{12}$)aryl optionally substituted, a heteroaryl optionally substituted, an alkylheteroaryl optionally substituted, a heteroarylalkyl optionally substituted;
    $R_8$ is a hydrogen atom, a halogen atom, a $C_1$-$C_6$ alkyl optionally substituted, a linker-ligand for the E3 ubiquitin ligase or -A-B;
        wherein A represents —($CH_2$)$_n$, a sulphur atom, —$SO_2$—, —$CH_2$—O—, —$CH_2$—S—, —$CH_2$—$SO_2$—, an oxygen atom, or —N(H)—;
        wherein B represents:
            a hydrogen atom,
            —OH,
            a halogen atom,
            —SH,
            —$CO_2$H,
            a $C_1$-$C_6$ alkyl, optionally substituted,
            a ($C_5$-$C_{12}$)aryl-($C_1$-$C_6$)alkyl, optionally substituted,
            a ($C_1$-$C_6$)alkyl-($C_5$-$C_{12}$)aryl, optionally substituted,
            a $C_5$-$C_{12}$ aryl, optionally substituted by one or more:
                $C_1$-$C_6$ alkyl groups,
                oxygen atoms,
                sulphur atoms,
                halogen atoms, —amino groups,
                —($C_1$-$C_4$)alkanoic acid,
                —S($O_2$)—($C_1$-$C_4$)alkyl,
                —S($O_2$)-piperidine,
                —S($O_2$)—(N,N)dimethylamine,
                —S($O_2$)-morpholine,
                nitro groups,
                —C(═O)—O—($C_1$-$C_4$)alkyl,
                —S(O2)-N(H)—($C_1$-$C_4$)alkyl,
                oxo-pyrazole optionally substituted by one or more ($C_1$-$C_4$)alkanoic acid, ($C_1$-$C_4$)alkyl, halogen atoms or —OH,
                ketone groups,
                pyrazole optionally substituted by one or more ($C_1$-$C_4$)alkanoic acid, ($C_1$-$C_4$)alkyl, halogen atoms or —OH,
                pyrrolidine optionally substituted by one or more ($C_1$-$C_4$)alkanoic acid, ($C_1$-$C_4$)alkyl, halogen atoms or —OH,
                phenyl,
                benzyl,
                oxy-phenyl,
                oxy-benzyl,
                thiazolidin optionally substituted by one or more ($C_1$-$C_4$)alkanoic acid, ($C_1$-$C_4$)alkyl, halogen atoms or —OH,
                —C(═O)—N(H)-benzyl,
                —N(H)-quinazolinone,
                —OH,
                thiophenyl optionally substituted by one or more ($C_1$-$C_4$)alkanoic acid, ($C_1$-$C_4$)alkyl, halogen atoms or —OH,
                methyl-tetrahydrofuran, or
                —$CH_2$-pyrazole optionally substituted by one or more ($C_1$-$C_4$)alkanoic acid, ($C_1$-$C_4$)alkyl, halogen atoms or —OH;
    a ($C_1$-$C_6$)alkyl-heteroaryl, optionally substituted;
    a heteroaryl-($C_1$-$C_6$)alkyl, optionally substituted;
    a heteroaryl, optionally substituted by one or more:
        $C_1$-$C_6$ alkyl groups,
        halogen atoms,
        oxygen atoms,
        sulphur atoms,
        amino groups,
        —($C_1$-$C_4$)alkanoic acid,
        —S($O_2$)—($C_1$-$C_4$)alkyl,
        —S($O_2$)-piperidine,
        —S($O_2$)—(N,N)dimethylamine,
        —S($O_2$)-morpholine,
        nitro groups,
        —C(═O)—O—($C_1$-$C_4$)alkyl,
        —S($O_2$)—N(H)—($C_1$-$C_4$)alkyl,
        oxo-pyrazole optionally substituted by one or more ($C_1$-$C_4$)alkanoic acid, ($C_1$-$C_4$)alkyl, halogen atoms or —OH,
        ketone groups,
        pyrazole optionally substituted by one or more ($C_1$-$C_4$)alkanoic acid, ($C_1$-$C_4$)alkyl, halogen atoms or —OH,
        pyrrolidine optionally substituted by one or more ($C_1$-$C_4$)alkanoic acid, ($C_1$-$C_4$)alkyl, halogen atoms or —OH,
        phenyl,
        benzyl,
        oxy-phenyl,
        oxy-benzyl,
        thiazolidin optionally substituted by one or more ($C_1$-$C_4$)alkanoic acid, ($C_1$-$C_4$)alkyl, halogen atoms or —OH,
        —C(═O)—N(H)-benzyl,
        —N(H)-quinazolinone,
        —OH, thiophenyl optionally substituted by one or more $(C_1-C_4)$alkanoic acid, $(C_1-C_4)$alkyl, halogen atoms or —OH, methyl-tetrahydrofuran, or —$CH_2$-pyrazole optionally substituted by one or more $(C_1-C_4)$alkanoic acid, $(C_1-C_4)$alkyl, halogen atoms or —OH;

wherein n represents an integer ranging from 0 to 1, 2, 3, 4, 5, 6, 7, 8, 9 or 10;

or $R_7$ with $R_8$ taken together form a cycle by forming a covalent bond between a $R_7$ group and $R_8$ group as defined above;

or a pharmaceutically acceptable salt thereof and/or tautomeric form thereof.

DEFINITIONS

The term "BET protein" or "BET family member" in the present invention refers to a BET protein chosen from the group consisting of: BRD2, BRD3, BRD4 and BRDT.[1-3]

The term "bromodomain" in the present invention refers to the bromodomain BD1 or BD2 of a BET protein.[1-3]

The term "BET protein inhibitor" in the present invention refers to a compound that binds to the target BET protein, in particular binds to the target bromodomain (BD1 or BD2) of a BET protein with measurable affinity, and decreases its activity. Typically, according to the invention, an inhibitor binds to a BET protein and in particular to a bromodomain of a BET protein, thus decreasing the activity of the BET protein. Other kinds of inhibitors provided with a ligand for the E3 ubiquitin ligase, once linked to their target, i.e. a BET protein and in particular a bromodomain of a BET protein, will lead to the degradation of the corresponding BET protein.

By the term "decrease its activity" herein, it is understood that a BET protein, and in a particular a bromodomain of a BET protein, bound to an inhibitor of the present invention has a lower activity than the same BET protein non-bound to said inhibitor.

The BET protein's and in more particularly the bromodomain of the BET protein's "activity" or "biological function" is well-known from the prior art and corresponds to an activity involving tissue-specific recruitment platforms that tether complexes to acetylated histones and chromatin, facilitating the assembly of the transcriptional machinery and controlling gene expression.[1-3]

The term "$IC_{50}$" in the present invention refers to the half maximal inhibitory concentration which is a measure of the effectiveness of a compound in inhibiting biological function, e.g. inhibition of protein-protein interaction. Typically $IC_{50}$ is measured by homogeneous time resolved fluorescence (HTRF). In the present invention, $IC_{50}$ is determined for a specific BET protein.

The term "Kd" in the present invention refers to the equilibrium dissociation constant which is a measure of the strength of interactions between said BET protein, particularly the bromodomain of said BET protein, and the corresponding inhibitor. Typically, Kd is measured by Isothermal Titration Calorimetry (ITC).

The term "ligand efficiency" (LE) in the present invention refers to the ratio of the log of the $IC_{50}$ to the number (N) of non-hydrogen atoms of the compound, i.e. $LE=1.4*(-\log(IC_{50})/N)$.

By the term "the inhibitor inhibits selectively BRD4 (BD1)" in the present invention, it is understood that said inhibitor has an $IC_{50}$ for BRD4 (BD1) five times lower, preferably 10 times lower, than the $IC_{50}$ of the same inhibitor tested on at least one, preferably at least two, three, four, five, six or seven of the other bromodomains of BET proteins selected from the group consisting of BRD3 (BD1), BRD2 (BD1), BRDT (BD1), BRD4 (BD2), BRD3 (BD2), BRD2 (BD2) and BRDT (BD2). Most preferably, said inhibitor has an $IC_{50}$ for BRD4 (BD1) five times lower, preferably 10 times lower, than the $IC_{50}$ of the same inhibitor tested on BRD3 (BD1), BRD2 (BD1), BRDT (BD1), BRD4 (BD2), BRD3 (BD2) and BRD2 (BD2).

The term "pharmaceutical composition" in the present invention refers to any composition comprising an effective amount of the inhibitor of the invention and at least one pharmaceutically acceptable carrier or excipient.

By the term "pharmaceutically acceptable carrier or excipient" herein, it is understood a carrier medium which does not interfere with the effectiveness of the biological activity of the active ingredient(s) and which is not excessively toxic to the host at the concentration at which it is administered. The term includes solvents, dispersion, media, coatings, isotonic agents, and adsorption delaying agents, and the like. Said carriers and excipients are selected, depending on the pharmaceutical form and the desired method of administration, from the usual excipients known by a person skilled in the art. Furthermore, the composition may comprise antibacterial and antifungal agents.

By the term "effective amount" herein, it is understood any amount of an inhibitor that is sufficient to fulfil its intended purpose(s), e.g., a desired biological or medicinal response in a cell, tissue, system or patient.

The term "pharmaceutically acceptable salt" in the present invention means that all pharmaceutically acceptable salts of the inhibitor according to the invention are included within the scope of the invention, in particular the salts of weak acids and of weak bases. Examples of salts include hydrochloride, hydrobromide, potassium acetate, sodium acetate, calcium acetate, ammonium chloride, potassium carbonate, sodium carbonate, calcium carbonate, potassium bicarbonate, sodium bicarbonate, and calcium bicarbonate.

The term "tautomeric forms" in the present invention refers to tautomers of nucleobases, i.e. constitutional isomers of nucleobases.

The term "treatment" in the present invention is used herein to characterize a method or process that is aimed at (1) slowing down or stopping the progression, aggravation, or deterioration of the symptoms of the disease; (2) bringing about amelioration of the symptoms of the disease; or (3) curing the disease. A treatment may thus be administered after initiation of the disease, for a therapeutic action.

The term "patient" in the present invention refers to a human or another mammal (e.g., primate, mouse, rat, rabbit, dog, cat, horse, cow, pig, camel, and the like). Preferably, the patient is a human.

The term "E3 ubiquitin ligase" is well known from a person skilled in the art (see Christopher E Berndsen et al., New insights into ubiquitin E3 ligase mechanism, 2014, Vol 21, Pages 301-307). The term "ligand for the E3 ubiquitin ligase" in the present invention, refers to PROTACs structures[34-36], preferably cereblon ligand or VHL ligand as defined below:

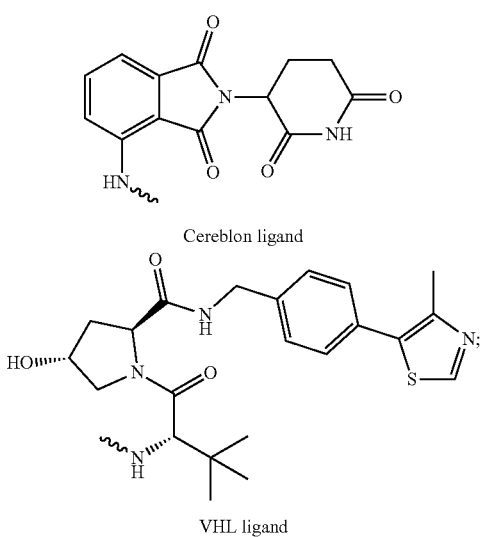

Cereblon ligand

VHL ligand said ligand being linked to the xanthine compound via a linker. The person skilled in the art will be able to choose the ligand position according to synthesis methods and constraints of the inhibitory activity.

By the term "linker" in the present invention, it is understood a molecular fragment that links the ligand for the E3 ubiquitin ligase as defined above to the xanthine compound, i.e. the rest of the inhibitor. Advantageously, the linker spaces the ligand for the E3 ubiquitin ligase from the xanthine compound and thus reduces the steric effects between the ligand and the xanthine compound. The linker consists of at least two atoms that can be the same or different. Advantageously the linker contains between 1-50 atoms in total, preferably between 1-30 atoms in total. An example of such linker is a hydrocarbon chain comprising one or more groups selected from: $C_1$-$C_6$ alkyl, $C_5$-$C_{12}$ aryl, ($C_5$-$C_{12}$ aryl)-($C_1$-$C_6$ alkyl), ($C_1$-$C_6$ alkyl)-($C_5$-$C_{12}$ aryl) said groups being optionally substituted with one or more hydrogen atoms or by one or more $C_1$-$C_4$ alkyl; it can also be amino acids, a polypeptide chain, or a polyethylene glycol. Preferably the linker is a polypeptide chain or a polyethylene glycol. By the term "linker-ligand for the E3 ubiquitin ligase" in the present invention, it is understood that the ligand for the E3 ubiquitin ligase is linked to the molecule through the linker as defined above.

The term "alkyl group" in the present invention means a linear or cyclic saturated aliphatic group with 1 to 6 carbon atoms, if it is not otherwise specified. The expression "$C_1$-$C_6$ alkyl" represents an alkyl having 1 to 6 carbons atoms. Examples of such alkyl groups include methyl, ethyl, n-propyl, i-propyl, n-butyl, i-butyl, s-butyl, t-butyl, n-pentyl, n-hexyl, cyclopropyl, cyclobutyl, cyclopentyl and cyclohexyl. Preferred alkyls are $C_1$-$C_4$ alkyl, such as methyl, ethyl, butyl, propyl, t-butyl, i-butyl and i-propyl.

The term "aryl group" in the present invention means a cyclic (mono- or polycyclic) aromatic group optionally substituted comprising 5 to 12 carbon atoms, if it is not otherwise specified. Examples of such aryl groups include phenyl, naphthyl and biphenyl. A preferred aryl is phenyl.

The term "arylalkyl" in the present invention means an aryl group as defined above, linked to the molecule through an alkyl group as defined above.

By the term "($C_5$-$C_{12}$)aryl-($C_1$-$C_6$)alkyl optionally substituted" in the present invention, it is understood that both aryl and alkyl can be substituted. Preferably, the aryl can be substituted.

The term "alkylaryl" in the present invention means an alkyl group as defined above, linked to the molecule through an aryl group as defined above.

By the term "($C_1$-$C_6$)alkyl-($C_5$-$C_{12}$)aryl optionally substituted" in the present invention, it is understood that both alkyl and aryl can be substituted.

The term "heteroaryl group" in the present invention means a cyclic (mono- or polycylic) aromatic group comprising 5 to 20 carbon atoms disposed in a ring, preferably from 4 to 19 carbon atoms and at least one heteroatom, preferably between 1 and 3 heteroatoms, such as nitrogen, oxygen or sulphur atoms. Examples of such heteroaryl groups include triazolyl, benzimidazolyl, indolyl, 1,2,4-triazolo[1,5-a]pyrimidinyl, tetrazolyl, furyl, thienyl, pyrrolyl, pyrazoyl, pyrazolyl, imidazolyl, thiazolyl, thiazoyl, oxazolyl, 1-benzofuryl, 1-benzothienyl, indanyl, indazolyl, benzoimidazolyl, benzisoxazolyl, benzisothiazolyl, benzothiazolyl, benzoxazolyl, benzotriazolyl, pyridyl, quinolinyl, pyridazinyl, cinnolinyl, phthalazinyl, pyrimidinyl, quinazolinyl, pyrazinyl, quinoxalinyl, pyridinyl, thiophenyl, dihydrobenzofuranyl, imidazo[1,2-a]pyridinyl, triazinyl, 1,2,4-triazinyl, chromenylium, phenyl, benzyl, [1,3]oxazolo[4,5-b]pyridinyl, pyrido-pyrimidinyl, pyridinyl, imidazo[4,5-b]pyridinyl, benzopyranonyl, pyrimidino-pyridinyl and pyridazino-cyclohexyl. Preferred heteroaryls are triazolyl, benzimidazolyl, indolyl, and 1,2,4-triazolo[1,5-a]pyrimidinyl, imidazo[1,2-a]pyridinyl, benzoxazolyl, pyridazinyl, triazinyl, 1,2,4-triazinyl, phenyl, benzyl, [1,3]oxazolo[4,5-b]pyridinyl, pyrido-pyrimidinyl, pyridinyl, imidazo[4,5-b]pyridinyl, benzopyranonyl, pyrimidino-pyridinyl and pyridazino-cyclohexyl.

The term "heteroarylalkyl" in the present invention means a heteroaryl group as defined above linked to the molecule through an alkyl group as defined above.

By the term "heteroaryl-($C_1$-$C_6$)alkyl optionally substituted" in the present invention, it is understood that both heteroaryl and alkyl can be substituted. Preferably, the heteroaryl can be substituted.

The term "alkylheteroaryl" in the present invention means an alkyl group as defined above linked to the molecule through a heteroaryl group as defined above.

By the term "($C_1$-$C_6$)alkyl-heteroaryl optionally substituted" in the present invention, it is understood that both alkyl and heteroaryl can be substituted.

The term "halogen atom" in the present invention means: fluorine, chlorine, bromine or iodine atoms, preferably chlorine or bromine atoms.

The term "substituted" in the present invention means that at least one of the hydrogen atom(s) of said group or radical is replaced with at least one substituent other than H. In the context of the present invention, and unless otherwise specified, the term "substituted" means for example halogen atoms as defined above, oxygen atoms such as =O, or sulphur atoms and groups as defined presently selected from a $C_1$-$C_6$ alkyl, cycloalkyl, haloalkyl, alkoxy, haloalkoxy, alkoxycarbonyl, aryl, aryloxy, arylalkyl, alkylaryl, heteroaryl, alkylheteroaryl, heteroarylalkyl, cyano, nitro, nitrile, amino, alkylamino, dialkylamino, arylamino, diarylamino, thioether, —SH, alkylthio, arylthio, hydroxyl group, carboxylic group, sulfonic group, ester group, carbonyl group, ether group, ketone group, —CHOH and —COH. Preferably the substituents are fluorine, chlorine, bromine, methyl, ethyl, butyl, propyl, t-butyl, i-butyl, i-propyl, oxygen atoms, sulphur atoms, nitro, hydroxyl group, carboxylic group, ester group, carbonyl group, ether group, ketone group and amino groups.

The term "cycloalkyl" in the present invention means a cyclic alkyl group, optionally substituted, comprising from 3 to 10 carbon atoms. Examples of such cycloalkyl groups include cyclopropyl, cyclobutyl, cyclopentyl, cyclohexyl and methylcyclohexyl.

The term "haloalkyl" in the present invention means any $C_1$-$C_6$ alkyl group as defined above substituted by one or more halogen atoms as defined above.

The term "alkoxy" in the present invention means a $C_1$-$C_6$ alkyl group as defined above linked to an oxygen atom. Examples of such alkoxy groups include methoxy, ethoxy, n-propoxy, i-propoxy, n-butoxy, i-butoxy, s-butoxy, t-butoxy, n-pentoxy and n-hexoxy.

The term "haloalkoxy" in the present invention means a group of formula —$OR_{a1}$ wherein $R_{a1}$ is a $C_1$-$C_6$ haloalkyl as defined above.

The term "alkoxycarbonyl" in the present invention means a group of formula —$C(O)OR_{b1}$ wherein $R_{b1}$ is a $C_1$-$C_6$ alkyl as defined above The term "aryloxy" in the present invention means an aryl group as defined above directly linked to an oxygen atom. An example of aryloxy group is phenyloxy.

The term "amino" in the present invention means a —NH2 group.

The term "alkylamino" in the present invention means an amino group as defined above wherein a hydrogen atom has been replaced with an alkyl group as defined above.

The term "dialkylamino" in the present invention means an amino group as defined above wherein each hydrogen atom has been replaced with an alkyl group as defined above.

The term "arylamino" in the present invention means an amino group as defined above wherein a hydrogen atom has been replaced with an aryl group as defined above.

The term "diarylamino" in the present invention means an amino group as defined above wherein each hydrogen atom has been replaced with an aryl group as defined above.

The term "thioether" in the present invention means —S-alkyl group or —S-aryl group wherein the terms alkyl and aryl are as defined above. Examples of such thioether groups include thiomethyl and thiophenyl.

The term "alkylthio" in the present invention means a —S-alkyl group.

The term "arylthio" in the present invention means a —S-aryl group.

The term "carboxylic group" in the present invention means a group of general formula —$COOR_{c1}$ wherein $R_{c1}$ is a hydrogen atom, a metallic cation or an alkyl group as defined above.

The term "sulfonic group" in the present invention means a group of general formula —$S(=O)_2OR_{d1}$ wherein $R_{d1}$ is a hydrogen atom, a metallic cation or an alkyl group as defined above.

The term "lone pair" in the present invention refers either to a lone pair of electrons which is not part of the aromatic ring or to a lone pair of electrons of the nitrogen atom which is delocalized and contributes to the aromatic pi electron system.

When the suffixe "ene" is used in conjunction with an alkyl, aryl or heteroaryl group, this means that the alkyl, aryl or heteroaryl group defined above is a divalent radical, i.e. it has two points of attachment to other groups.

DETAILED DESCRIPTION OF THE PREFERRED EMBODIMENTS

Products
Pan-BET Inhibitors

The present invention relates to a BET protein inhibitor which is a xanthine derivative compound of general formula (I)

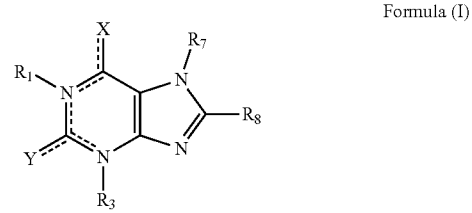

Formula (I)

wherein,
X is an oxygen atom, —$OR_a$, a sulphur atom, —$SR_b$, a nitrogen atom, —$NR_c$, or —$NR_cR_d$;
wherein $R_a$, $R_b$, $R_c$ and $R_d$ each independently represent:
a hydrogen atom,
a $C_1$-$C_6$ alkyl, optionally substituted,
a ($C_5$-$C_{12}$)aryl-($C_1$-$C_6$)alkyl, said aryl being optionally substituted, or
a ($C_1$-$C_6$)alkyl-($C_5$-$C_{12}$)aryl, optionally substituted;
Y is a nitrogen atom, —$NR_eR_f$, an oxygen atom, $OR_g$ or a linker-ligand for the E3 ubiquitin ligase;
wherein $R_e$, $R_f$ and $R_g$ each independently represent:
a hydrogen atom,
a $C_1$-$C_6$ alkyl, optionally substituted,
a $C_5$-$C_{12}$ aryl, optionally substituted,
a ($C_5$-$C_{12}$)aryl-($C_1$-$C_6$)alkyl, said aryl being optionally substituted,
a ($C_1$-$C_6$)alkyl-($C_5$-$C_{12}$)aryl, optionally substituted,
—$C(O)OR_h$, or
—$C(O)R_h$;
$R_1$ represents a hydrogen atom or a lone pair;
$R_3$ represents:
a lone pair,
a hydrogen atom,
a $C_1$-$C_6$ alkyl, optionally substituted,
a $C_5$-$C_{12}$ aryl, optionally substituted,
a ($C_5$-$C_{12}$)aryl-($C_1$-$C_6$)alkyl, said aryl being optionally substituted,
a ($C_1$-$C_6$)alkyl-($C_5$-$C_{12}$)aryl, optionally substituted,
—$C(O)OR_i$,
—$C(O)R_i$, or
a linker-ligand for the E3 ubiquitin ligase;
$R_7$ represents:
a lone pair,
a hydrogen atom,
a $C_1$-$C_6$ alkyl, optionally substituted,
a $C_5$-$C_{12}$ aryl, optionally substituted,
a ($C_5$-$C_{12}$)aryl-($C_1$-$C_6$)alkyl, said aryl being optionally substituted,
a ($C_1$-$C_6$)alkyl-($C_5$-$C_{12}$)aryl, optionally substituted,
—$C(O)OR_j$, or
—$C(O)R_j$;
wherein $R_h$, $R_i$ and $R_j$ each independently represent a hydrogen atom, a $C_1$-$C_6$ alkyl optionally substituted, a $C_5$-$C_{12}$ aryl optionally substituted, a $(C_5-C_{12})$aryl-$(C_1-C_6)$alkyl optionally substituted, a $(C_1-C_6)$alkyl-$(C_5-C_{12})$aryl optionally substituted, a heteroaryl optionally substituted, an alkylheteroaryl optionally substituted, a heteroarylalkyl optionally substituted;

$R_8$ is a hydrogen atom, a halogen atom, a $C_1-C_6$ alkyl optionally substituted, a linker-ligand for the E3 ubiquitin ligase or -A-B;

wherein A represents —$(CH_2)_n$, a sulphur atom, —$SO_2$—, —$CH_2$—O—, —$CH_2$—S—, —$CH_2$—$SO_2$—, an oxygen atom, or —N(H)—;

wherein B represents:
a hydrogen atom,
—OH,
a halogen atom,
—SH,
—$CO_2H$,
a $C_1-C_6$ alkyl, optionally substituted,
a $(C_5-C_{12})$aryl-$(C_1-C_6)$alkyl, optionally substituted,
a $(C_1-C_6)$alkyl-$(C_5-C_{12})$aryl, optionally substituted,
a $C_5-C_{12}$ aryl, optionally substituted by one or more:
  $C_1-C_6$ alkyl groups,
  oxygen atoms,
  sulphur atoms,
  halogen atoms, —amino groups,
  —$(C_1-C_4)$alkanoic acid,
  —$S(O_2)$—$(C_1-C_4)$alkyl,
  —$S(O_2)$-piperidine,
  —$S(O_2)$—(N,N)dimethylamine,
  —$S(O_2)$-morpholine,
  nitro groups,
  —C(=O)—O—$(C_1-C_4)$alkyl,
  —$S(O_2)$—N(H)—$(C_1-C_4)$alkyl,
  oxo-pyrazole optionally substituted by one or more $(C_1-C_4)$alkanoic acid, $(C_1-C_4)$alkyl, halogen atoms or —OH,
  ketone groups,
  pyrazole optionally substituted by one or more $(C_1-C_4)$alkanoic acid, $(C_1-C_4)$alkyl, halogen atoms or —OH,
  pyrrolidine optionally substituted by one or more $(C_1-C_4)$alkanoic acid, $(C_1-C_4)$alkyl, halogen atoms or —OH,
  phenyl,
  benzyl,
  oxy-phenyl,
  oxy-benzyl,
  thiazolidin optionally substituted by one or more $(C_1-C_4)$alkanoic acid, $(C_1-C_4)$alkyl, halogen atoms or —OH,
  —C(=O)—N(H)-benzyl,
  —N(H)-quinazolinone,
  —OH,
  thiophenyl optionally substituted by one or more $(C_1-C_4)$alkanoic acid, $(C_1-C_4)$alkyl, halogen atoms or —OH,
  methyl-tetrahydrofuran, or
  —$CH_2$-pyrazole optionally substituted by one or more $(C_1-C_4)$alkanoic acid, $(C_1-C_4)$alkyl, halogen atoms or —OH;
a $(C_1-C_6)$alkyl-heteroaryl, optionally substituted;
a heteroaryl-$(C_1-C_6)$alkyl, optionally substituted;
a heteroaryl, optionally substituted by one or more:
  $C_1-C_6$ alkyl groups,
  halogen atoms,
  oxygen atoms,
  sulphur atoms,
  amino groups,
  —$(C_1-C_4)$alkanoic acid,
  —$S(O_2)$—$(C_1-C_4)$alkyl,
  —$S(O_2)$-piperidine,
  —$S(O_2)$—(N,N)dimethylamine,
  —$S(O_2)$-morpholine,
  nitro groups,
  —C(=O)—O—$(C_1-C_4)$alkyl,
  —$S(O_2)$—N(H)—$(C_1-C_4)$alkyl,
  oxo-pyrazole optionally substituted by one or more $(C_1-C_4)$alkanoic acid, $(C_1-C_4)$alkyl, halogen atoms or —OH,
  ketone groups,
  pyrazole optionally substituted by one or more $(C_1-C_4)$alkanoic acid, $(C_1-C_4)$alkyl, halogen atoms or —OH,
  pyrrolidine optionally substituted by one or more $(C_1-C_4)$alkanoic acid, $(C_1-C_4)$alkyl, halogen atoms or —OH,
  phenyl,
  benzyl,
  oxy-phenyl,
  oxy-benzyl,
  thiazolidin optionally substituted by one or more $(C_1-C_4)$alkanoic acid, $(C_1-C_4)$alkyl, halogen atoms or —OH,
  —C(=O)—N(H)-benzyl,
  —N(H)-quinazolinone,
  —OH,
  thiophenyl optionally substituted by one or more $(C_1-C_4)$alkanoic acid, $(C_1-C_4)$alkyl, halogen atoms or —OH,
  methyl-tetrahydrofuran, or
  —$CH_2$-pyrazole optionally substituted by one or more $(C_1-C_4)$alkanoic acid, $(C_1-C_4)$alkyl, halogen atoms or —OH;

wherein n represents an integer ranging from 0 to 1, 2, 3, 4, 5, 6, 7, 8, 9 or 10;

or $R_7$ with $R_8$ taken together form a cycle by forming a covalent bond between a $R_7$ group and $R_8$ group as defined above;

or a pharmaceutically acceptable salt thereof and/or tautomeric form thereof.

By the A groups —$CH_2$—O—, —$CH_2$—S— and —$CH_2$—$SO_2$—, in the present invention, it is understood that either —$CH_2$ or —O for —$CH_2$—O—, —$CH_2$ or —S for —$CH_2$—S—, or either —$CH_2$ or —$SO_2$ for —$CH_2$—$SO_2$— can be linked to B, i.e.
—$CH_2$—O— can be either "—$CH_2$—O—B" or "—O—$CH_2$—B";
—$CH_2$—S— can be either "—$CH_2$—S—B" or "—S—$CH_2$—B"; and
—$CH_2$—$SO_2$— can be either "—$CH_2$—$SO_2$—B" or "—$SO_2$—$CH_2$—B".

By the term "or $R_7$ with $R_8$ taken together form a cycle by forming a covalent bond between a $R_7$ group and $R_8$ group as defined above" as defined above, it is understood that $R_7$ and $R_8$ are linked by a hydrocarbon moiety in $C_1-C_6$ comprising optionally a C=O; and wherein a $CH_2$ is replaced by a heteroatom. In such case, the person skilled in the art is able to choose $R_7$ such that $R_7$ is not a lone pair.

An example wherein $R_7$ and $R_8$ optionally form a cycle is

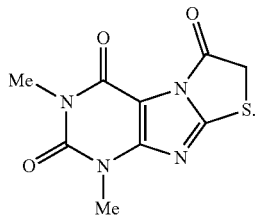 [SMILES: Cn1c(=O)c2c(nc3n2C(=O)CS3)n(C)c1=O]

In the present invention, the term "optionally substituted", unless otherwise specified, refers to substituents as defined above, i.e. halogen atoms, oxygen atoms such as =O, or sulphur atoms and groups selected from a $C_1$-$C_6$ alkyl, cycloalkyl, haloalkyl, alkoxy, haloalkoxy, alkoxycarbonyl, aryl, aryloxy, arylalkyl, alkylaryl, heteroaryl, alkylheteroaryl, heteroarylalkyl, cyano, nitro, nitrile, amino, alkylamino, dialkylamino, arylamino, diarylamino, thioether, —SH, alkylthio, arylthio, hydroxyl group, carboxylic group, sulfonic group, ester group, carbonyl group, ether group, ketone group, —CHOH and —COH.

In a particular embodiment, $R_8$ is substituted by a linker-ligand for the E3 ubiquitin ligase.

In a particular embodiment, X, Y, $R_1$, $R_3$ and $R_7$ are as defined above and $R_8$ represents a -A-B group wherein A represents —($-CH_2$)$_n$ and wherein B represents:
- a hydrogen atom,
- —OH,
- a halogen atom,
- —SH,
- —CO$_2$H,
- a ($C_5$-$C_{12}$)aryl-($C_1$-$C_6$)alkyl, optionally substituted,
- a ($C_1$-$C_6$)alkyl-($C_5$-$C_{12}$)aryl, optionally substituted,
- a $C_5$-$C_{12}$ aryl, optionally substituted by one or more:
  - $C_1$-$C_6$ alkyl groups,
  - oxygen atoms,
  - sulphur atoms,
  - halogen atoms, —amino groups,
  - —($C_1$-$C_4$)alkanoic acid,
  - —S(O$_2$)—($C_1$-$C_4$)alkyl,
  - —S(O$_2$)-piperidine,
  - —S(O$_2$)—(N,N)dimethylamine,
  - —S(O$_2$)-morpholine,
  - nitro groups,
  - —C(=O)—O—($C_1$-$C_4$)alkyl,
  - —S(O$_2$)—N(H)—($C_1$-$C_4$)alkyl,
  - oxo-pyrazole optionally substituted by one or more ($C_1$-$C_4$)alkanoic acid, ($C_1$-$C_4$)alkyl, halogen atoms or —OH,
  - ketone groups,
  - pyrazole optionally substituted by one or more ($C_1$-$C_4$) alkanoic acid, ($C_1$-$C_4$)alkyl, halogen atoms or —OH,
  - pyrrolidine optionally substituted by one or more ($C_1$-$C_4$)alkanoic acid, ($C_1$-$C_4$)alkyl, halogen atoms or —OH,
  - phenyl,
  - benzyl,
  - oxy-phenyl,
  - oxy-benzyl,
  - thiazolidin optionally substituted by one or more ($C_1$-$C_4$)alkanoic acid, ($C_1$-$C_4$)alkyl, halogen atoms or —OH,
  - —C(=O)—N(H)-benzyl,
  - —N(H)-quinazolinone,
  - —OH,
  - thiophenyl optionally substituted by one or more ($C_1$-$C_4$)alkanoic acid, ($C_1$-$C_4$)alkyl, halogen atoms or —OH,
  - methyl-tetrahydrofuran, or
  - —CH$_2$-pyrazole optionally substituted by one or more ($C_1$-$C_4$)alkanoic acid, ($C_1$-$C_4$)alkyl, halogen atoms or —OH;
- a ($C_1$-$C_6$)alkyl-heteroaryl, optionally substituted,
- a heteroaryl-($C_1$-$C_6$)alkyl, optionally substituted,
- a heteroaryl, optionally substituted by one or more:
  - $C_1$-$C_6$ alkyl groups,
  - halogen atoms,
  - oxygen atoms,
  - sulphur atoms,
  - amino groups,
  - —($C_1$-$C_4$)alkanoic acid,
  - —S(O$_2$)—($C_1$-$C_4$)alkyl,
  - —S(O$_2$)-piperidine,
  - —S(O$_2$)—(N,N)dimethylamine,
  - —S(O$_2$)-morpholine,
  - nitro groups,
  - —C(=O)—O—($C_1$-$C_4$)alkyl,
  - —S(O$_2$)—N(H)—($C_1$-$C_4$)alkyl,
  - oxo-pyrazole optionally substituted by one or more ($C_1$-$C_4$)alkanoic acid, ($C_1$-$C_4$)alkyl, halogen atoms or —OH,
  - ketone groups,
  - pyrazole optionally substituted by one or more ($C_1$-$C_4$) alkanoic acid, ($C_1$-$C_4$)alkyl, halogen atoms or —OH,
  - pyrrolidine optionally substituted by one or more ($C_1$-$C_4$)alkanoic acid, ($C_1$-$C_4$)alkyl, halogen atoms or —OH,
  - phenyl,
  - benzyl,
  - oxy-phenyl,
  - oxy-benzyl,
  - thiazolidin optionally substituted by one or more ($C_1$-$C_4$)alkanoic acid, ($C_1$-$C_4$)alkyl, halogen atoms or —OH,
  - —C(=O)—N(H)-benzyl,
  - —N(H)-quinazolinone,
  - —OH,
  - thiophenyl optionally substituted by one or more ($C_1$-$C_4$)alkanoic acid, ($C_1$-$C_4$)alkyl, halogen atoms or —OH,
  - methyl-tetrahydrofuran, or
  - —CH$_2$-pyrazole optionally substituted by one or more ($C_1$-$C_4$)alkanoic acid, ($C_1$-$C_4$)alkyl, halogen atoms or —OH;

wherein n represents an integer ranging from 0 to 1, 2, 3, 4, 5, 6, 7, 8, 9 or 10;

In a particular embodiment, X, Y, $R_1$, $R_3$ and $R_7$ are as defined above and $R_8$ represents a -A-B group wherein A represents a sulphur atom and wherein B represents:
- a hydrogen atom,
- —SH,
- —CO$_2$H,
- a $C_1$-$C_6$ alkyl, optionally substituted,
- a ($C_5$-$C_{12}$)aryl-($C_1$-$C_6$)alkyl, optionally substituted,
- a ($C_1$-$C_6$)alkyl-($C_5$-$C_{12}$)aryl, optionally substituted,
- a $C_5$-$C_{12}$ aryl, optionally substituted by one or more:
  - $C_1$-$C_6$ alkyl groups,
  - oxygen atoms,
  - sulphur atoms,
  - halogen atoms,
  - amino groups, —($C_1$-$C_4$)alkanoic acid,
—$S(O_2)$—($C_1$-$C_4$)alkyl,
—$S(O_2)$-piperidine,
—$S(O_2)$—(N,N)dimethylamine,
—$S(O_2)$-morpholine,
nitro groups,
—C(=O)—O—(C1-C4)alkyl,
—$S(O_2)$—N(H)—($C_1$-$C_4$)alkyl,
oxo-pyrazole optionally substituted by one or more ($C_1$-$C_4$)alkanoic acid, ($C_1$-$C_4$)alkyl, halogen atoms or —OH,
ketone groups,
pyrazole optionally substituted by one or more ($C_1$-$C_4$) alkanoic acid, ($C_1$-$C_4$)alkyl, halogen atoms or —OH,
pyrrolidine optionally substituted by one or more ($C_1$-$C_4$)alkanoic acid, ($C_1$-$C_4$)alkyl, halogen atoms or —OH,
phenyl,
benzyl,
oxy-phenyl,
oxy-benzyl,
thiazolidin optionally substituted by one or more ($C_1$-$C_4$)alkanoic acid, ($C_1$-$C_4$)alkyl, halogen atoms or —OH,
—C(=O)—N(H)-benzyl,
—N(H)-quinazolinone,
—OH,
thiophenyl optionally substituted by one or more ($C_1$-$C_4$)alkanoic acid, ($C_1$-$C_4$)alkyl, halogen atoms or —OH,
methyl-tetrahydrofuran, or
—$CH_2$-pyrazole optionally substituted by one or more ($C_1$-$C_4$)alkanoic acid, ($C_1$-$C_4$)alkyl, halogen atoms or —OH;
a ($C_1$-$C_6$)alkyl-heteroaryl, optionally substituted;
a heteroaryl-($C_1$-$C_6$)alkyl, optionally substituted;
a heteroaryl, optionally substituted by one or more:
$C_1$-$C_6$ alkyl groups,
halogen atoms,
oxygen atoms,
sulphur atoms, —amino groups,
—($C_1$-$C_4$)alkanoic acid,
—$S(O_2)$—($C_1$-$C_4$)alkyl,
—$S(O_2)$-piperidine,
—$S(O_2)$—(N,N)dimethylamine,
—$S(O_2)$-morpholine,
nitro groups,
—C(=O)—O—($C_1$-$C_4$)alkyl,
—$S(O_2)$—N(H)—($C_1$-$C_4$)alkyl,
oxo-pyrazole optionally substituted by one or more ($C_1$-$C_4$)alkanoic acid, ($C_1$-$C_4$)alkyl, halogen atoms or —OH,
ketone groups,
pyrazole optionally substituted by one or more ($C_1$-$C_4$) alkanoic acid, ($C_1$-$C_4$)alkyl, halogen atoms or —OH,
pyrrolidine optionally substituted by one or more ($C_1$-$C_4$)alkanoic acid, ($C_1$-$C_4$)alkyl, halogen atoms or —OH,
phenyl,
benzyl,
oxy-phenyl,
oxy-benzyl,
thiazolidin optionally substituted by one or more ($C_1$-$C_4$)alkanoic acid, ($C_1$-$C_4$)alkyl, halogen atoms or —OH,
—C(=O)—N(H)-benzyl,
—N(H)-quinazolinone,
—OH,
thiophenyl optionally substituted by one or more ($C_1$-$C_4$)alkanoic acid, ($C_1$-$C_4$)alkyl, halogen atoms or —OH,
methyl-tetrahydrofuran, or
—$CH_2$-pyrazole optionally substituted by one or more ($C_1$-$C_4$)alkanoic acid, ($C_1$-$C_4$)alkyl, halogen atoms or —OH.

In a particular embodiment, X, Y, $R_1$, $R_3$ and $R_7$ are as defined above and $R_8$ represents a -A-B group wherein A represents —$SO_2$— and wherein B represents:
a hydrogen atom,
—OH,
a halogen atom,
—SH,
—$CO_2H$,
a $C_1$-$C_6$ alkyl, optionally substituted,
a ($C_5$-$C_{12}$)aryl-($C_1$-$C_6$)alkyl, optionally substituted,
a ($C_1$-$C_6$)alkyl-($C_5$-$C_{12}$)aryl, optionally substituted,
a $C_5$-$C_{12}$ aryl, optionally substituted by one or more:
$C_1$-$C_6$ alkyl groups,
oxygen atoms,
sulphur atoms,
halogen atoms,
amino groups
—($C_1$-$C_4$)alkanoic acid,
—$S(O_2)$—($C_1$-$C_4$)alkyl,
—$S(O_2)$-piperidine,
—$S(O_2)$—(N,N)dimethylamine,
—$S(O_2)$-morpholine,
nitro groups,
—C(=O)—O—($C_1$-$C_4$)alkyl,
—$S(O_2)$—N(H)—($C_1$-$C_4$)alkyl,
oxo-pyrazole optionally substituted by one or more ($C_1$-$C_4$)alkanoic acid, ($C_1$-$C_4$)alkyl, halogen atoms or —OH,
ketone groups,
pyrazole optionally substituted by one or more ($C_1$-$C_4$) alkanoic acid, ($C_1$-$C_4$)alkyl, halogen atoms or —OH,
pyrrolidine optionally substituted by one or more ($C_1$-$C_4$)alkanoic acid, ($C_1$-$C_4$)alkyl, halogen atoms or —OH,
phenyl,
benzyl,
oxy-phenyl,
oxy-benzyl,
thiazolidin optionally substituted by one or more ($C_1$-$C_4$)alkanoic acid, ($C_1$-$C_4$)alkyl, halogen atoms or —OH,
—C(=O)—N(H)-benzyl,
—N(H)-quinazolinone,
—OH,
thiophenyl optionally substituted by one or more ($C_1$-$C_4$)alkanoic acid, ($C_1$-$C_4$)alkyl, halogen atoms or —OH,
methyl-tetrahydrofuran, or
—$CH_2$-pyrazole optionally substituted by one or more (C1-C4)alkanoic acid, ($C_1$-$C_4$)alkyl, halogen atoms or —OH;
a ($C_1$-$C_6$)alkyl-heteroaryl, optionally substituted;
a heteroaryl-($C_1$-$C_6$)alkyl, optionally substituted;
a heteroaryl, optionally substituted by one or more:
$C_1$-$C_6$ alkyl groups,
halogen atoms,
oxygen atoms,
sulphur atoms, —amino groups,
—($C_1$-$C_4$)alkanoic acid, —S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid, (C$_1$-C$_4$)alkyl, halogen atoms or —OH,
ketone groups,
pyrazole optionally substituted by one or more (C$_1$-C$_4$) alkanoic acid, (C$_1$-C$_4$)alkyl, halogen atoms or —OH,
pyrrolidine optionally substituted by one or more (C$_1$-C$_4$)alkanoic acid, (C$_1$-C$_4$)alkyl, halogen atoms or —OH,
phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
—CH$_2$-pyrazole optionally substituted by one or more (C$_1$-C$_4$)alkanoic acid, (C$_1$-C$_4$)alkyl, halogen atoms or —OH.

In a particular embodiment, X, Y, R$_1$, R$_3$ and R$_7$ are as defined above and R$_8$ represents a -A-B group wherein A represents —CH$_2$—S— and wherein B represents:
a hydrogen atom,
—OH,
a halogen atom,
—SH,
—CO$_2$H,
a C$_1$-C$_6$ alkyl, optionally substituted,
a (C$_5$-C$_{12}$)aryl-(C$_1$-C$_6$)alkyl, optionally substituted,
a (C$_1$-C$_6$)alkyl-(C$_5$-C$_{12}$)aryl, optionally substituted,
a C$_5$-C$_{12}$ aryl, optionally substituted by one or more:
C$_1$-C$_6$ alkyl groups,
oxygen atoms,
sulphur atoms,
halogen atoms,
amino groups,
—(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O2)-N(H)—(C$_1$-C$_4$)alkyl,
oxo-pyrazole optionally substituted by one or more (C$_1$-C$_4$)alkanoic acid, (C$_1$-C$_4$)alkyl, halogen atoms or —OH,
ketone groups,
pyrazole optionally substituted by one or more (C$_1$-C$_4$) alkanoic acid, (C$_1$-C$_4$)alkyl, halogen atoms or —OH,
pyrrolidine optionally substituted by one or more (C$_1$-C$_4$)alkanoic acid, (C$_1$-C$_4$)alkyl, halogen atoms or —OH,
phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
—CH$_2$-pyrazole optionally substituted by one or more (C$_1$-C$_4$)alkanoic acid, (C$_1$-C$_4$)alkyl, halogen atoms or —OH;
a (C$_1$-C$_6$)alkyl-heteroaryl, optionally substituted;
a heteroaryl-(C$_1$-C$_6$)alkyl, optionally substituted;
a heteroaryl, optionally substituted by one or more:
C$_1$-C$_6$ alkyl groups,
halogen atoms,
oxygen atoms,
sulphur atoms,
amino groups,
—(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid, (C$_1$-C$_4$)alkyl, halogen atoms or —OH,
ketone groups,
pyrazole optionally substituted by one or more (C$_1$-C$_4$) alkanoic acid, (C$_1$-C$_4$)alkyl, halogen atoms or —OH,
pyrrolidine optionally substituted by one or more (C$_1$-C$_4$)alkanoic acid, (C$_1$-C$_4$)alkyl, halogen atoms or —OH,
phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
—CH$_2$-pyrazole optionally substituted by one or more (C$_1$-C$_4$)alkanoic acid, (C$_1$-C$_4$)alkyl, halogen atoms or —OH.

In a particular embodiment, X, Y, R$_1$, R$_3$ and R$_7$ are as defined above and R$_8$ represents a -A-B group wherein A represents —CH$_2$—SO$_2$— and wherein B represents:
a hydrogen atom,
—OH,
a halogen atom,
—SH,
—CO$_2$H, a $C_1$-$C_6$ alkyl, optionally substituted,
a $(C_5$-$C_{12})$aryl-$(C_1$-$C_6)$alkyl, optionally substituted,
a $(C_1$-$C_6)$alkyl-$(C_5$-$C_{12})$aryl, optionally substituted,
a $C_5$-$C_{12}$ aryl, optionally substituted by one or more:
  $C_1$-$C_6$ alkyl groups,
  oxygen atoms,
  sulphur atoms,
  halogen atoms,
  amino groups,
  —$(C_1$-$C_4)$alkanoic acid,
  —$S(O_2)$—$(C_1$-$C_4)$alkyl,
  —$S(O_2)$-piperidine,
  —$S(O_2)$—(N,N)dimethylamine,
  —$S(O_2)$-morpholine,
  nitro groups,
  —C(=O)—O—$(C_1$-$C_4)$alkyl,
  —S(O2)-N(H)—$(C_1$-$C_4)$alkyl,
  oxo-pyrazole optionally substituted by one or more $(C_1$-$C_4)$alkanoic acid, $(C_1$-$C_4)$alkyl, halogen atoms or —OH,
  ketone groups,
  pyrazole optionally substituted by one or more $(C_1$-$C_4)$ alkanoic acid, $(C_1$-$C_4)$alkyl, halogen atoms or —OH,
  pyrrolidine optionally substituted by one or more $(C_1$-$C_4)$alkanoic acid, $(C_1$-$C_4)$alkyl, halogen atoms or —OH,
  phenyl,
  benzyl,
  oxy-phenyl,
  oxy-benzyl,
  thiazolidin optionally substituted by one or more $(C_1$-$C_4)$alkanoic acid, $(C_1$-$C_4)$alkyl, halogen atoms or —OH,
  —C(=O)—N(H)-benzyl,
  —N(H)-quinazolinone,
  —OH,
  thiophenyl optionally substituted by one or more $(C_1$-$C_4)$alkanoic acid, $(C_1$-$C_4)$alkyl, halogen atoms or —OH,
  methyl-tetrahydrofuran, or
  —$CH_2$-pyrazole optionally substituted by one or more $(C_1$-$C_4)$alkanoic acid, $(C_1$-$C_4)$alkyl, halogen atoms or —OH;
a $(C_1$-$C_6)$alkyl-heteroaryl, optionally substituted;
a heteroaryl-$(C_1$-$C_6)$alkyl, optionally substituted;
a heteroaryl, optionally substituted by one or more:
  $C_1$-$C_6$ alkyl groups,
  halogen atoms,
  oxygen atoms,
  sulphur atoms,
  amino groups,
  —$(C_1$-$C_4)$alkanoic acid,
  —$S(O_2)$—$(C_1$-$C_4)$alkyl,
  —$S(O_2)$-piperidine,
  —$S(O_2)$—(N,N)dimethylamine,
  —$S(O_2)$-morpholine,
  nitro groups,
  —C(=O)—O—$(C_1$-$C_4)$alkyl,
  —S(O2)-N(H)—$(C_1$-$C_4)$alkyl,
  oxo-pyrazole optionally substituted by one or more $(C_1$-$C_4)$alkanoic acid, $(C_1$-$C_4)$alkyl, halogen atoms or —OH,
  ketone groups,
  pyrazole optionally substituted by one or more $(C_1$-$C_4)$ alkanoic acid, $(C_1$-$C_4)$alkyl, halogen atoms or —OH,
  pyrrolidine optionally substituted by one or more $(C_1$-$C_4)$alkanoic acid, $(C_1$-$C_4)$alkyl, halogen atoms or —OH,
  phenyl,
  benzyl,
  oxy-phenyl,
  oxy-benzyl,
  thiazolidin optionally substituted by one or more $(C_1$-$C_4)$alkanoic acid, $(C_1$-$C_4)$alkyl, halogen atoms or —OH,
  —C(=O)—N(H)-benzyl,
  —N(H)-quinazolinone,
  —OH,
  thiophenyl optionally substituted by one or more $(C_1$-$C_4)$alkanoic acid, $(C_1$-$C_4)$alkyl, halogen atoms or —OH,
  methyl-tetrahydrofuran, or
  —$CH_2$-pyrazole optionally substituted by one or more $(C_1$-$C_4)$alkanoic acid, $(C_1$-$C_4)$alkyl, halogen atoms or —OH.

In a particular embodiment, X, Y, $R_1$, $R_3$ and $R_7$ are as defined above and $R_8$ represents a -A-B group wherein A represents an oxygen atom and wherein B represents:
  a hydrogen atom,
  —$CO_2H$,
  a $C_1$-$C_6$ alkyl, optionally substituted,
  a $(C_5$-$C_{12})$aryl-$(C_1$-$C_6)$alkyl, optionally substituted,
  a $(C_1$-$C_6)$alkyl-$(C_5$-$C_{12})$aryl, optionally substituted,
  a $C_5$-$C_{12}$ aryl, optionally substituted by one or more:
    $C_1$-$C_6$ alkyl groups,
    oxygen atoms,
    sulphur atoms,
    halogen atoms,
    amino groups,
    —$(C_1$-$C_4)$alkanoic acid,
    —$S(O_2)$—$(C_1$-$C_4)$alkyl,
    —$S(O_2)$-piperidine,
    —$S(O_2)$—(N,N)dimethylamine,
    —$S(O_2)$-morpholine,
    nitro groups,
    —C(=O)—O—$(C_1$-$C_4)$alkyl,
    —S(O2)-N(H)—$(C_1$-$C_4)$alkyl,
    oxo-pyrazole optionally substituted by one or more $(C_1$-$C_4)$alkanoic acid, $(C_1$-$C_4)$alkyl, halogen atoms or —OH,
    ketone groups,
    pyrazole optionally substituted by one or more $(C_1$-$C_4)$ alkanoic acid, $(C_1$-$C_4)$alkyl, halogen atoms or —OH,
    pyrrolidine optionally substituted by one or more $(C_1$-$C_4)$alkanoic acid, $(C_1$-$C_4)$alkyl, halogen atoms or —OH,
    phenyl,
    benzyl,
    oxy-phenyl,
    oxy-benzyl,
    thiazolidin optionally substituted by one or more $(C_1$-$C_4)$alkanoic acid, $(C_1$-$C_4)$alkyl, halogen atoms or —OH,
    —C(=O)—N(H)-benzyl,
    —N(H)-quinazolinone,
    —OH,
    thiophenyl optionally substituted by one or more $(C_1$-$C_4)$alkanoic acid, $(C_1$-$C_4)$alkyl, halogen atoms or —OH, methyl-tetrahydrofuran, or
—CH$_2$-pyrazole optionally substituted by one or more (C$_1$-C$_4$)alkanoic acid, (C$_1$-C$_4$)alkyl, halogen atoms or —OH;

a (C$_1$-C$_6$)alkyl-heteroaryl, optionally substituted;
a heteroaryl-(C$_1$-C$_6$)alkyl, optionally substituted;
a heteroaryl, optionally substituted by one or more:
  C$_1$-C$_6$ alkyl groups,
  halogen atoms,
  oxygen atoms,
  sulphur atoms, —amino groups,
  —(C$_1$-C$_4$)alkanoic acid,
  —S(O$_2$)—(C$_1$-C$_4$)alkyl,
  —S(O$_2$)-piperidine,
  —S(O$_2$)—(N,N)dimethylamine,
  —S(O$_2$)-morpholine,
  nitro groups,
  —C(=O)—O—(C$_1$-C$_4$)alkyl,
  —S(O$_2$)—N(H)—(C$_1$-C$_4$)alkyl,
  oxo-pyrazole optionally substituted by one or more (C$_1$-C$_4$)alkanoic acid, (C$_1$-C$_4$)alkyl, halogen atoms or —OH,
  ketone groups,
  pyrazole optionally substituted by one or more (C$_1$-C$_4$) alkanoic acid, (C$_1$-C$_4$)alkyl, halogen atoms or —OH,
  pyrrolidine optionally substituted by one or more (C$_1$-C$_4$)alkanoic acid, (C$_1$-C$_4$)alkyl, halogen atoms or —OH,
  phenyl,
  benzyl,
  oxy-phenyl,
  oxy-benzyl,
  thiazolidin optionally substituted by one or more (C$_1$-C$_4$)alkanoic acid, (C$_1$-C$_4$)alkyl, halogen atoms or —OH,
  —C(=O)—N(H)-benzyl,
  —N(H)-quinazolinone,
  —OH,
  thiophenyl optionally substituted by one or more (C$_1$-C$_4$)alkanoic acid, (C$_1$-C$_4$)alkyl, halogen atoms or —OH,
  methyl-tetrahydrofuran, or
  —CH$_2$-pyrazole optionally substituted by one or more (C$_1$-C$_4$)alkanoic acid, (C$_1$-C$_4$)alkyl, halogen atoms or —OH.

In a particular embodiment, X, Y, R$_1$, R$_3$ and R$_7$ are as defined above and R$_8$ represents a -A-B group wherein A represents —N(H)— and wherein B represents:
  a hydrogen atom,
  —OH,
  —CO$_2$H,
  a C$_1$-C$_6$ alkyl, optionally substituted,
  a (C$_5$-C$_{12}$)aryl-(C$_1$-C$_6$)alkyl, optionally substituted,
  a (C$_1$-C$_6$)alkyl-(C$_5$-C$_{12}$)aryl, optionally substituted,
  a C$_5$-C$_{12}$ aryl, optionally substituted by one or more:
    C$_1$-C$_6$ alkyl groups,
    oxygen atoms,
    sulphur atoms,
    halogen atoms, —amino groups,
    —(C$_1$-C$_4$)alkanoic acid,
    —S(O$_2$)—(C$_1$-C$_4$)alkyl,
    —S(O$_2$)-piperidine,
    —S(O$_2$)—(N,N)dimethylamine,
    —S(O$_2$)-morpholine,
    nitro groups,
    —C(=O)—O—(C$_1$-C$_4$)alkyl,
    —S(O2)-N(H)—(C$_1$-C$_4$)alkyl,
    oxo-pyrazole optionally substituted by one or more (C$_1$-C$_4$)alkanoic acid, (C$_1$-C$_4$)alkyl, halogen atoms or —OH,
    ketone groups,
    pyrazole optionally substituted by one or more (C$_1$-C$_4$) alkanoic acid, (C$_1$-C$_4$)alkyl, halogen atoms or —OH,
    pyrrolidine optionally substituted by one or more (C$_1$-C$_4$)alkanoic acid, (C$_1$-C$_4$)alkyl, halogen atoms or —OH,
    phenyl,
    benzyl,
    oxy-phenyl,
    oxy-benzyl,
    thiazolidin optionally substituted by one or more (C$_1$-C$_4$)alkanoic acid, (C$_1$-C$_4$)alkyl, halogen atoms or —OH,
    —C(=O)—N(H)-benzyl,
    —N(H)-quinazolinone,
    —OH,
    thiophenyl optionally substituted by one or more (C$_1$-C$_4$)alkanoic acid, (C$_1$-C$_4$)alkyl, halogen atoms or —OH,
    methyl-tetrahydrofuran, or
    —CH$_2$-pyrazole optionally substituted by one or more (C$_1$-C$_4$)alkanoic acid, (C$_1$-C$_4$)alkyl, halogen atoms or —OH;

a (C$_1$-C$_6$)alkyl-heteroaryl, optionally substituted;
a heteroaryl-(C$_1$-C$_6$)alkyl, optionally substituted;
a heteroaryl, optionally substituted by one or more:
  C$_1$-C$_6$ alkyl groups,
  halogen atoms,
  oxygen atoms,
  sulphur atoms,
  amino groups,
  —(C$_1$-C$_4$)alkanoic acid,
  —S(O$_2$)—(C$_1$-C$_4$)alkyl,
  —S(O$_2$)-piperidine,
  —S(O$_2$)—(N,N)dimethylamine,
  —S(O$_2$)-morpholine,
  nitro groups,
  —C(=O)—O—(C$_1$-C$_4$)alkyl,
  —S(O$_2$)—N(H)—(C$_1$-C$_4$)alkyl,
  oxo-pyrazole optionally substituted by one or more (C$_1$-C$_4$)alkanoic acid, (C$_1$-C$_4$)alkyl, halogen atoms or —OH,
  ketone groups,
  pyrazole optionally substituted by one or more (C$_1$-C$_4$) alkanoic acid, (C$_1$-C$_4$)alkyl, halogen atoms or —OH,
  pyrrolidine optionally substituted by one or more (C$_1$-C$_4$)alkanoic acid, (C$_1$-C$_4$)alkyl, halogen atoms or —OH,
  phenyl,
  benzyl,
  oxy-phenyl,
  oxy-benzyl,
  thiazolidin optionally substituted by one or more (C$_1$-C$_4$)alkanoic acid, (C$_1$-C$_4$)alkyl, halogen atoms or —OH,
  —C(=O)—N(H)-benzyl,
  —N(H)-quinazolinone,
  —OH,
  thiophenyl optionally substituted by one or more (C$_1$-C$_4$)alkanoic acid, (C$_1$-C$_4$)alkyl, halogen atoms or —OH, methyl-tetrahydrofuran, or
—CH$_2$-pyrazole optionally substituted by one or more (C$_1$-C$_4$)alkanoic acid, (C$_1$-C$_4$)alkyl, halogen atoms or —OH.

In a particular embodiment, X, Y, R$_1$, R$_3$ and R$_7$ are as defined above and R$_8$ represents a -A-B group wherein A represents —CH$_2$—O— and wherein B represents:
  a hydrogen atom,
  —OH,
  —CO$_2$H,
  a C$_1$-C$_6$ alkyl, optionally substituted,
  a (C$_5$-C$_{12}$)aryl-(C$_1$-C$_6$)alkyl, optionally substituted,
  a (C$_1$-C$_6$)alkyl-(C$_5$-C$_{12}$)aryl, optionally substituted,
  a C$_5$-C$_{12}$ aryl, optionally substituted by one or more:
    C$_1$-C$_6$ alkyl groups,
    oxygen atoms,
    sulphur atoms,
    halogen atoms,
    amino groups,
    (C$_1$-C$_4$)alkanoic acid,
    —S(O$_2$)—(C$_1$-C$_4$)alkyl,
    —S(O$_2$)-piperidine,
    —S(O$_2$)—(N,N)dimethylamine,
    —S(O$_2$)-morpholine,
    nitro groups,
    —C(=O)—O—(C$_1$-C$_4$)alkyl,
    —S(O2)-N(H)—(C$_1$-C$_4$)alkyl,
    oxo-pyrazole optionally substituted by one or more (C$_1$-C$_4$)alkanoic acid, (C$_1$-C$_4$)alkyl, halogen atoms or —OH,
    ketone groups,
    pyrazole optionally substituted by one or more (C$_1$-C$_4$) alkanoic acid, (C$_1$-C$_4$)alkyl, halogen atoms or —OH,
    pyrrolidine optionally substituted by one or more (C$_1$-C$_4$)alkanoic acid, (C$_1$-C$_4$)alkyl, halogen atoms or —OH,
    phenyl,
    benzyl,
    oxy-phenyl,
    oxy-benzyl,
    thiazolidin optionally substituted by one or more (C$_1$-C$_4$)alkanoic acid, (C$_1$-C$_4$)alkyl, halogen atoms or —OH,
    —C(=O)—N(H)-benzyl,
    —N(H)-quinazolinone,
    —OH,
    thiophenyl optionally substituted by one or more (C$_1$-C$_4$)alkanoic acid, (C$_1$-C$_4$)alkyl, halogen atoms or —OH,
    methyl-tetrahydrofuran, or
    —CH$_2$-pyrazole optionally substituted by one or more (C$_1$-C$_4$)alkanoic acid, (C$_1$-C$_4$)alkyl, halogen atoms or —OH;
  a (C$_1$-C$_6$)alkyl-heteroaryl, optionally substituted;
  a heteroaryl-(C$_1$-C$_6$)alkyl, optionally substituted;
  a heteroaryl, optionally substituted by one or more:
    C$_1$-C$_6$ alkyl groups,
    halogen atoms,
    oxygen atoms,
    sulphur atoms,
    amino groups,
    —(C$_1$-C$_4$)alkanoic acid,
    —S(O$_2$)—(C$_1$-C$_4$)alkyl,
    —S(O$_2$)-piperidine,
    —S(O$_2$)—(N,N)dimethylamine,
    —S(O$_2$)-morpholine,
    nitro groups,
    —C(=O)—O—(C$_1$-C$_4$)alkyl,
    —S(O$_2$)—N(H)—(C$_1$-C$_4$)alkyl,
    oxo-pyrazole optionally substituted by one or more (C$_1$-C$_4$)alkanoic acid, (C$_1$-C$_4$)alkyl, halogen atoms or —OH,
    ketone groups,
    pyrazole optionally substituted by one or more (C$_1$-C$_4$) alkanoic acid, (C$_1$-C$_4$)alkyl, halogen atoms or —OH,
    pyrrolidine optionally substituted by one or more (C$_1$-C$_4$)alkanoic acid, (C$_1$-C$_4$)alkyl, halogen atoms or —OH,
    phenyl,
    benzyl,
    oxy-phenyl,
    oxy-benzyl,
    thiazolidin optionally substituted by one or more (C$_1$-C$_4$)alkanoic acid, (C$_1$-C$_4$)alkyl, halogen atoms or —OH,
    —C(=O)—N(H)-benzyl,
    —N(H)-quinazolinone,
    —OH,
    thiophenyl optionally substituted by one or more (C$_1$-C$_4$)alkanoic acid, (C$_1$-C$_4$)alkyl, halogen atoms or —OH,
    methyl-tetrahydrofuran, or
    —CH$_2$-pyrazole optionally substituted by one or more (C$_1$-C$_4$)alkanoic acid, (C$_1$-C$_4$)alkyl, halogen atoms or —OH.

In a particular embodiment, in the general formula (I) as defined above:
  X is an oxygen atom, —OR$_a$, a sulphur atom, —SR$_b$, a nitrogen atom, —NR$_c$, or —NR$_c$R$_d$;
    wherein R$_a$, R$_b$, R$_c$ and R$_d$ each independently represent:
      a hydrogen atom,
      a C$_1$-C$_6$ alkyl, optionally substituted, or
      a (C$_5$-C$_{12}$)aryl-(C$_1$-C$_6$)alkyl, said aryl being optionally substituted;
  Y is a nitrogen atom, —NR$_e$R$_f$, an oxygen atom, —OR$_g$ or a linker-ligand for the E3 ubiquitin ligase;
    wherein R$_e$, R$_f$ and R$_g$ each independently represent:
      a hydrogen atom,
      a C$_1$-C$_6$ alkyl, optionally substituted,
      a C$_5$-C$_{12}$ aryl, optionally substituted,
      a (C$_5$-C$_{12}$)aryl-(C$_1$-C$_6$)alkyl, said aryl being optionally substituted,
      —C(O)OR$_h$, or
      —C(O)R$_h$;
  R$_1$ represents a hydrogen atom or a lone pair;
  R$_3$ represents:
    a lone pair,
    a hydrogen atom,
    a C$_1$-C$_6$ alkyl, optionally substituted,
    a C$_5$-C$_{12}$ aryl, optionally substituted,
    a (C$_5$-C$_{12}$)aryl-(C$_1$-C$_6$)alkyl, said aryl being optionally substituted,
    —C(O)OR$_i$,
    —C(O)R$_i$, or
    a linker-ligand for the E3 ubiquitin ligase;
  R$_7$ represents:
    a lone pair,
    a hydrogen atom,
    a C$_1$-C$_6$ alkyl, optionally substituted,
    a C$_5$-C$_{12}$ aryl, optionally substituted,
    a (C$_5$-C$_{12}$)aryl-(C$_1$-C$_6$)alkyl, said aryl being optionally substituted, —C(O)OR$_j$, or
—C(O)R$_j$;
wherein R$_h$, R$_i$ and R$_j$ each independently represent a hydrogen atom, a C$_1$-C$_6$ alkyl optionally substituted, a C$_5$-C$_{12}$ aryl optionally substituted, a (C$_5$-C$_{12}$)aryl-(C$_1$-C$_6$)alkyl optionally substituted, a (C$_1$-C$_6$)alkyl-(C$_5$-C$_{12}$)aryl optionally substituted, a heteroaryl optionally substituted, an alkylheteroaryl optionally substituted, a heteroarylalkyl optionally substituted;

R$_8$ is a hydrogen atom, a halogen atom, a C$_1$-C$_6$ alkyl optionally substituted, a linker-ligand for the E3 ubiquitin ligase or -A-B;
wherein A represents —(—CH$_2$)$_n$, a sulphur atom, —SO$_2$—, —CH$_2$—O—, —CH$_2$—S—, —CH$_2$—SO$_2$—, an oxygen atom, or —N(H)—;
wherein B represents:
a hydrogen atom,
—OH,
a halogen atom,
—SH,
—CO$_2$H,
a C$_1$-C$_6$ alkyl, optionally substituted by CO$_2$H,
a C$_5$-C$_{12}$ aryl, optionally substituted by one or more:
C$_1$-C$_6$ alkyl,
oxygen atoms,
sulphur atoms,
halogen atoms,
amino groups,
—(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid, (C$_1$-C$_4$)alkyl, halogen atoms or —OH,
ketone groups,
pyrazole optionally substituted by one or more (C$_1$-C$_4$)alkanoic acid, (C$_1$-C$_4$)alkyl, halogen atoms or —OH,
pyrrolidine optionally substituted by one or more (C$_1$-C$_4$)alkanoic acid, (C$_1$-C$_4$)alkyl, halogen atoms or —OH,
phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
—CH$_2$-pyrazole optionally substituted by one or more (C$_1$-C$_4$)alkanoic acid, (C$_1$-C$_4$)alkyl, halogen atoms or —OH; or
a heteroaryl, optionally substituted by one or more:
C$_1$-C$_6$ alkyl,
halogen atoms,
oxygen atoms,
sulphur atoms,
amino groups,
—(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid, (C$_1$-C$_4$)alkyl, halogen atoms or —OH,
ketone groups,
pyrazole optionally substituted by one or more (C$_1$-C$_4$)alkanoic acid, (C$_1$-C$_4$)alkyl, halogen atoms or —OH,
pyrrolidine optionally substituted by one or more (C$_1$-C$_4$)alkanoic acid, (C$_1$-C$_4$)alkyl, halogen atoms or —OH,
phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
—CH$_2$-pyrazole optionally substituted by one or more (C$_1$-C$_4$)alkanoic acid, (C$_1$-C$_4$)alkyl, halogen atoms or —OH;
wherein n represents an integer ranging from 0 to 1, 2, 3, 4, 5, 6, 7, 8, 9 or 10;
or R$_7$ with R$_8$ taken together form a cycle by forming a covalent bond between a R$_7$ group and R$_8$ group as defined above;
or a pharmaceutically acceptable salt thereof and/or tautomeric form thereof.

In another embodiment, in the general formula (I) as defined above:
X represents an oxygen atom, or —SH;
Y represents an oxygen atom, —NH$_2$, NHR$_k$, or a linker-ligand for the E3 ubiquitin ligase;
wherein R$_k$ represents —C(O)OR$_l$ wherein R$_l$ represents a C$_1$-C$_6$ alkyl, preferably a C$_1$-C$_4$ alkyl;
R$_1$ represents:
a lone pair, or
a hydrogen atom;
R$_3$ represents:
a lone pair,
a hydrogen atom,
a C$_1$-C$_6$ alkyl,
a (C$_5$-C$_{12}$)aryl-(C$_1$-C$_6$)alkyl, optionally substituted and preferably by a halogen atom or by a C$_1$-C$_6$ alkyl preferably a C$_1$-C$_4$ alkyl,
—C(O)OR$_m$ wherein R$_m$ is a C$_1$-C$_6$ alkyl and preferably a C$_1$-C$_4$ alkyl, or
a linker-ligand for the E3 ubiquitin ligase;
R$_7$ represents:
a lone pair,
a hydrogen atom, $C_1$-$C_6$ alkyl, preferably a $C_1$-$C_4$ alkyl,
—C(O)$R_n$ wherein $R_n$ is a $C_1$-$C_6$ alkyl, preferably a $C_1$-$C_4$ alkyl;

$R_8$ represents:
a hydrogen atom,
a halogen atom,
a $C_5$-$C_{12}$ aryl, optionally substituted by a halogen atom,
a $C_1$-$C_6$ alkyl, optionally substituted by —OH, a halogen atom, or —S-heteroaryl said heteroaryl being optionally substituted by one or more amino groups, $C_1$-$C_4$ alkyl,
—SH,
—S—($C_1$-$C_6$)alkyl wherein the alkyl is optionally substituted by COOH,
—$SO_2$—($C_1$-$C_6$)alkyl wherein the alkyl is optionally substituted by COOH,
—S-heteroaryl said heteroaryl being optionally substituted by one or more amino groups, or $C_1$-$C_4$ alkyl,
—S—($C_1$-$C_6$)alkyl-heteroaryl said heteroaryl being optionally substituted by one or more amino groups, $C_1$-$C_4$ alkyl, or =O,
—$SO_2$-heteroaryl said heteroaryl being optionally substituted by one or more amino groups or $C_1$-$C_4$ alkyl,
$CH_2$—S-heteroaryl said heteroaryl being optionally substituted by one or more:
$C_1$-$C_6$ alkyl,
halogen atoms,
oxygen atoms,
sulphur atoms,
amino groups,
($C_1$-$C_4$)alkanoic acid,
—S($O_2$)—($C_1$-$C_4$)alkyl,
—S($O_2$)-piperidine,
—S($O_2$)—(N,N)dimethylamine,
—S($O_2$)-morpholine,
nitro groups,
—C(=O)—O—($C_1$-$C_4$)alkyl,
—S($O_2$)—N(H)—($C_1$-$C_4$)alkyl,
oxo-pyrazole optionally substituted by one or more ($C_1$-$C_4$)alkanoic acid, ($C_1$-$C_4$)alkyl, halogen atoms or —OH,
ketone groups,
pyrazole optionally substituted by one or more ($C_1$-$C_4$)alkanoic acid, ($C_1$-$C_4$)alkyl, halogen atoms or —OH,
pyrrolidine optionally substituted by one or more ($C_1$-$C_4$)alkanoic acid, ($C_1$-$C_4$)alkyl, halogen atoms or —OH,
phenyl,
benzyl,
oxy-phenyl,
oxy-benzyl,
thiazolidin optionally substituted by one or more ($C_1$-$C_4$)alkanoic acid, ($C_1$-$C_4$)alkyl, halogen atoms or —OH,
—C(=O)—N(H)-benzyl,
—N(H)-quinazolinone,
—OH,
thiophenyl optionally substituted by one or more ($C_1$-$C_4$)alkanoic acid, ($C_1$-$C_4$)alkyl, halogen atoms or —OH,
methyl-tetrahydrofuran, or
$CH_2$-pyrazole optionally substituted by one or more ($C_1$-$C_4$)alkanoic acid, ($C_1$-$C_4$)alkyl, halogen atoms or —OH;
$CH_2$—O-heteroaryl said heteroaryl being optionally substituted by one or more:
$C_1$-$C_6$ alkyl,
halogen atoms,
oxygen atoms,
sulphur atoms,
amino groups,
($C_1$-$C_4$)alkanoic acid,
—S($O_2$)—($C_1$-$C_4$)alkyl,
—S($O_2$)-piperidine,
—S($O_2$)—(N,N)dimethylamine,
—S($O_2$)-morpholine,
nitro groups,
—C(=O)—O—($C_1$-$C_4$)alkyl,
—S($O_2$)—N(H)—($C_1$-$C_4$)alkyl,
oxo-pyrazole optionally substituted by one or more ($C_1$-$C_4$)alkanoic acid, ($C_1$-$C_4$)alkyl, halogen atoms or —OH,
ketone groups,
pyrazole optionally substituted by one or more ($C_1$-$C_4$)alkanoic acid, ($C_1$-$C_4$)alkyl, halogen atoms or —OH,
pyrrolidine optionally substituted by one or more ($C_1$-$C_4$)alkanoic acid, ($C_1$-$C_4$)alkyl, halogen atoms or —OH,
phenyl,
benzyl,
oxy-phenyl,
oxy-benzyl,
thiazolidin optionally substituted by one or more ($C_1$-$C_4$)alkanoic acid, ($C_1$-$C_4$)alkyl, halogen atoms or —OH,
—C(=O)—N(H)-benzyl,
—N(H)-quinazolinone,
—OH,
thiophenyl optionally substituted by one or more ($C_1$-$C_4$)alkanoic acid, ($C_1$-$C_4$)alkyl, halogen atoms or —OH,
methyl-tetrahydrofuran, or
$CH_2$-pyrazole optionally substituted by one or more ($C_1$-$C_4$)alkanoic acid, ($C_1$-$C_4$)alkyl, halogen atoms or —OH;
$CH_2$—S-aryl said aryl being optionally substituted by one or more:
$C_1$-$C_6$ alkyl,
halogen atoms,
oxygen atoms,
sulphur atoms,
amino groups,
—($C_1$-$C_4$)alkanoic acid,
—S($O_2$)—($C_1$-$C_4$)alkyl,
—S($O_2$)-piperidine,
—S($O_2$)—(N,N)dimethylamine,
—S($O_2$)-morpholine,
nitro groups,
—C(=O)—O—($C_1$-$C_4$)alkyl,
—S($O_2$)—N(H)—($C_1$-$C_4$)alkyl,
oxo-pyrazole optionally substituted by one or more ($C_1$-$C_4$)alkanoic acid, ($C_1$-$C_4$)alkyl, halogen atoms or —OH,
ketone groups,
pyrazole optionally substituted by one or more ($C_1$-$C_4$)alkanoic acid, ($C_1$-$C_4$)alkyl, halogen atoms or —OH,
pyrrolidine optionally substituted by one or more ($C_1$-$C_4$)alkanoic acid, ($C_1$-$C_4$)alkyl, halogen atoms or —OH, phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
CH$_2$-pyrazole optionally substituted by one or more (C$_1$-C$_4$)alkanoic acid, (C$_1$-C$_4$)alkyl, halogen atoms or —OH;
CH$_2$—O-aryl said aryl being optionally substituted by one or more:
C$_1$-C$_6$ alkyl,
halogen atoms,
oxygen atoms,
sulphur atoms,
amino groups,
—(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid, (C$_1$-C$_4$)alkyl, halogen atoms or —OH,
ketone groups,
pyrazole optionally substituted by one or more (C$_1$-C$_4$)alkanoic acid, (C$_1$-C$_4$)alkyl, halogen atoms or —OH,
pyrrolidine optionally substituted by one or more (C$_1$-C$_4$)alkanoic acid, (C$_1$-C$_4$)alkyl, halogen atoms or —OH,
phenyl,
benzyl,
oxy-phenyl,
oxy-benzyl,
thiazolidin optionally substituted by one or more (C$_1$-C$_4$)alkanoic acid, (C$_1$-C$_4$)alkyl, halogen atoms or —OH,
—C(=O)—N(H)-benzyl,
—N(H)-quinazolinone,
—OH,
thiophenyl optionally substituted by one or more (C$_1$-C$_4$)alkanoic acid, (C$_1$-C$_4$)alkyl, halogen atoms or —OH,
methyl-tetrahydrofuran, or
CH$_2$-pyrazole optionally substituted by one or more (C$_1$-C$_4$)alkanoic acid, (C$_1$-C$_4$)alkyl, halogen atoms or —OH;
a linker-ligand for the E3 ubiquitin ligase;
or R$_7$ with R$_8$ taken together form a cycle by forming a covalent bond between a R$_7$ group and R$_8$ group as defined above wherein R$_7$ and R$_8$ form together a cycloalkyl, cycloalkylaryl, or cycloheteroaryl, which can be substituted by =O.

In a particular embodiment, the inhibitor is selected from the group consisting of:

TABLE 1

| | a | b | c |
|---|---|---|---|
| 1 | guanine | 7-Me guanine | 7-Et guanine |
| 2 | 6-thioguanine | xanthine | 7-Me xanthine |
| 3 | 7-Et xanthine | 7-i-Bu xanthine | 7-Et, 2-(t-BuO-C(=O)-NH) guanine |

TABLE 1-continued
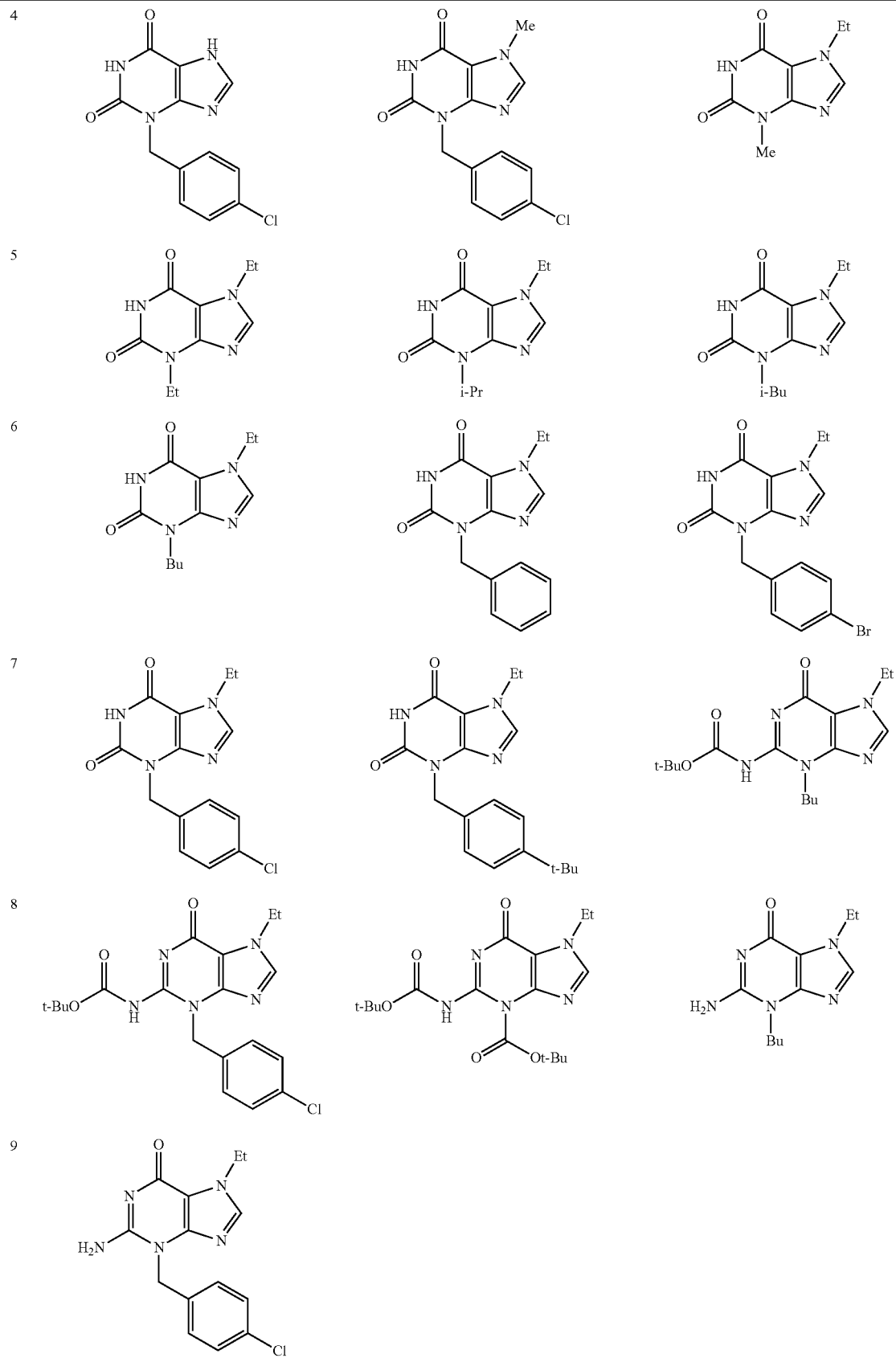

TABLE 1-continued
| | | |
|---|---|---|
| 10 | | 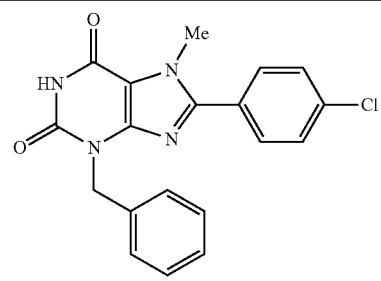 |
| 11 | 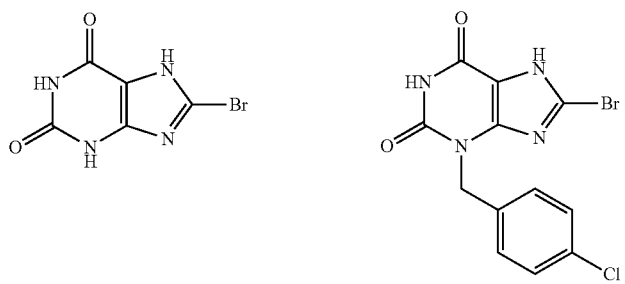 | |
| 12 | 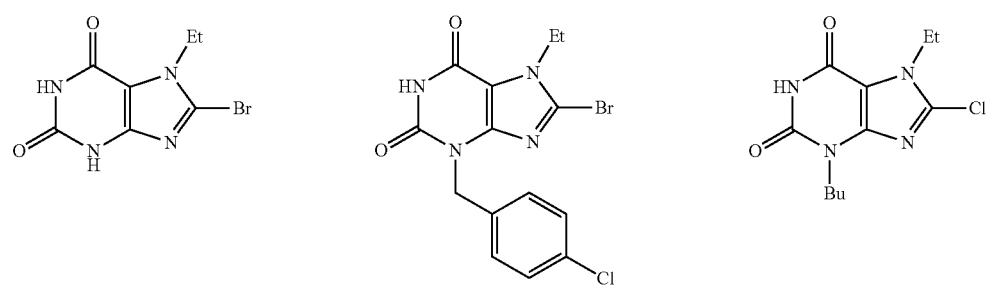 | |
| 14 | | 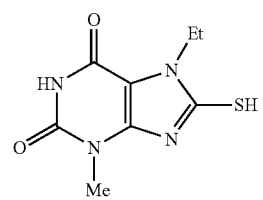 [SMILES: CCn1c(S)nc2c1c(=O)[nH]c(=O)n2C] |
| 15 | 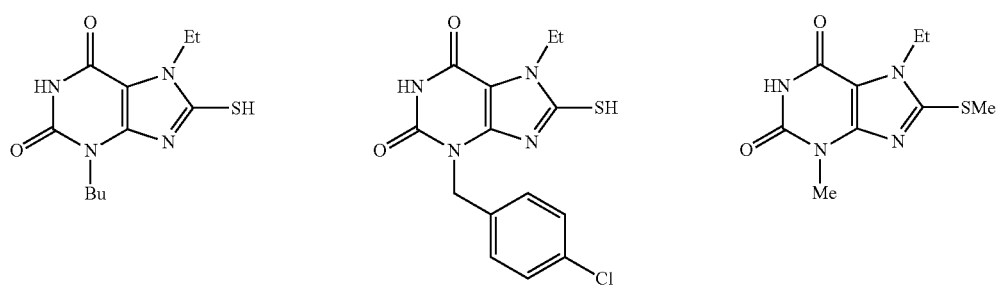 | |
| 16 | 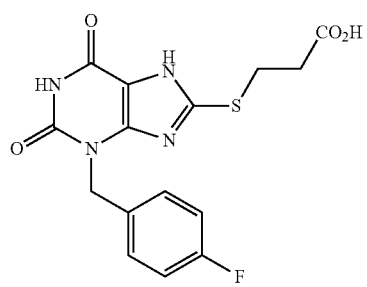 [SMILES: O=C(O)CCSc1nc2c([nH]1)c(=O)[nH]c(=O)n2Cc1ccc(F)cc1] | |

TABLE 1-continued
| | a | b | c |
|---|---|---|---|
| 17 | 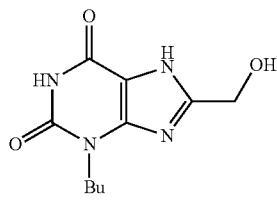 | 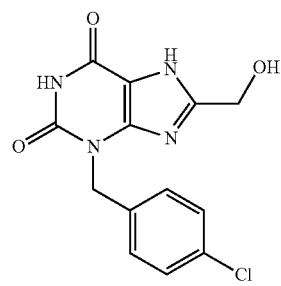 [SMILES: O=c1[nH]c(=O)n(Cc2ccc(Cl)cc2)c2nc(CO)[nH]c12] | 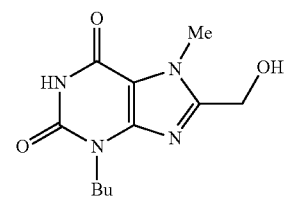 |
| 18 | 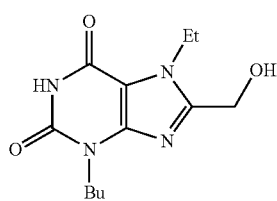 | 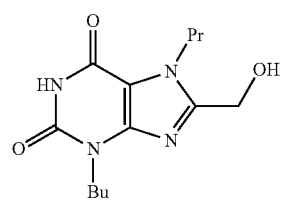 | 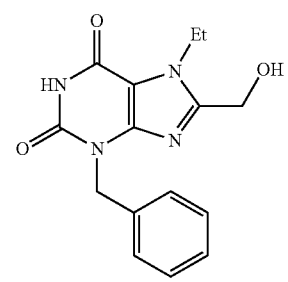 [SMILES: CCn1c(CO)nc2c1c(=O)[nH]c(=O)n2Cc1ccccc1] |
| 19 | 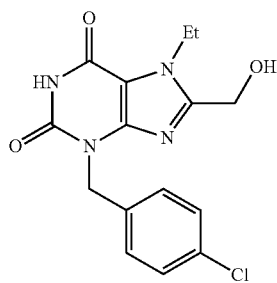 [SMILES: CCn1c(CO)nc2c1c(=O)[nH]c(=O)n2Cc1ccc(Cl)cc1] | | 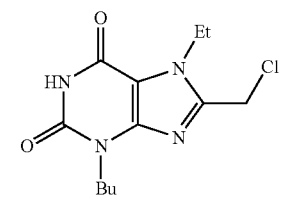 |
| | a | b |
|---|---|---|
| 20 | 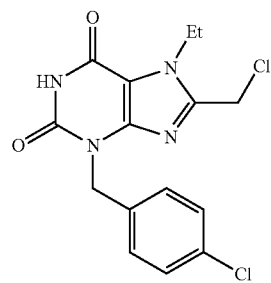 [SMILES: CCn1c(CCl)nc2c1c(=O)[nH]c(=O)n2Cc1ccc(Cl)cc1] | 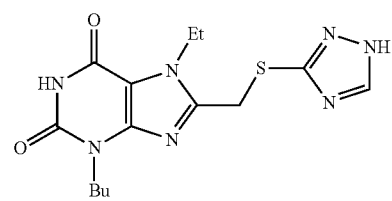 |
| 21 | 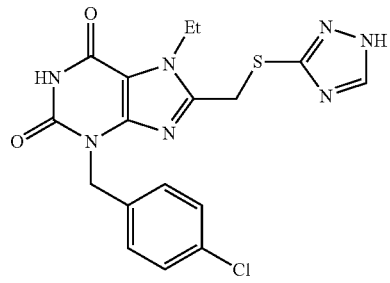 [SMILES: CCn1c(CSc2nc[nH]n2)nc2c1c(=O)[nH]c(=O)n2Cc1ccc(Cl)cc1] | 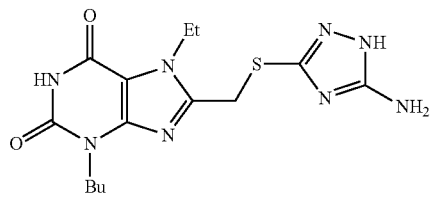 |

TABLE 1-continued
| 22 | 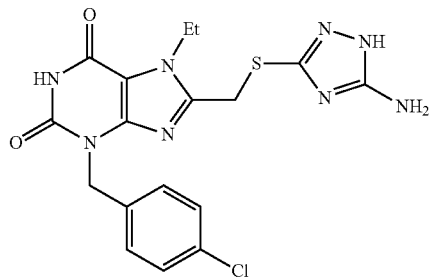 [SMILES: CCn1c(CSc2n[nH]c(N)n2)nc2c1c(=O)[nH]c(=O)n2Cc1ccc(Cl)cc1] | 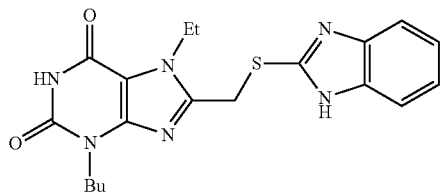 |
| --- | --- | --- |
| 23 | 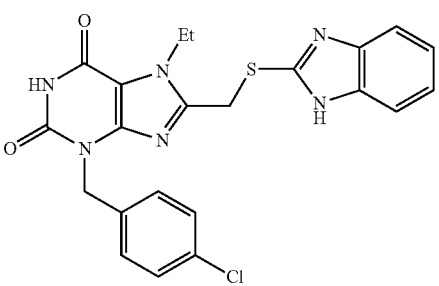 [SMILES: CCn1c(CSc2nc3ccccc3[nH]2)nc2c1c(=O)[nH]c(=O)n2Cc1ccc(Cl)cc1] | 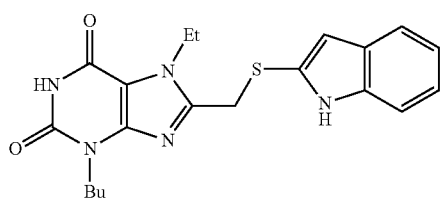 |
| 24 | 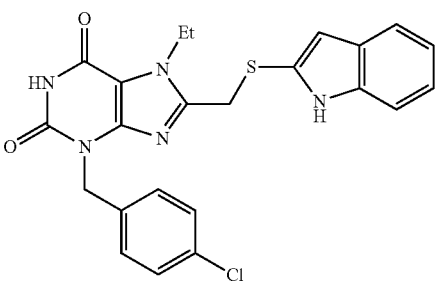 [SMILES: CCn1c(CSc2cc3ccccc3[nH]2)nc2c1c(=O)[nH]c(=O)n2Cc1ccc(Cl)cc1] | 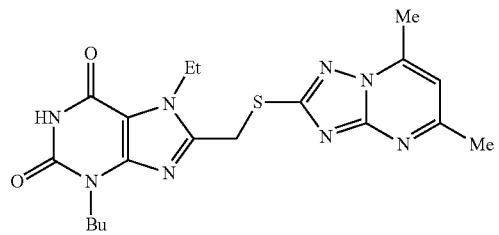 |
| 25 | 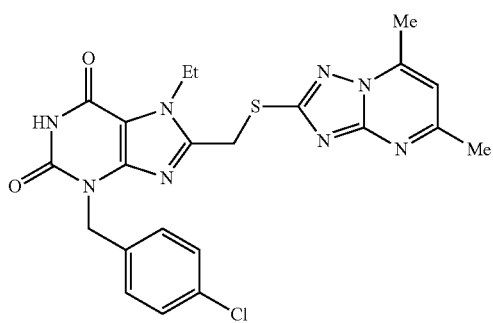 [SMILES: CCn1c(CSc2nc3nc(C)cc(C)n3n2)nc2c1c(=O)[nH]c(=O)n2Cc1ccc(Cl)cc1] | 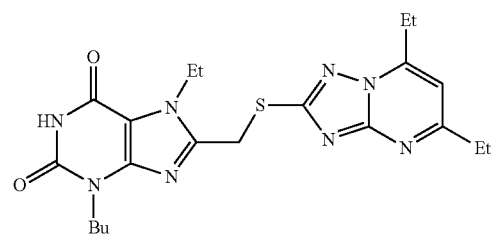 |
| 26 | 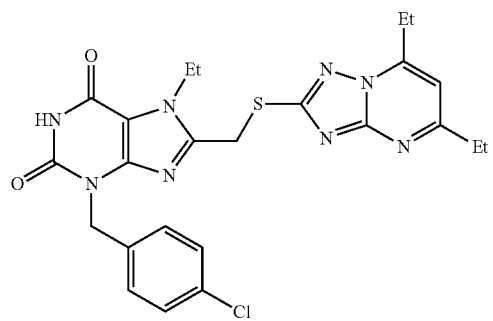 [SMILES: CCc1cc(CC)n2nc(SCc3nc4c(c(=O)[nH]c(=O)n4Cc4ccc(Cl)cc4)n3CC)nc2n1] | 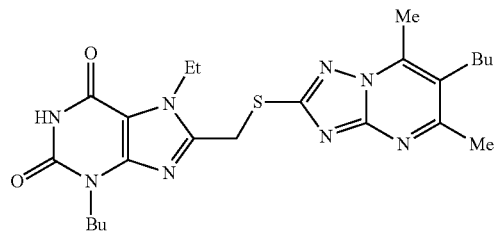 |

TABLE 1-continued
| 27 | 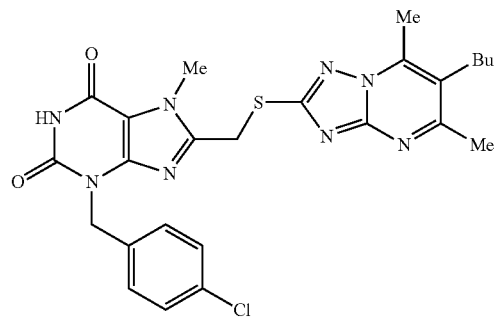 | 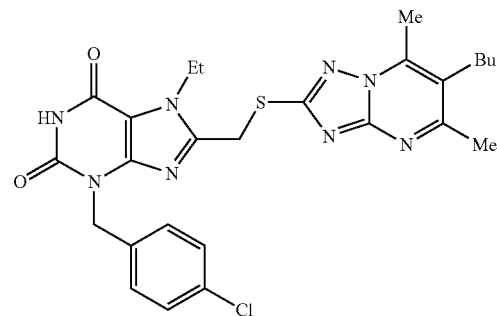 |
| --- | --- | --- |
| 28 | 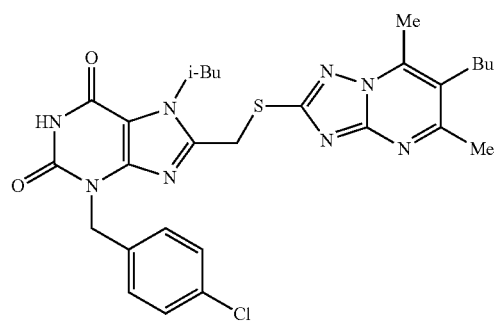 | 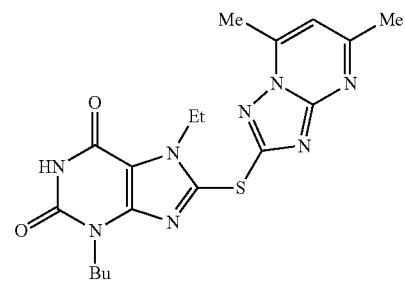 |
| 29 | 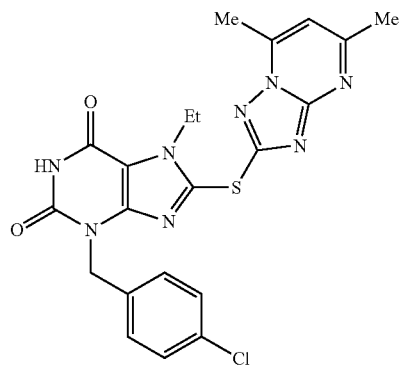 [SMILES: CCn1c(Sc2nc3nc(C)cc(C)n3n2)nc2c1c(=O)[nH]c(=O)n2Cc1ccc(Cl)cc1] | 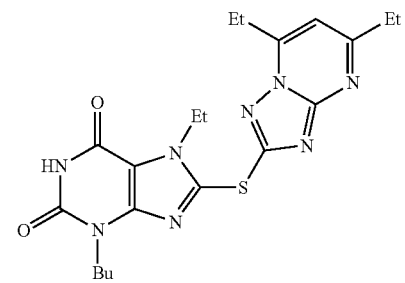 |
| 30 | 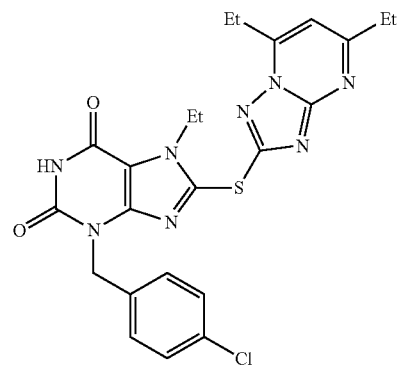 [SMILES: CCc1cc(CC)n2nc(Sc3nc4c(c(=O)[nH]c(=O)n4Cc4ccc(Cl)cc4)n3CC)nc2n1] | 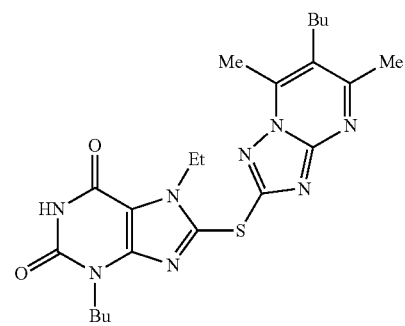 |

TABLE 1-continued
| 31 | 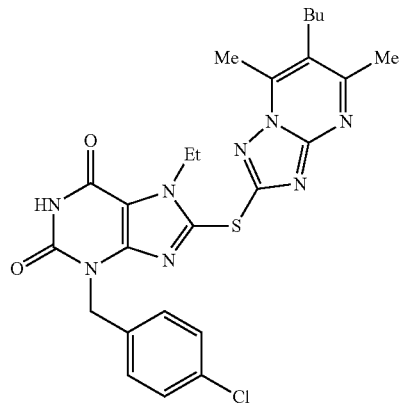 | 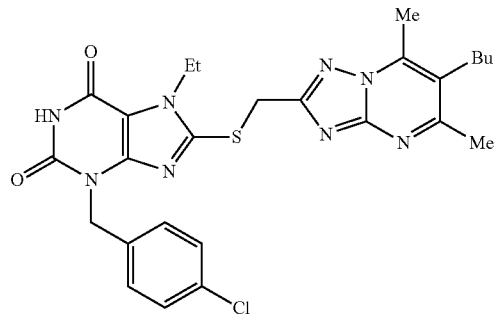 |
| 32 | 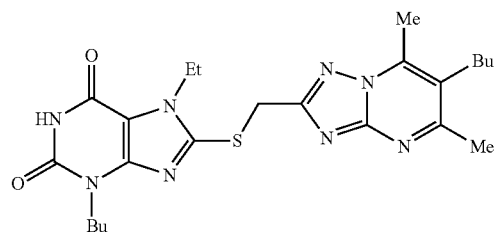 | |
| 33 | 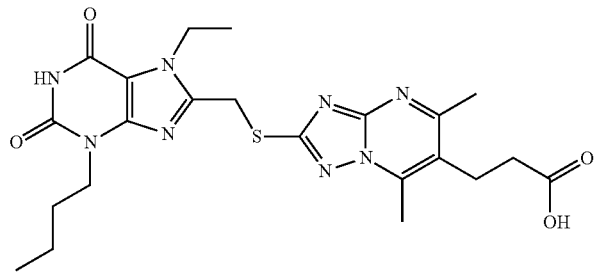 [SMILES: CCCCn1c(=O)[nH]c(=O)c2c1nc(CSc1nc3nc(C)c(CCC(=O)O)c(C)n3n1)n2CC] | |
| 34 | 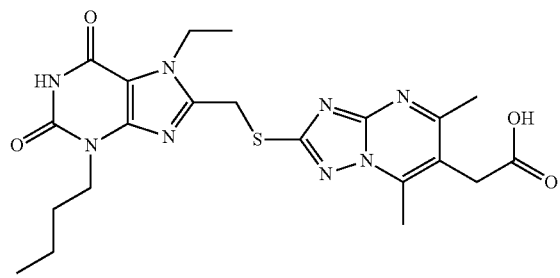 [SMILES: CCCCn1c(=O)[nH]c(=O)c2c1nc(CSc1nc3nc(C)c(CC(=O)O)c(C)n3n1)n2CC] | |
| 35 | 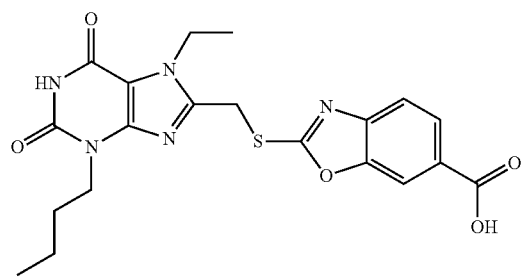 [SMILES: CCCCn1c(=O)[nH]c(=O)c2c1nc(CSc1nc3ccc(C(=O)O)cc3o1)n2CC] | |

TABLE 1-continued
36
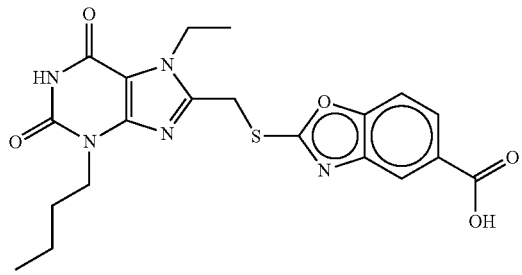
37
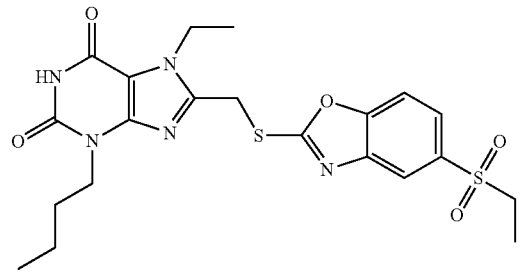 [SMILES: CCCCn1c(=O)[nH]c(=O)c2c1nc(CSc1nc3cc(S(=O)(=O)CC)ccc3o1)n2CC]
38
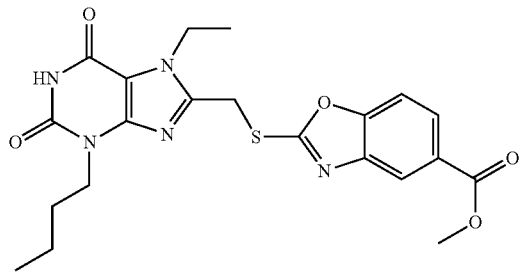 [SMILES: CCCCn1c(=O)[nH]c(=O)c2c1nc(CSc1nc3cc(C(=O)OC)ccc3o1)n2CC]
39
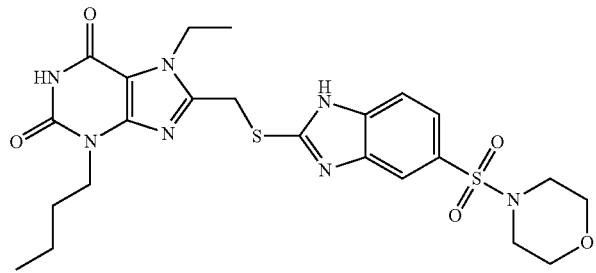 [SMILES: CCCCn1c(=O)[nH]c(=O)c2c1nc(CSc1nc3cc(S(=O)(=O)N4CCOCC4)ccc3[nH]1)n2CC]
40
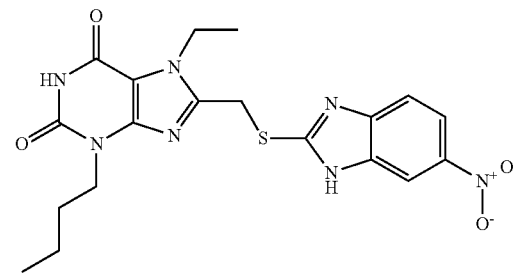

TABLE 1-continued
| 41 | 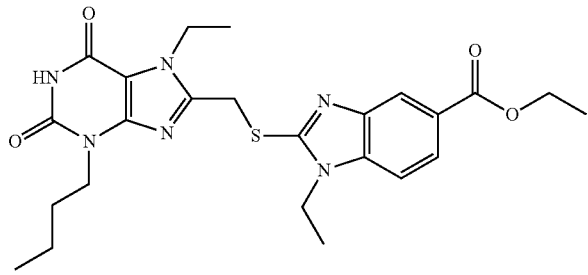 [SMILES: CCCCn1c(=O)[nH]c(=O)c2c1nc(CSc1nc3cc(C(=O)OCC)ccc3n1CC)n2CC] |
| 42 | 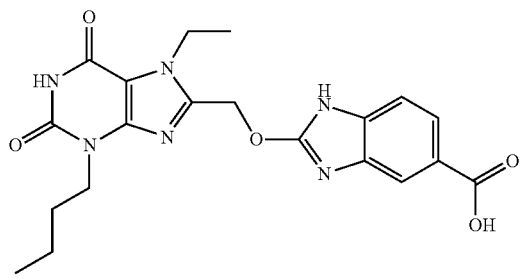 [SMILES: CCCCn1c(=O)[nH]c(=O)c2c1nc(COc1nc3cc(C(=O)O)ccc3[nH]1)n2CC] |
| 43 | 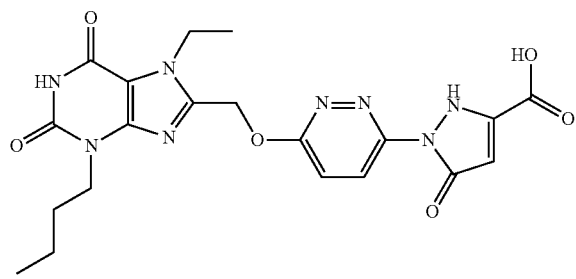 [SMILES: CCCCn1c(=O)[nH]c(=O)c2c1nc(COc1ccc(-n3[nH]c(C(=O)O)cc3=O)nn1)n2CC] |
| 44 | 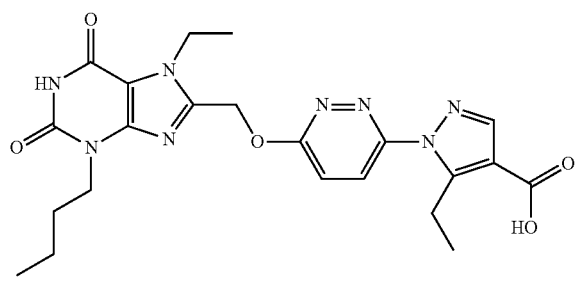 [SMILES: CCCCn1c(=O)[nH]c(=O)c2c1nc(COc1ccc(-n3ncc(C(=O)O)c3CC)nn1)n2CC] |
| 45 | 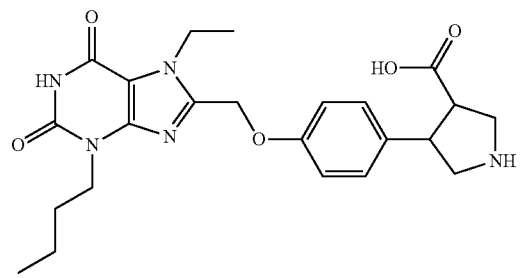 [SMILES: CCCCn1c(=O)[nH]c(=O)c2c1nc(COc1ccc(C3CNCC3C(=O)O)cc1)n2CC] |

TABLE 1-continued
46 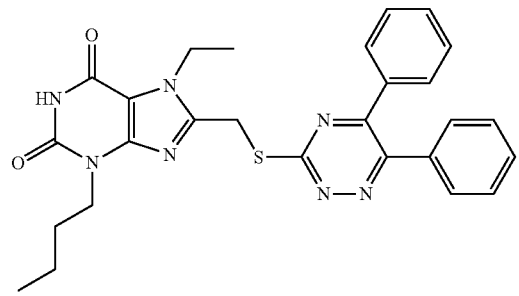 [SMILES: CCCCn1c(=O)[nH]c(=O)c2c1nc(CSc1nnc(-c3ccccc3)c(-c3ccccc3)n1)n2CC]
47 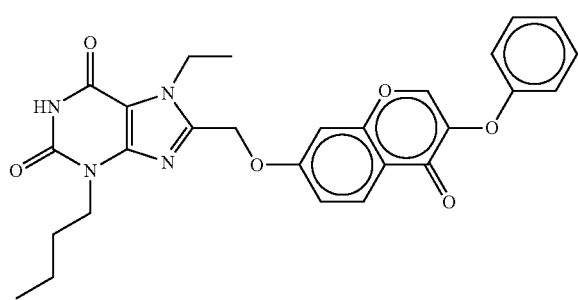
48 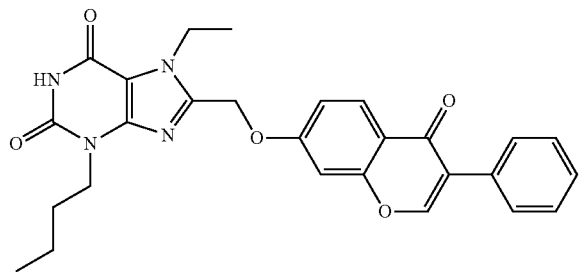 [SMILES: CCCCn1c(=O)[nH]c(=O)c2c1nc(COc1ccc3c(=O)c(-c4ccccc4)coc3c1)n2CC]
49 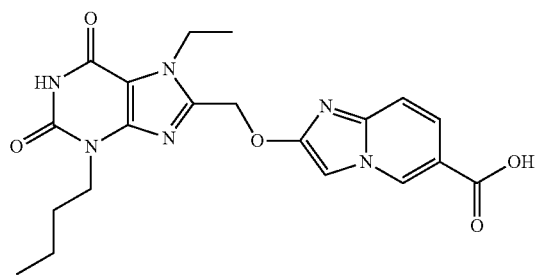 [SMILES: CCCCn1c(=O)[nH]c(=O)c2c1nc(COc1cn3cc(C(=O)O)ccc3n1)n2CC]
50 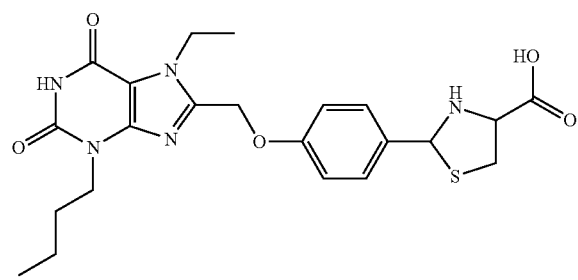 [SMILES: CCCCn1c(=O)[nH]c(=O)c2c1nc(COc1ccc(C3NC(C(=O)O)CS3)cc1)n2CC]

TABLE 1-continued
| | |
|---|---|
| 51 | 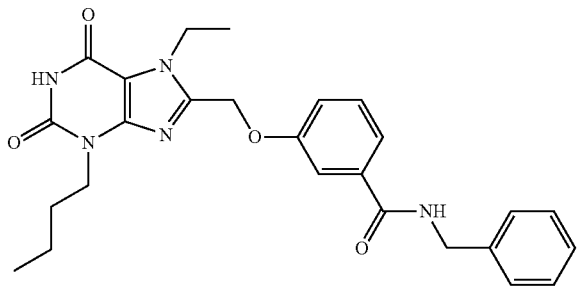 [SMILES: CCCCn1c(=O)[nH]c(=O)c2c1nc(COc1cccc(C(=O)NCc3ccccc3)c1)n2CC] |
| 52 | 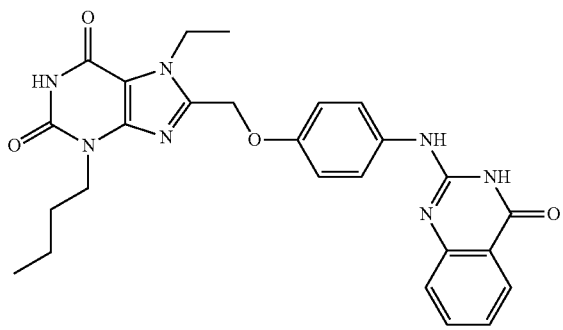 [SMILES: CCCCn1c(=O)[nH]c(=O)c2c1nc(COc1ccc(Nc3nc4ccccc4c(=O)[nH]3)cc1)n2CC] |
| 53 | 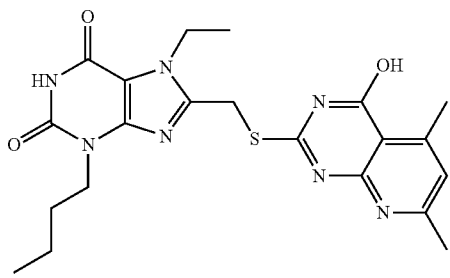 [SMILES: CCCCn1c(=O)[nH]c(=O)c2c1nc(CSc1nc(O)c3c(C)cc(C)nc3n1)n2CC] |
| 54 | 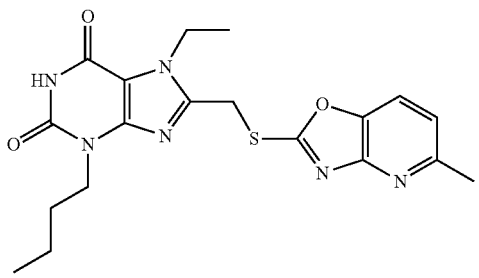 [SMILES: CCCCn1c(=O)[nH]c(=O)c2c1nc(CSc1nc3nc(C)ccc3o1)n2CC] |
| 55 | 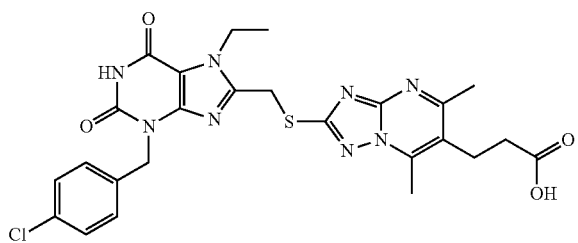 [SMILES: CCn1c(CSc2nc3nc(C)c(CCC(=O)O)c(C)n3n2)nc2c1c(=O)[nH]c(=O)n2Cc1ccc(Cl)cc1] |

TABLE 1-continued
56 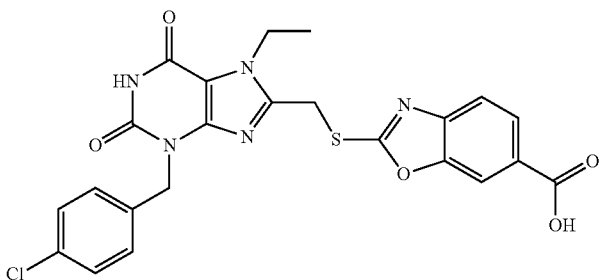 [SMILES: CCn1c(CSc2nc3ccc(C(=O)O)cc3o2)nc2c1c(=O)[nH]c(=O)n2Cc1ccc(Cl)cc1]
57 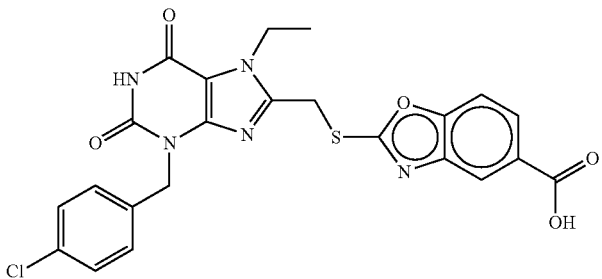
58 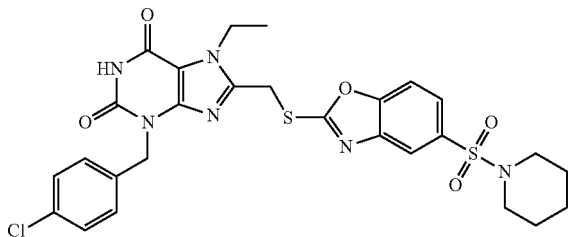 [SMILES: CCn1c(CSc2nc3cc(S(=O)(=O)N4CCCCC4)ccc3o2)nc2c1c(=O)[nH]c(=O)n2Cc1ccc(Cl)cc1]
59 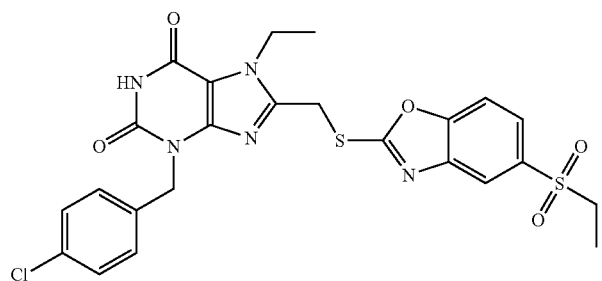 [SMILES: CCn1c(CSc2nc3cc(S(=O)(=O)CC)ccc3o2)nc2c1c(=O)[nH]c(=O)n2Cc1ccc(Cl)cc1]
60 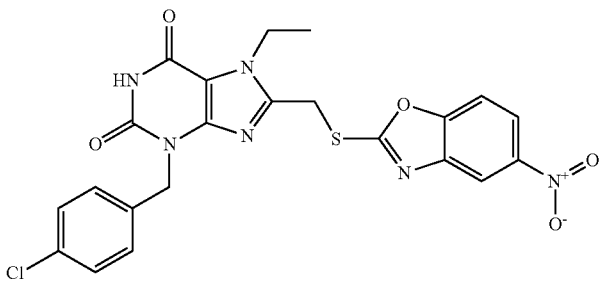 [SMILES: CCn1c(CSc2nc3cc([N+](=O)[O-])ccc3o2)nc2c1c(=O)[nH]c(=O)n2Cc1ccc(Cl)cc1]
61 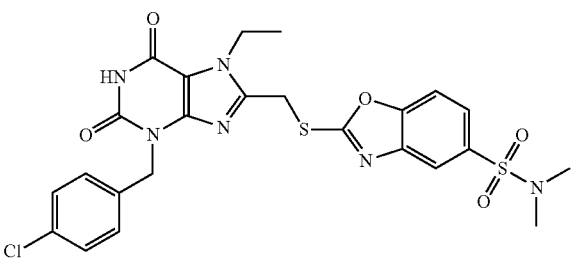 [SMILES: CCn1c(CSc2nc3cc(S(=O)(=O)N(C)C)ccc3o2)nc2c1c(=O)[nH]c(=O)n2Cc1ccc(Cl)cc1]

TABLE 1-continued
62
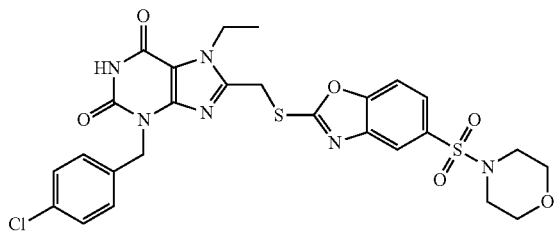 [SMILES: CCn1c(CSc2nc3cc(S(=O)(=O)N4CCOCC4)ccc3o2)nc2c1c(=O)[nH]c(=O)n2Cc1ccc(Cl)cc1]
63
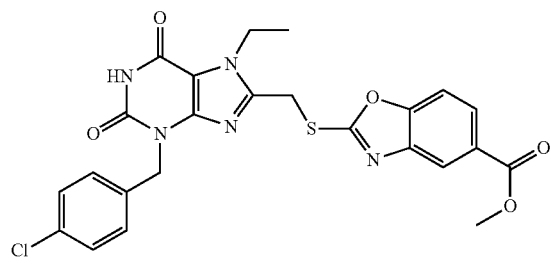 [SMILES: CCn1c(CSc2nc3cc(C(=O)OC)ccc3o2)nc2c1c(=O)[nH]c(=O)n2Cc1ccc(Cl)cc1]
64
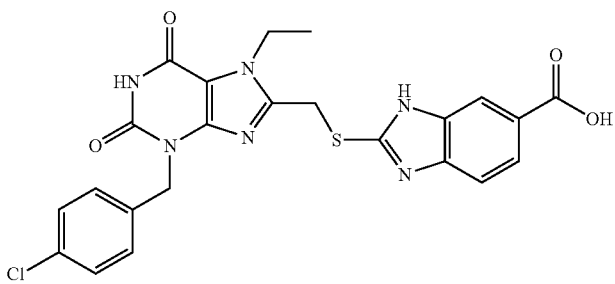 [SMILES: CCn1c(CSc2nc3ccc(C(=O)O)cc3[nH]2)nc2c1c(=O)[nH]c(=O)n2Cc1ccc(Cl)cc1]
65
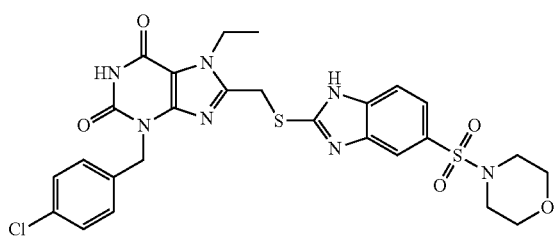 [SMILES: CCn1c(CSc2nc3cc(S(=O)(=O)N4CCOCC4)ccc3[nH]2)nc2c1c(=O)[nH]c(=O)n2Cc1ccc(Cl)cc1]
66
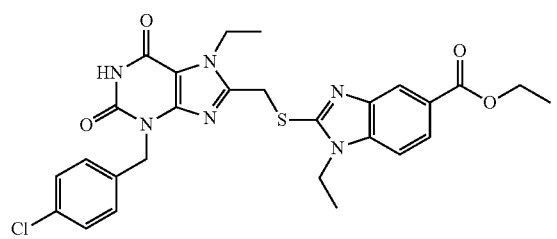 [SMILES: CCOC(=O)c1ccc2c(c1)nc(SCc1nc3c(c(=O)[nH]c(=O)n3Cc3ccc(Cl)cc3)n1CC)n2CC]
67
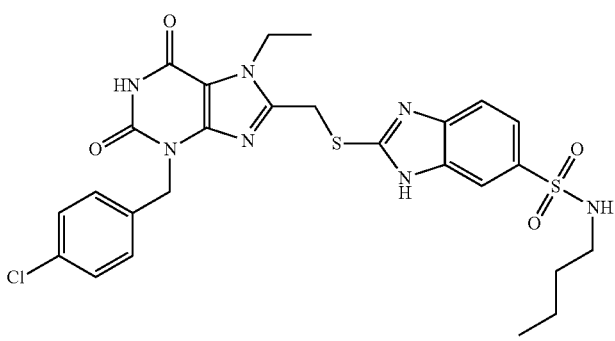 [SMILES: CCCCNS(=O)(=O)c1ccc2nc(SCc3nc4c(c(=O)[nH]c(=O)n4Cc4ccc(Cl)cc4)n3CC)[nH]c2c1]

TABLE 1-continued
68 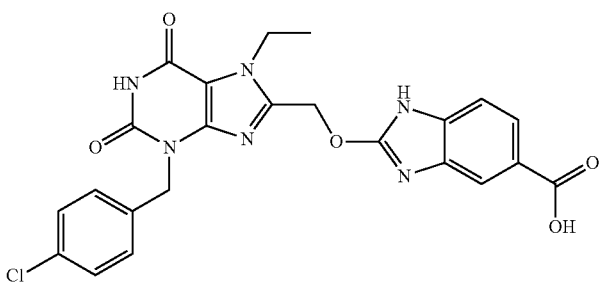 [SMILES: CCn1c(COc2nc3cc(C(=O)O)ccc3[nH]2)nc2c1c(=O)[nH]c(=O)n2Cc1ccc(Cl)cc1]
69 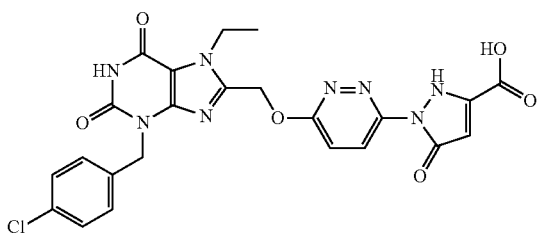
70 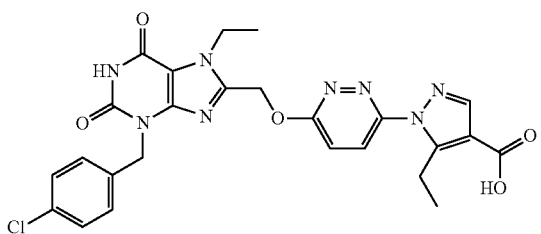 [SMILES: CCc1c(C(=O)O)cnn1-c1ccc(OCc2nc3c(c(=O)[nH]c(=O)n3Cc3ccc(Cl)cc3)n2CC)nn1]
71 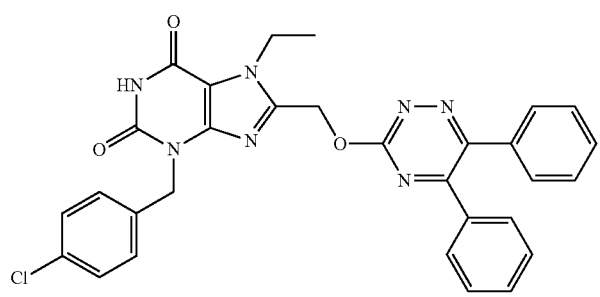 [SMILES: CCn1c(COc2nnc(-c3ccccc3)c(-c3ccccc3)n2)nc2c1c(=O)[nH]c(=O)n2Cc1ccc(Cl)cc1]
72 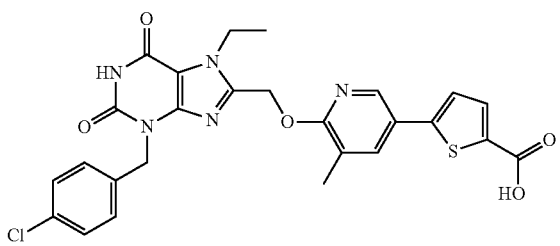 [SMILES: CCn1c(COc2ncc(-c3ccc(C(=O)O)s3)cc2C)nc2c1c(=O)[nH]c(=O)n2Cc1ccc(Cl)cc1]
73 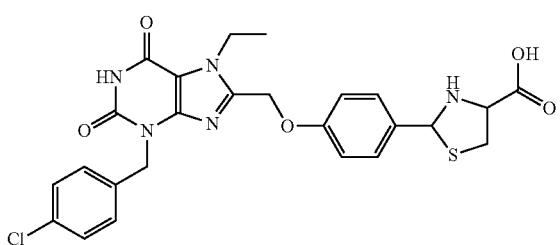 [SMILES: CCn1c(COc2ccc(C3NC(C(=O)O)CS3)cc2)nc2c1c(=O)[nH]c(=O)n2Cc1ccc(Cl)cc1]

TABLE 1-continued
74 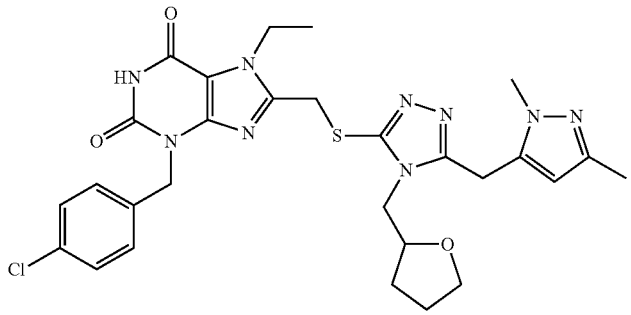 [SMILES: CCn1c(CSc2nnc(Cc3cc(C)nn3C)n2CC2CCCO2)nc2c1c(=O)[nH]c(=O)n2Cc1ccc(Cl)cc1]
75 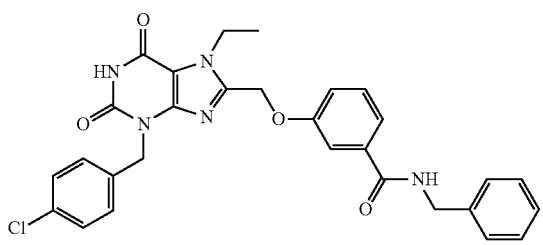 [SMILES: CCn1c(COc2cccc(C(=O)NCc3ccccc3)c2)nc2c1c(=O)[nH]c(=O)n2Cc1ccc(Cl)cc1]
76 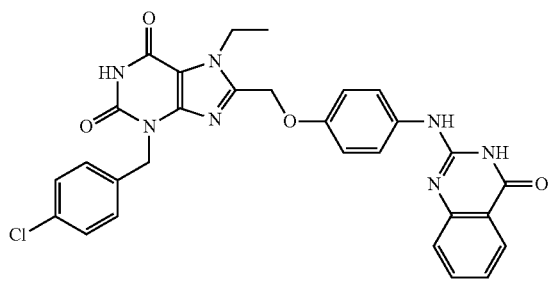 [SMILES: CCn1c(COc2ccc(Nc3nc4ccccc4c(=O)[nH]3)cc2)nc2c1c(=O)[nH]c(=O)n2Cc1ccc(Cl)cc1]
77 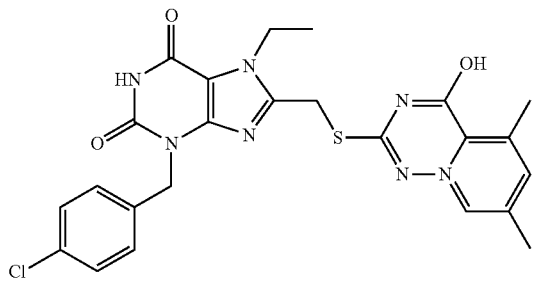
78 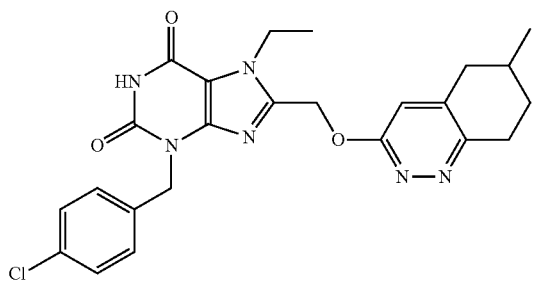 [SMILES: CCn1c(COc2cc3c(nn2)CCC(C)C3)nc2c1c(=O)[nH]c(=O)n2Cc1ccc(Cl)cc1]

79

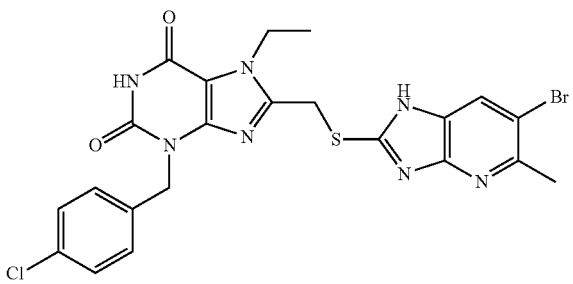 [SMILES: CCn1c(CSc2nc3nc(C)c(Br)cc3[nH]2)nc2c1c(=O)[nH]c(=O)n2Cc1ccc(Cl)cc1]

80

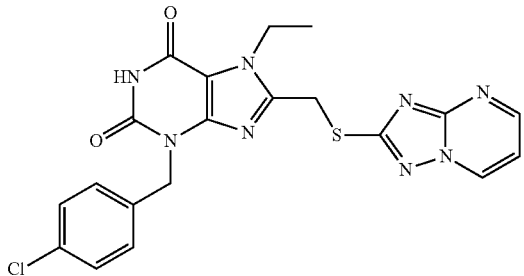 [SMILES: CCn1c(CSc2nc3ncccn3n2)nc2c1c(=O)[nH]c(=O)n2Cc1ccc(Cl)cc1]

In a particular embodiment, the inhibitor of general formula (I) is not the theobromine, not the enprofylline and not IPDX as defined in J. W. Daly, *Caffeine analogs: biomedical impact, Cellular and Molecular Life Sciences* 64 (2007) 2153-2169, nor the compounds of table A as defined in Evgeny A. Rogozin et al., *Inhibitory effects of caffeine analogues on neoplastic transformation: structure-activity relationship*.

TABLE A of Evgeny A. Rogozin et al., Inhibitory effects of caffeine analogues on neoplastic transformation: structure-activity relationship

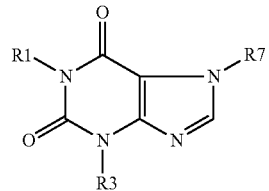

| No. | Compound name | Radical 1 | Radical 3 | Radical 7 |
|---|---|---|---|---|
| 1 | Xanthine | H | H | H |
| 2 | 1-Methylxanthine | Me | H | H |
| 3 | 3-Methylxanthine | H | Me | H |
| 4 | 7-Methylxanthine | H | H | Me |
| 5 | 1,3-Dimethylxanthine (neophylline) | Me | Me | H |
| 6 | 1,7-Dimethylxanthine (paraxanthine) | Me | H | Me |
| 7 | 3,7-Dimethylxanthine (theobromine) | H | Me | Me |
| 8 | 1,3,7-Trimethylxanthine (caffeine) | Me | Me | Me |
| 9 | 1-Ethylxanthine (Xt 101) | Et | H | H |
| 10 | 3-Ethylxanthine (NY 457) | H | Et | H |
| 11 | 1-Ethyl-3-methylxanthine (Xt 054) | Et | Me | H |
| 12 | 1,3-Ethylxanthine (Xt 023) | Et | Et | H |
| 13 | 1-Propylxanthine (Xt 102) | n-Pro | H | H |
| 14 | 3-Propylxanthine (caprolylline) | H | n-Pro | H |
| 15 | 1-Proplyl-3-methylxanthine (Xt 055) | n-Pro | Me | H |
| 16 | 3-Proplyl-7-methylxanthine (Xt 016) | H | n-Pro | Me |
| 17 | 1,7-Dimethyl-3-propylxanthine (Xt 017) | Me | n-Pro | Me |
| 18 | 1-Propyl-3-ethylxanthine (Xt 059) | n-Pro | Et | H |
| 19 | 1-Ethyl-3-propylxanthine (Xt 015) | Et | n-Pro | H |
| 20 | 3-Propyl-7-ethylxanthine (Xt 018) | H | n-Pro | Et |
| 21 | 1-Methyl-3-propyl-7-ethylxanthine (Xt 074) | Me | n-Pro | Et |
| 22 | 1-Ethyl-3-propyl-7-methylxanthine (Xt 071) | Et | n-Pro | Me |
| 23 | 1,3-Dipropylxanthine (Xt 043) | n-Pro | n-Pro | H |
| 24 | 3,7-Dipropylxanthine (Xt 019) | H | n-Pro | n-Pro |
| 25 | 1,3-Dipropylxanthine (Xt 072) | n-Pro | n-Pro | Me |
| 26 | 1-Methyl-3,7-dipropylxanthine (Xt 075) | Me | n-Pro | n-Pro |
| 27 | 1-Butylxanthine (Xt 103) | n-Bu | H | H |
| 28 | 3-Butylxanthine (Xt 466) | H | n-Bu | H |
| 29 | 1-Butyl-3-methylxanthine (Xt 056) | n-Bu | Me | H |
| 30 | 1-Methyl-3-butylxanthine (Xt 011) | Me | n-Bu | H |
| 31 | 1-Butyl-3-ethylxanthine (Xt 060) | n-Bu | Et | H |
| 32 | 1-Ethyl-3-butylxanthine (Xt 031) | Et | n-Bu | H |
| 33 | 1-Propyl-3-butylxanthine (Xt 047) | n-Pro | n-Bu | H |
| 34 | 1-Butyl-3-propyl-7-butylxanthine (Xt 073) | n-Bu | n-Pro | Me |
| 35 | 1-Methyl-3-propyl-7-butylxanthine (Xt 077) | Me | n-Pro | n-Bu |
| 36 | 1,3-Dibutylxanthine (Xt 048) | n-Bu | n-Bu | H |
| 37 | 1-Pentylxanthine (Xt 104) | n-Pent | H | H |
| 38 | 1-Pentyl-3-methylxanthine (Xt 057) | n-Pent | Me | H |
| 39 | 1-Pentyl-3-ethylxanthine (Xt 061) | n-Pent | Et | H |
| 40 | 1-Ethyl-3-pentylxanthine (Xt 066) | Et | n-Pent | H |
| 41 | 1-Pentyl-3-propyl-7-methylxanthine (Xt 078) | n-Pent | n-Pro | Me |
| 42 | 1-Pentyl-3-butylxanthine (Xt 049) | n-Pent | n-Bu | H |
| 43 | 1-Hexylxanthine (Xt 105) | n-Hex | H | H |
| 44 | 3-Hexylxanthine (Xt 040) | H | n-Hex | H |
| 45 | 1-Hexyl-3-methylxanthine (Xt 058) | n-Hex | Me | H |
| 46 | 1-Methyl-3-hexylxanthine (Xt 069) | Me | n-Hex | H |
| 47 | 1-Hexyl-3-ethylxanthine (Xt 062) | n-Hex | Et | H |
| 48 | 1-Ethyl-3-hexylxanthine (Xt 070) | Et | n-Hex | H |
| 49 | 1-Hexyl-3-propyl-7-methylxanthine (Xt 079) | n-Hex | n-Pro | Me |
| 50 | 1-Hexyl-3-butylxanthine (Xt 050) | n-Hex | n-Bu | H |

According to one embodiment, the inhibitor of general formula (I) as defined above inhibits at least one bromodomain BD1 or BD2 of a BET protein selected from BRD2, BRD3, BRD4 and BRDT.

BRD4 Inhibitors

According to another embodiment, the inhibitor of general formula (I) as defined above inhibits the BRD4 protein, wherein said inhibitor binds to BD1 of BRD4, and wherein said inhibitor has an IC$_{50}$ for BRD4 (BD1) equal to or less than 50 µM, and wherein:
X represents an oxygen atom;
Y represents an oxygen atom, an amino group, NHR$_o$, or a linker-ligand for the E3 ubiquitin ligase; wherein R$_o$ represents —C(O)OR$_p$ wherein R$_p$ represents a C$_1$-C$_4$ alkyl;
R$_1$ represents a hydrogen atom or a lone pair;
R$_3$ represents a C$_1$-C$_6$ alkyl, preferably a C$_1$-C$_4$ alkyl, a linker-ligand for the E3 ubiquitin ligase, or a (C$_5$-C$_{12}$)aryl-(C$_1$-C$_6$)alkyl, optionally substituted by:
a halogen atom, or
a C$_1$-C$_4$ alkyl;
R$_7$ represents a C$_1$-C$_6$ alkyl, preferably a C$_1$-C$_4$ alkyl and even more preferably a methyl or ethyl group;
R$_8$ represents a hydrogen atom, —SH, —SR$_q$—, —CH$_2$—O—R$_q$ or —CH$_2$—S—R$_q$;
wherein R$_q$ represents a heteroaryl, optionally substituted by one or more:
C$_1$-C$_6$ alkyl, preferably a C$_1$-C$_4$ alkyl,
amino groups,
halogen atoms,
(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid,
ketone groups,
pyrazole optionally substituted by one or more (C$_1$-C$_4$) alkanoic acid or (C$_1$-C$_4$)alkyl,
pyrrolidine optionally substituted by one or more (C$_1$-C$_4$)alkanoic acid,
phenyl,
benzyl,
oxy-phenyl,
oxy-benzyl,
thiazolidin optionally substituted by one or more (C$_1$-C$_4$)alkanoic acid,
—C(=O)—N(H)-benzyl,
—N(H)-quinazolinone,
—OH,
thiophenyl optionally substituted by one or more (C$_1$-C$_4$)alkanoic acid,
methyl-tetrahydrofuran, or
—CH$_2$-pyrazole optionally substituted by one or more (C$_1$-C$_4$) alkyl;
or an aryl, optionally substituted by one or more;
C$_1$-C$_6$ alkyl, preferably a C$_1$-C$_4$ alkyl,
amino groups,
halogen atoms,
(C$_1$-C$_4$)alkanoic acid,
—S(O$_2$)—(C$_1$-C$_4$)alkyl,
—S(O$_2$)-piperidine,
—S(O$_2$)—(N,N)dimethylamine,
—S(O$_2$)-morpholine,
nitro groups,
—C(=O)—O—(C$_1$-C$_4$)alkyl,
—S(O$_2$)—N(H)—(C$_1$-C$_4$)alkyl,
oxo-pyrazole optionally substituted by one or more (C$_1$-C$_4$)alkanoic acid,
ketone groups,
pyrazole optionally substituted by one or more (C$_1$-C$_4$) alkanoic acid or (C$_1$-C$_4$)alkyl,
pyrrolidine optionally substituted by one or more (C$_1$-C$_4$)alkanoic acid,
phenyl,
benzyl,
oxy-phenyl,
oxy-benzyl,
thiazolidin optionally substituted by one or more (C$_1$-C$_4$)alkanoic acid,
—C(=O)—N(H)-benzyl,
—N(H)-quinazolinone,
—OH,
thiophenyl optionally substituted by one or more (C$_1$-C$_4$)alkanoic acid,
methyl-tetrahydrofuran, or
—CH$_2$-pyrazole optionally substituted by one or more (C$_1$-C$_4$) alkyl.

In a preferred embodiment, X, Y, R$_1$, R$_3$ and R$_7$ are as defined above and R$_8$ represents a hydrogen atom, —SH, —SR$_r$, —CH$_2$—O—R$_r$ or —CH$_2$—S—R$_r$;
wherein R$_r$ represents one of the following groups optionally substituted by one or more C$_1$-C$_6$ alkyl, preferably C$_1$-C$_4$ alkyl, amino groups, halogen atoms, (C$_1$-C$_4$) alkanoic acid, —S(O$_2$)—(C$_1$-C$_4$)alkyl, —S(O$_2$)-piperidine, —S(O$_2$)—(N,N)dimethylamine, —S(O$_2$)-morpholine, nitro groups, —C(=O)—O—(C$_1$-C$_4$)alkyl, —S(O$_2$)—N(H)—(C$_1$-C$_4$)alkyl, oxo-pyrazole optionally substituted by one or more (C$_1$-C$_4$)alkanoic acid, pyrazole optionally substituted by one or more (C$_1$-C$_4$) alkanoic acid or (C$_1$-C$_4$)alkyl, phenyl, oxy-phenyl, pyrrolidine optionally substituted by one or more (C$_1$-C$_4$)alkanoic acid, thiazolidin optionally substituted by one or more (C$_1$-C$_4$)alkanoic acid, —C(=O)—N(H)-benzyl, —N(H)-quinazolinone, —OH, thiophenyl optionally substituted by one or more (C$_1$-C$_4$)alkanoic acid,
methyl-tetrahydrofuran or —CH$_2$-pyrazole optionally substituted by one or more (C$_1$-C$_4$) alkyl:

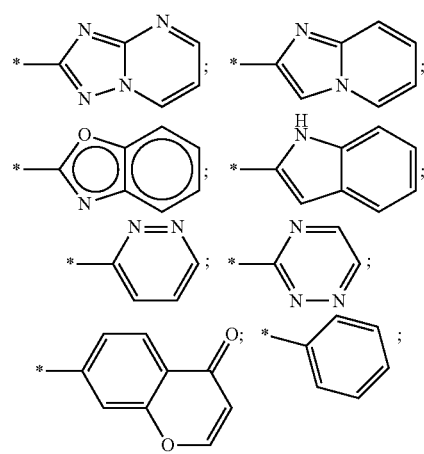

-continued

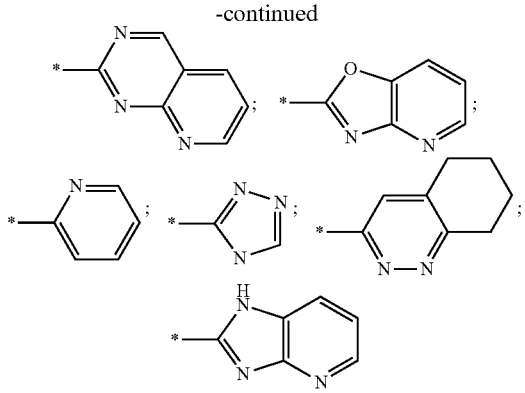

wherein * is the linking point to the sulfur atom or oxygen atom.

In a preferred embodiment, $R_1$, $R_3$, $R_7$, $R_8$ and Y are as defined above and X is an oxygen atom.

In a preferred embodiment, $R_3$, $R_7$, $R_8$, X and Y are as defined above and $R_1$ is a hydrogen atom or a lone pair.

In a preferred embodiment, $R_1$, $R_3$, $R_8$, X and Y are as defined above and $R_7$ is a methyl or ethyl group.

In a preferred embodiment, $R_1$, $R_7$, $R_8$, X and Y are as defined above and $R_3$ is a para-halogenobenzyl, a butyl, a benzyl or a para-($C_1$-$C_4$ alkyl)benzyl.

In a preferred embodiment, $R_1$, $R_7$, $R_8$, X and Y are as defined above and $R_3$ is a para-chlorobenzyl, a para-bromobenzyl, a para-(t-Bu)benzyl, a benzyl or a butyl.

Preferably, the inhibitor of BRD4 (BD1) protein is selected from the group consisting of:

| | a | B | c |
|---|---|---|---|
| 4 | | 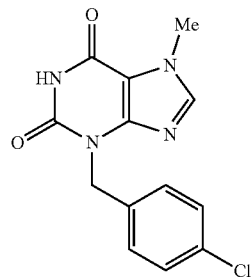 | |
| 6 | 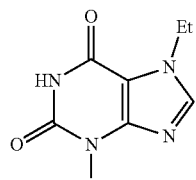 | 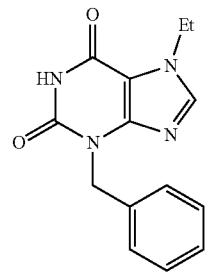 | 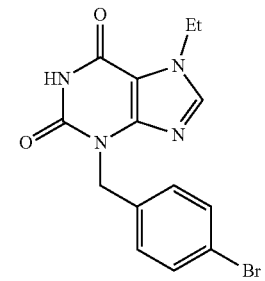 [SMILES: CCn1cnc2c1c(=O)[nH]c(=O)n2Cc1ccc(Br)cc1] |
| 7 | 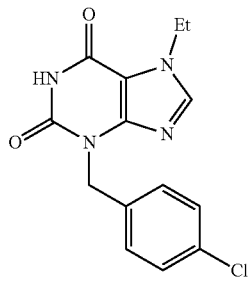 [SMILES: CCn1cnc2c1c(=O)[nH]c(=O)n2Cc1ccc(Cl)cc1] | 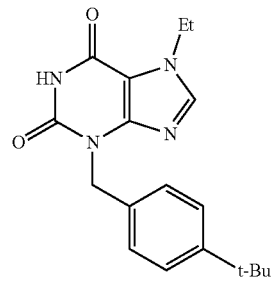 | 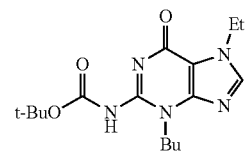 |
| 8 | | | 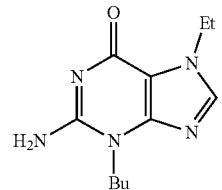 |

-continued
| | a | b |
|---|---|---|
| 15 | 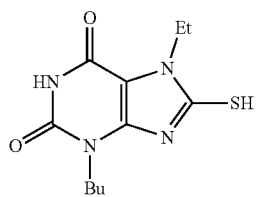 | |
| 21 | 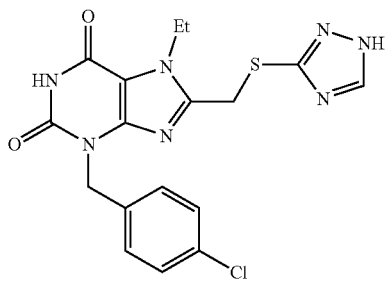 [SMILES: CCn1c(CSc2nc[nH]n2)nc2c1c(=O)[nH]c(=O)n2Cc1ccc(Cl)cc1] | |
| 22 | 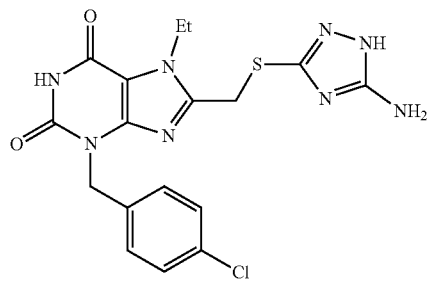 [SMILES: CCn1c(CSc2n[nH]c(N)n2)nc2c1c(=O)[nH]c(=O)n2Cc1ccc(Cl)cc1] | |
| 25 | 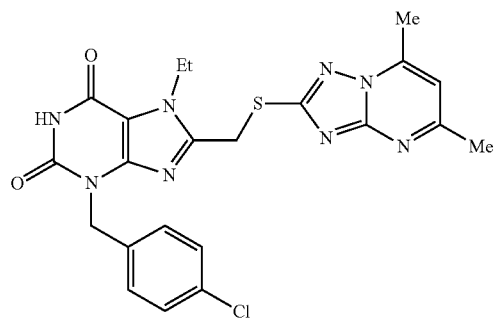 [SMILES: CCn1c(CSc2nc3nc(C)cc(C)n3n2)nc2c1c(=O)[nH]c(=O)n2Cc1ccc(Cl)cc1] | 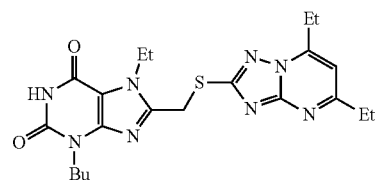 |
| 26 | 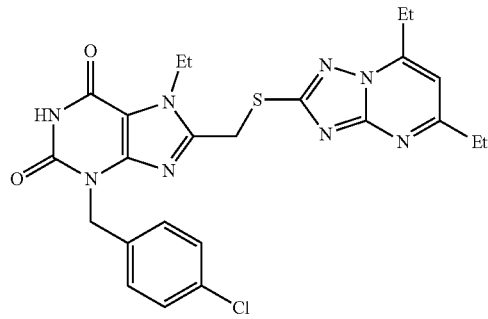 [SMILES: CCc1cc(CC)n2nc(SCc3nc4c(c(=O)[nH]c(=O)n4Cc4ccc(Cl)cc4)n3CC)nc2n1] | 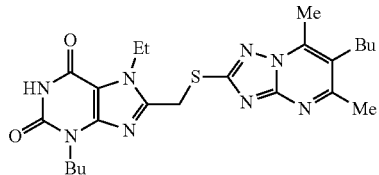 |

-continued
27  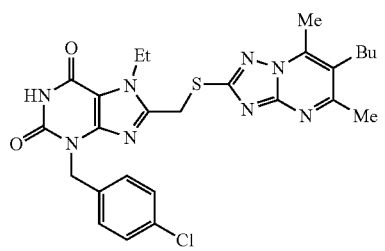
30  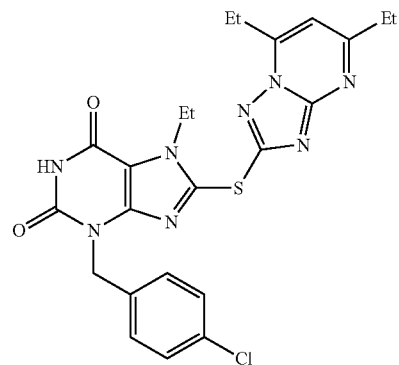 [SMILES: CCc1cc(CC)n2nc(Sc3nc4c(c(=O)[nH]c(=O)n4Cc4ccc(Cl)cc4)n3CC)nc2n1]
31  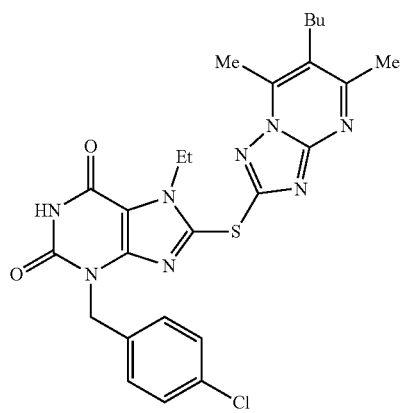
33  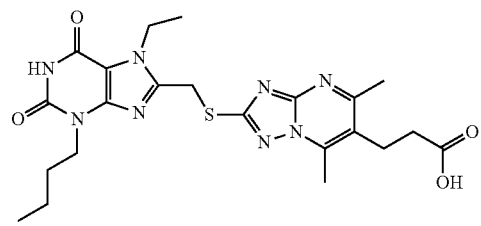 [SMILES: CCCCn1c(=O)[nH]c(=O)c2c1nc(CSc1nc3nc(C)c(CCC(=O)O)c(C)n3n1)n2CC]
34  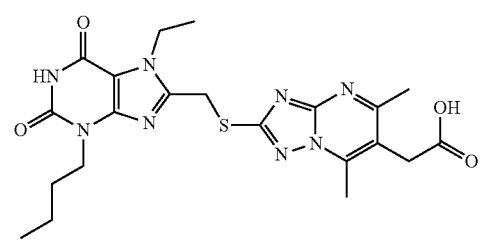 [SMILES: CCCCn1c(=O)[nH]c(=O)c2c1nc(CSc1nc3nc(C)c(CC(=O)O)c(C)n3n1)n2CC]

-continued
35 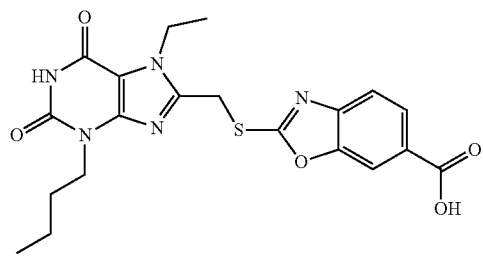 [SMILES: CCCCn1c(=O)[nH]c(=O)c2c1nc(CSc1nc3ccc(C(=O)O)cc3o1)n2CC]
36 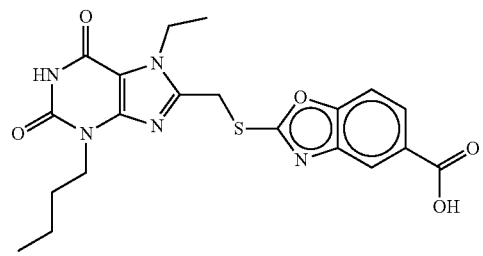
37 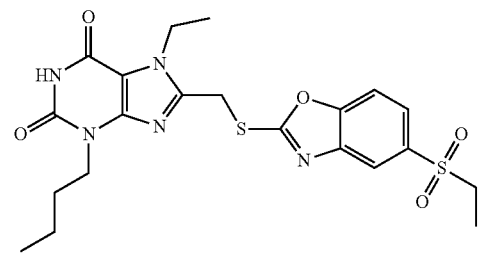 [SMILES: CCCCn1c(=O)[nH]c(=O)c2c1nc(CSc1nc3cc(S(=O)(=O)CC)ccc3o1)n2CC]
38 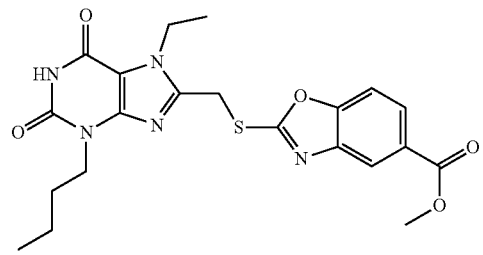 [SMILES: CCCCn1c(=O)[nH]c(=O)c2c1nc(CSc1nc3cc(C(=O)OC)ccc3o1)n2CC]
39 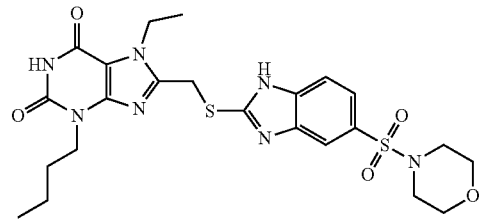 [SMILES: CCCCn1c(=O)[nH]c(=O)c2c1nc(CSc1nc3cc(S(=O)(=O)N4CCOCC4)ccc3[nH]1)n2CC]
40 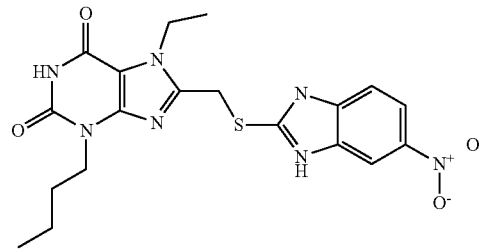

-continued
41
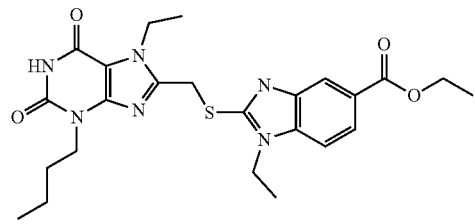
42
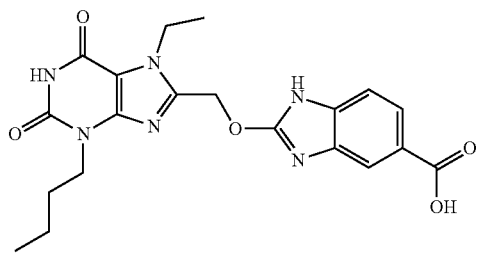 [SMILES: CCCCn1c(=O)[nH]c(=O)c2c1nc(COc1nc3cc(C(=O)O)ccc3[nH]1)n2CC]
43
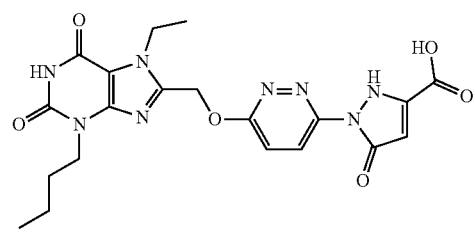 [SMILES: CCCCn1c(=O)[nH]c(=O)c2c1nc(COc1ccc(-n3[nH]c(C(=O)O)cc3=O)nn1)n2CC]
44
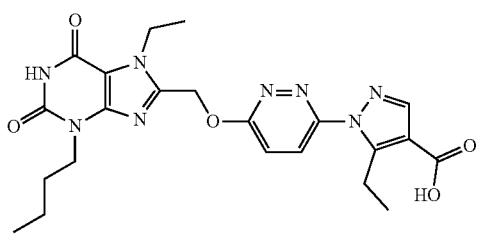 [SMILES: CCCCn1c(=O)[nH]c(=O)c2c1nc(COc1ccc(-n3ncc(C(=O)O)c3CC)nn1)n2CC]
45
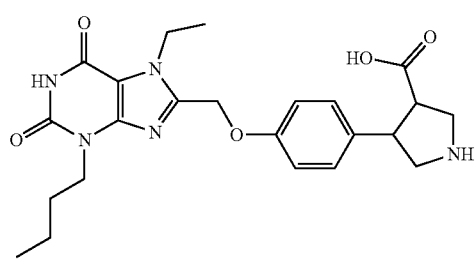 [SMILES: CCCCn1c(=O)[nH]c(=O)c2c1nc(COc1ccc(C3CNCC3C(=O)O)cc1)n2CC]
46
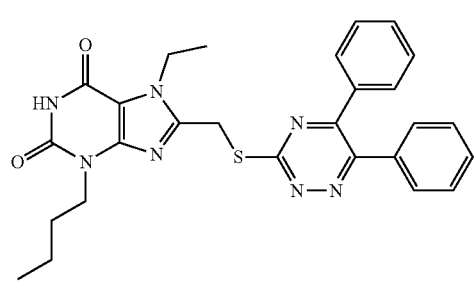 [SMILES: CCCCn1c(=O)[nH]c(=O)c2c1nc(CSc1nnc(-c3ccccc3)c(-c3ccccc3)n1)n2CC]

-continued
| 47 | 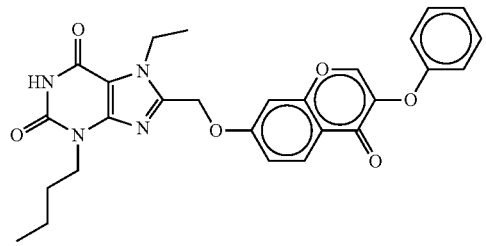 |
| 48 | 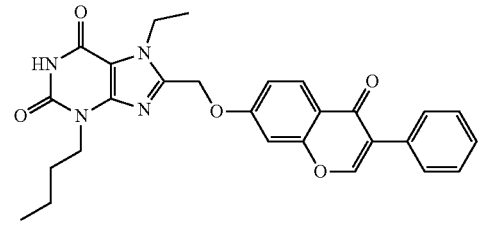 [SMILES: CCCCn1c(=O)[nH]c(=O)c2c1nc(COc1ccc3c(=O)c(-c4ccccc4)coc3c1)n2CC] |
| 49 | 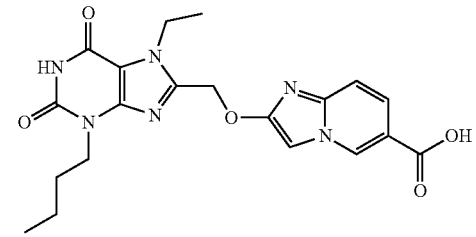 [SMILES: CCCCn1c(=O)[nH]c(=O)c2c1nc(COc1cn3cc(C(=O)O)ccc3n1)n2CC] |
| 50 | 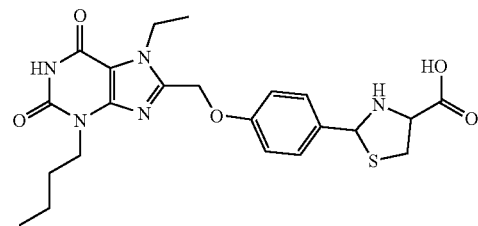 [SMILES: CCCCn1c(=O)[nH]c(=O)c2c1nc(COc1ccc(C3NC(C(=O)O)CS3)cc1)n2CC] |
| 51 | 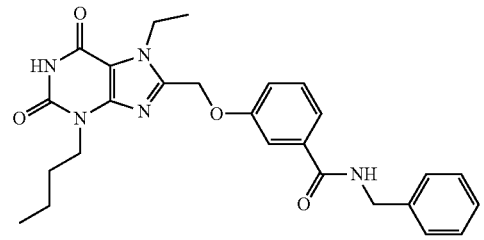 [SMILES: CCCCn1c(=O)[nH]c(=O)c2c1nc(COc1cccc(C(=O)NCc3ccccc3)c1)n2CC] |
| 52 | 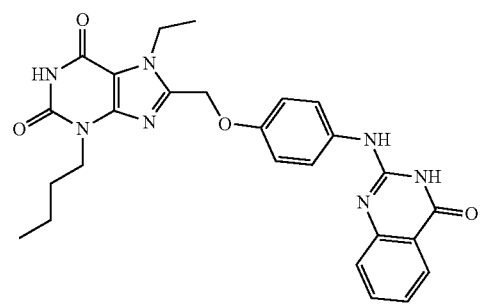 [SMILES: CCCCn1c(=O)[nH]c(=O)c2c1nc(COc1ccc(Nc3nc4ccccc4c(=O)[nH]3)cc1)n2CC] |

-continued
| 53 | 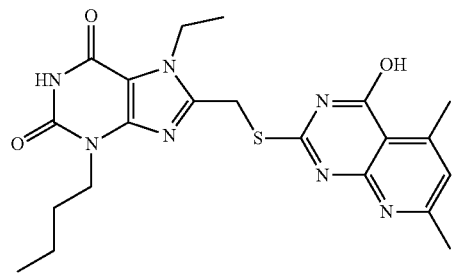 [SMILES: CCCCn1c(=O)[nH]c(=O)c2c1nc(CSc1nc(O)c3c(C)cc(C)nc3n1)n2CC] |
| 54 | 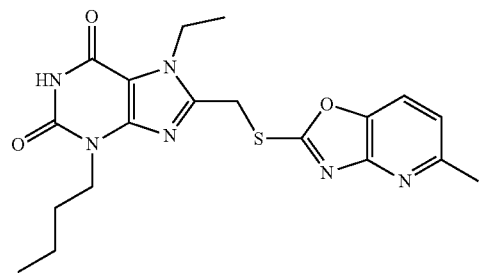 [SMILES: CCCCn1c(=O)[nH]c(=O)c2c1nc(CSc1nc3nc(C)ccc3o1)n2CC] |
| 55 | 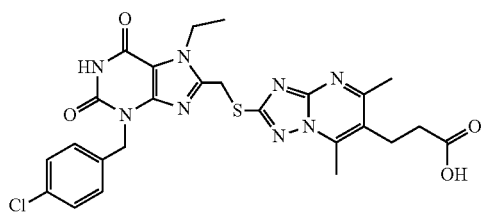 [SMILES: CCn1c(CSc2nc3nc(C)c(CCC(=O)O)c(C)n3n2)nc2c1c(=O)[nH]c(=O)n2Cc1ccc(Cl)cc1] |
| 56 | 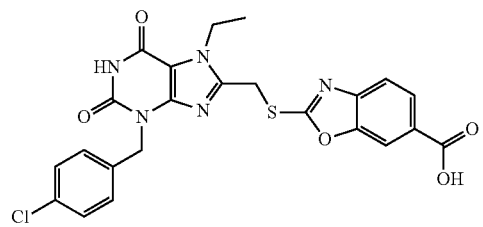 [SMILES: CCn1c(CSc2nc3ccc(C(=O)O)cc3o2)nc2c1c(=O)[nH]c(=O)n2Cc1ccc(Cl)cc1] |
| 57 | 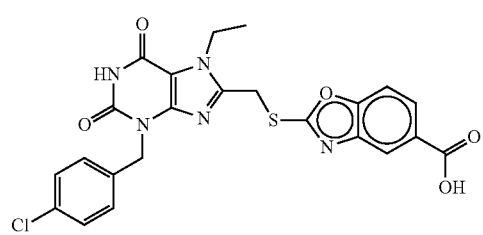 |
| 58 | 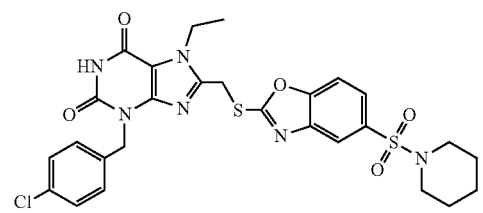 [SMILES: CCn1c(CSc2nc3cc(S(=O)(=O)N4CCCCC4)ccc3o2)nc2c1c(=O)[nH]c(=O)n2Cc1ccc(Cl)cc1] |

59 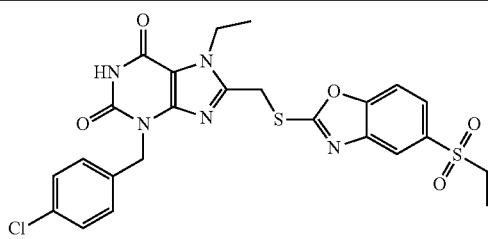
60 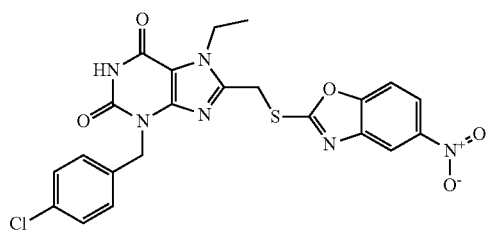 [SMILES: CCn1c(CSc2nc3cc([N+](=O)[O-])ccc3o2)nc2c1c(=O)[nH]c(=O)n2Cc1ccc(Cl)cc1]
61 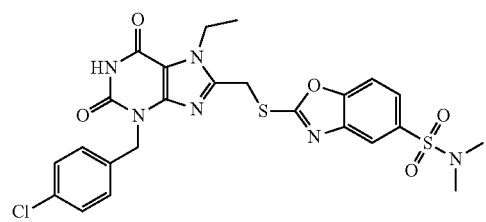 [SMILES: CCn1c(CSc2nc3cc(S(=O)(=O)N(C)C)ccc3o2)nc2c1c(=O)[nH]c(=O)n2Cc1ccc(Cl)cc1]
62 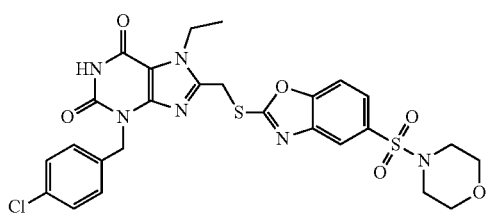 [SMILES: CCn1c(CSc2nc3cc(S(=O)(=O)N4CCOCC4)ccc3o2)nc2c1c(=O)[nH]c(=O)n2Cc1ccc(Cl)cc1]
63 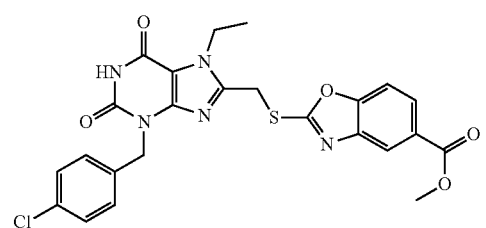 [SMILES: CCn1c(CSc2nc3cc(C(=O)OC)ccc3o2)nc2c1c(=O)[nH]c(=O)n2Cc1ccc(Cl)cc1]
64 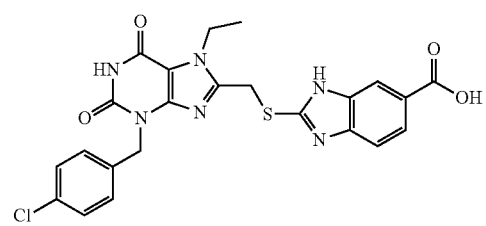 [SMILES: CCn1c(CSc2nc3ccc(C(=O)O)cc3[nH]2)nc2c1c(=O)[nH]c(=O)n2Cc1ccc(Cl)cc1]
65 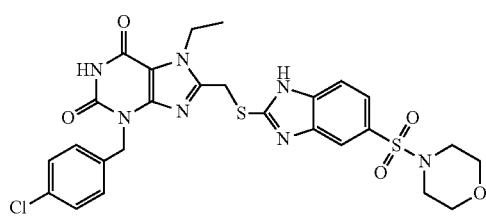 [SMILES: CCn1c(CSc2nc3cc(S(=O)(=O)N4CCOCC4)ccc3[nH]2)nc2c1c(=O)[nH]c(=O)n2Cc1ccc(Cl)cc1]

-continued
| | |
|---|---|
| 66 | 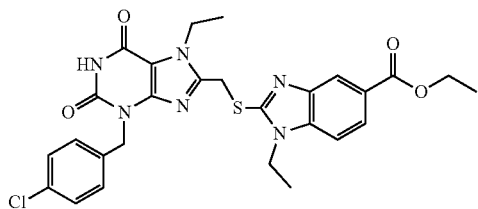 [SMILES: CCOC(=O)c1ccc2c(c1)nc(SCc1nc3c(c(=O)[nH]c(=O)n3Cc3ccc(Cl)cc3)n1CC)n2CC] |
| 67 | 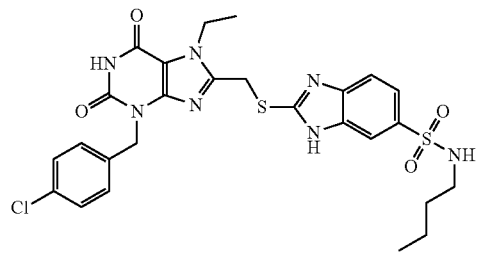 [SMILES: CCCCNS(=O)(=O)c1ccc2nc(SCc3nc4c(c(=O)[nH]c(=O)n4Cc4ccc(Cl)cc4)n3CC)[nH]c2c1] |
| 68 | 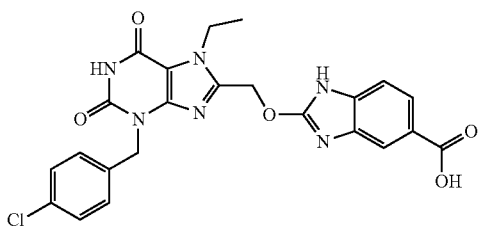 [SMILES: CCn1c(COc2nc3cc(C(=O)O)ccc3[nH]2)nc2c1c(=O)[nH]c(=O)n2Cc1ccc(Cl)cc1] |
| 69 | 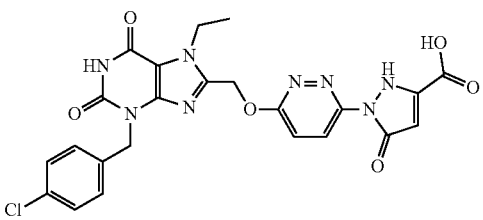 [SMILES: CCn1c(COc2ccc(-n3[nH]c(C(=O)O)cc3=O)nn2)nc2c1c(=O)[nH]c(=O)n2Cc1ccc(Cl)cc1] |
| 70 | 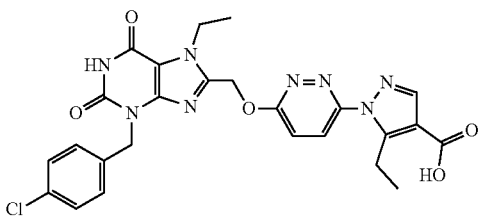 [SMILES: CCc1c(C(=O)O)cnn1-c1ccc(OCc2nc3c(c(=O)[nH]c(=O)n3Cc3ccc(Cl)cc3)n2CC)nn1] |
| 71 | 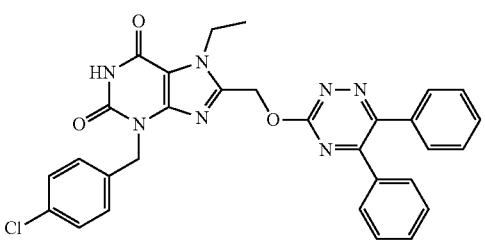 [SMILES: CCn1c(COc2nnc(-c3ccccc3)c(-c3ccccc3)n2)nc2c1c(=O)[nH]c(=O)n2Cc1ccc(Cl)cc1] |
| 72 | 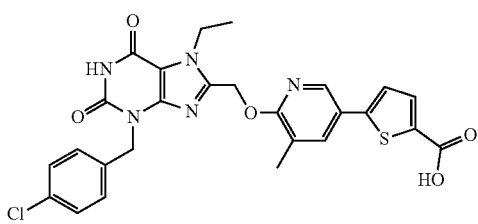 [SMILES: CCn1c(COc2ncc(-c3ccc(C(=O)O)s3)cc2C)nc2c1c(=O)[nH]c(=O)n2Cc1ccc(Cl)cc1] |

73 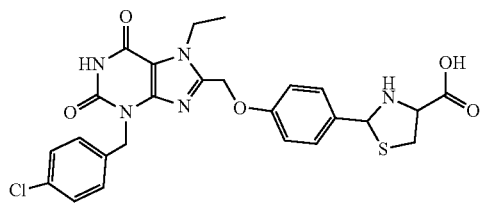 [SMILES: CCn1c(COc2ccc(C3NC(C(=O)O)CS3)cc2)nc2c1c(=O)[nH]c(=O)n2Cc1ccc(Cl)cc1]
74 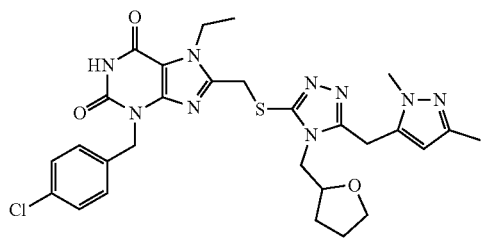 [SMILES: CCn1c(CSc2nnc(Cc3cc(C)nn3C)n2CC2CCCO2)nc2c1c(=O)[nH]c(=O)n2Cc1ccc(Cl)cc1]
75 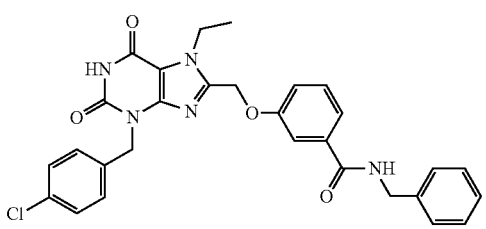 [SMILES: CCn1c(COc2cccc(C(=O)NCc3ccccc3)c2)nc2c1c(=O)[nH]c(=O)n2Cc1ccc(Cl)cc1]
76 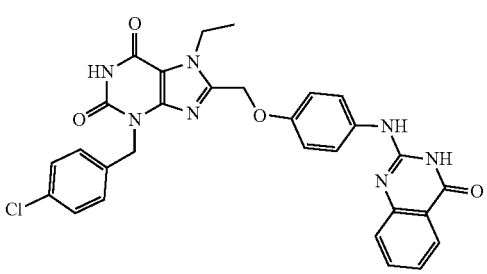 [SMILES: CCn1c(COc2ccc(Nc3nc4ccccc4c(=O)[nH]3)cc2)nc2c1c(=O)[nH]c(=O)n2Cc1ccc(Cl)cc1]
77 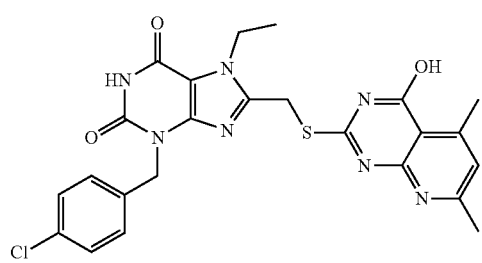 [SMILES: CCn1c(CSc2nc(O)c3c(C)cc(C)nc3n2)nc2c1c(=O)[nH]c(=O)n2Cc1ccc(Cl)cc1]
78 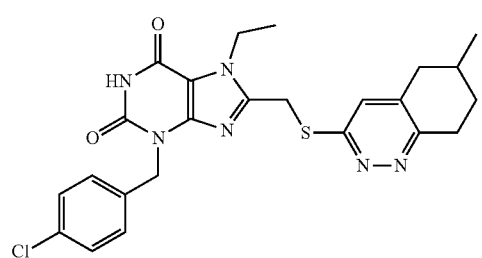 [SMILES: CCn1c(CSc2cc3c(nn2)CCC(C)C3)nc2c1c(=O)[nH]c(=O)n2Cc1ccc(Cl)cc1]

79

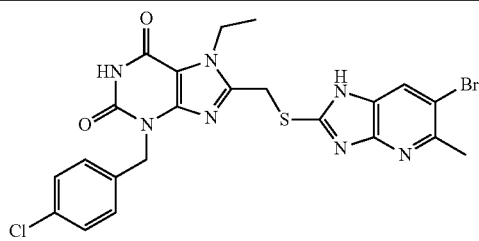

80

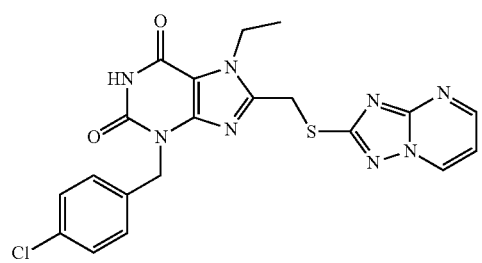 [SMILES: CCn1c(CSc2nc3ncccn3n2)nc2c1c(=O)[nH]c(=O)n2Cc1ccc(Cl)cc1]

Preferably said inhibitor has an $IC_{50}$ equal to or less than 20 µM for BRD4 (BD1).

Preferably said inhibitor has an $IC_{50}$ equal to or less than 10 µM for BRD4 (BD1).

Selective BRD4 Inhibitors

According to another embodiment, the inhibitor of general formula (I) as defined above inhibits the BRD4 protein, wherein said inhibitor binds to BD1 of BRD4, and wherein said inhibitor:

has an $IC_{50}$ for BRD4 (BD1) equal to or less than 50 µM, and has an $IC_{50}$ for BRD4 (BD1) 5 times lower than the $IC_{50}$ of the same inhibitor tested on at least one of the other bromodomains of BET proteins; and wherein $R_8$ represents a hydrogen atom, —$CH_2$—O—$R_s$, —$CH_2$—S—$R_s$;

wherein $R_s$ represents one of the following groups optionally substituted by one or more methyl, ethyl, butyl or amino groups, halogen atoms, ($C_1$-$C_4$)alkanoic acid, —S($O_2$)—($C_1$-$C_4$)alkyl, —S($O_2$)-piperidine, —S($O_2$)—(N,N)dimethylamine, —S($O_2$)-morpholine, nitro groups, —C(=O)—O—($C_1$-$C_4$)alkyl, —S($O_2$)—N(H)—($C_1$-$C_4$)alkyl, oxo-pyrazole optionally substituted by one or more ($C_1$-$C_4$)alkanoic acid, pyrazole optionally substituted by one or more ($C_1$-$C_4$)alkanoic acid or ($C_1$-$C_4$)alkyl, thiazolidin optionally substituted by one or more ($C_1$-$C_4$)alkanoic acid, —C(=O)—N(H)-benzyl, —OH, thiophenyl optionally substituted by one or more ($C_1$-$C_4$)alkanoic acid, methyl-tetrahydrofuran or —$CH_2$-pyrazole optionally substituted by one or more ($C_1$-$C_4$) alkyl:

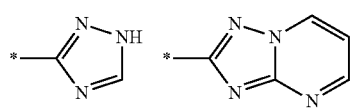

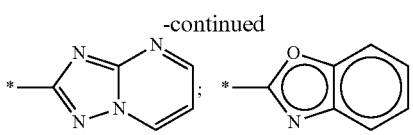

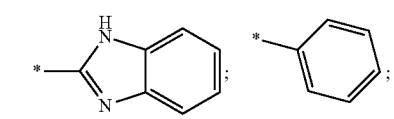

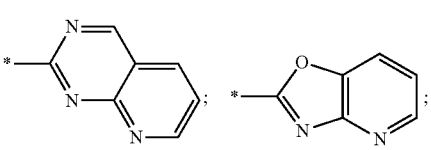

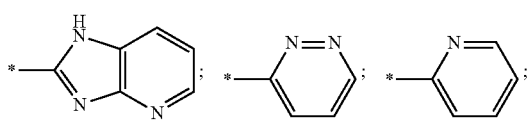

wherein * is the linking point to the sulfur atom or oxygen atom.

Preferably, said inhibitor as defined above is a selective inhibitor for the BRD4 protein.

Preferably, the selective inhibitor of BRD4 (BD1) protein is selected from the group consisting of:

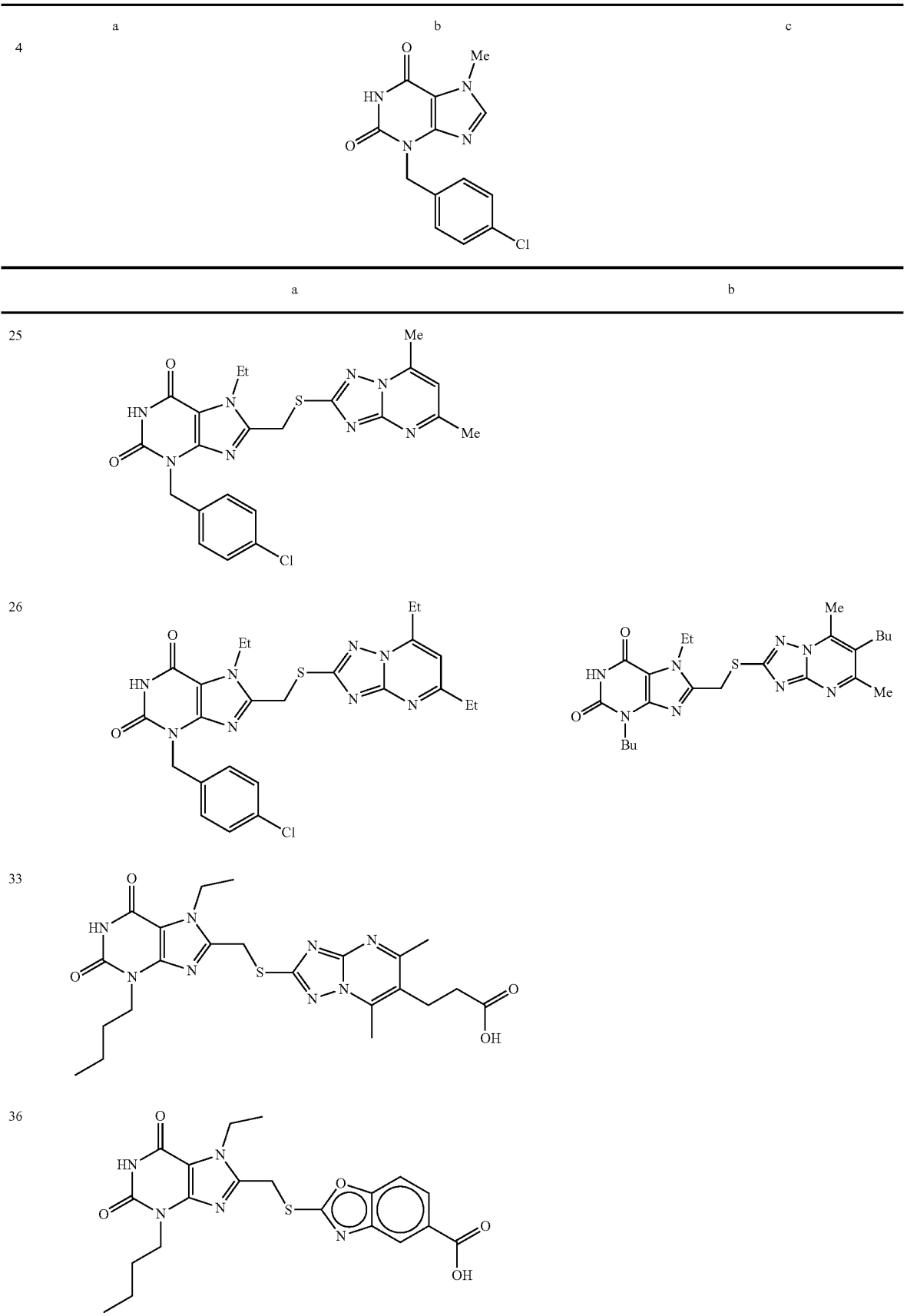

41 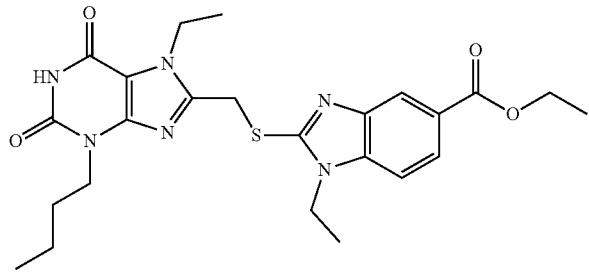 [SMILES: CCCCn1c(=O)[nH]c(=O)c2c1nc(CSc1nc3cc(C(=O)OCC)ccc3n1CC)n2CC]
53 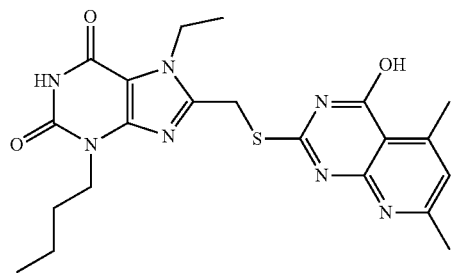 [SMILES: CCCCn1c(=O)[nH]c(=O)c2c1nc(CSc1nc(O)c3c(C)cc(C)nc3n1)n2CC]
54 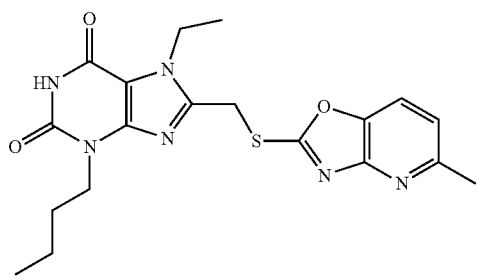 [SMILES: CCCCn1c(=O)[nH]c(=O)c2c1nc(CSc1nc3nc(C)ccc3o1)n2CC]
57 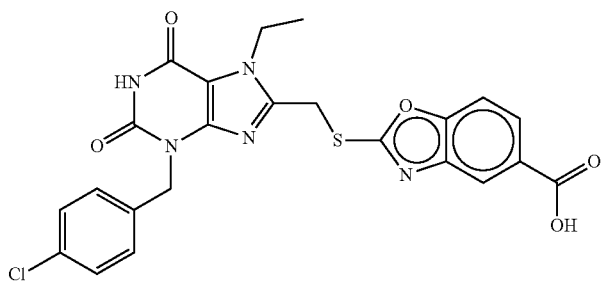
58 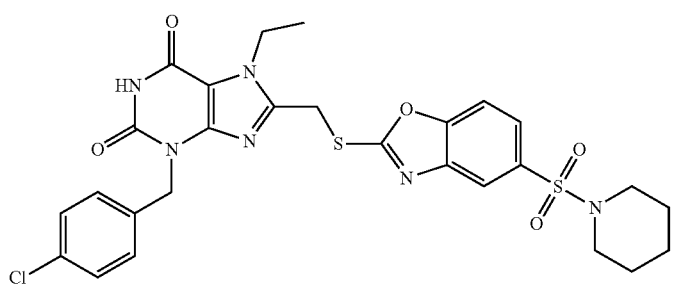 [SMILES: CCn1c(CSc2nc3cc(S(=O)(=O)N4CCCCC4)ccc3o2)nc2c1c(=O)[nH]c(=O)n2Cc1ccc(Cl)cc1]

| | |
|---|---|
| 59 | 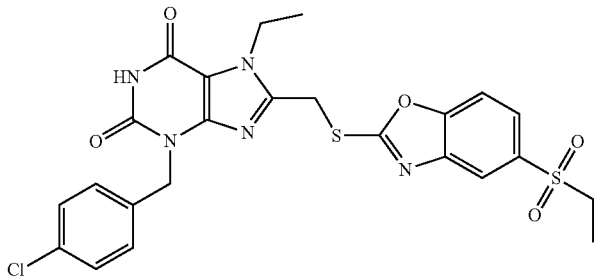 [SMILES: CCn1c(CSc2nc3cc(S(=O)(=O)CC)ccc3o2)nc2c1c(=O)[nH]c(=O)n2Cc1ccc(Cl)cc1] |
| 60 | 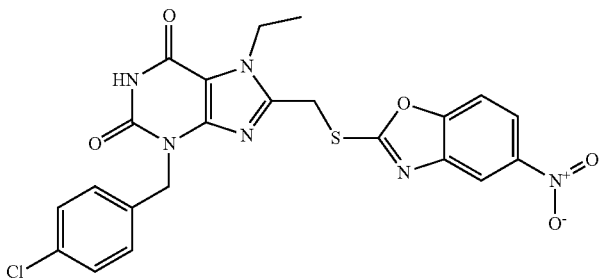 [SMILES: CCn1c(CSc2nc3cc([N+](=O)[O-])ccc3o2)nc2c1c(=O)[nH]c(=O)n2Cc1ccc(Cl)cc1] |
| 61 | 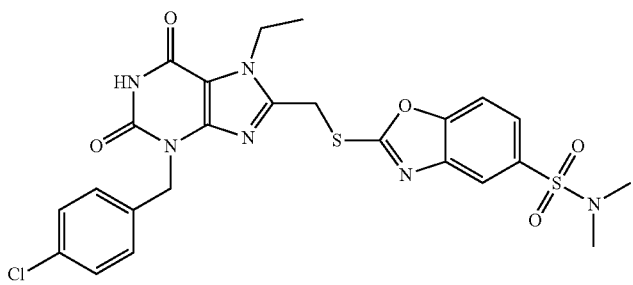 [SMILES: CCn1c(CSc2nc3cc(S(=O)(=O)N(C)C)ccc3o2)nc2c1c(=O)[nH]c(=O)n2Cc1ccc(Cl)cc1] |
| 62 | 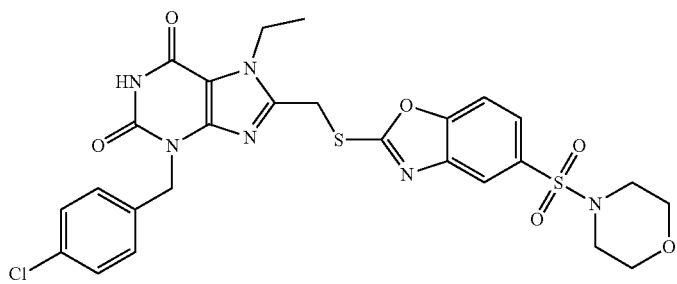 [SMILES: CCn1c(CSc2nc3cc(S(=O)(=O)N4CCOCC4)ccc3o2)nc2c1c(=O)[nH]c(=O)n2Cc1ccc(Cl)cc1] |
| 63 | 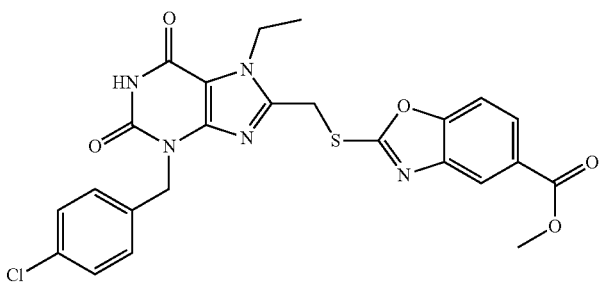 [SMILES: CCn1c(CSc2nc3cc(C(=O)OC)ccc3o2)nc2c1c(=O)[nH]c(=O)n2Cc1ccc(Cl)cc1] |

-continued
64
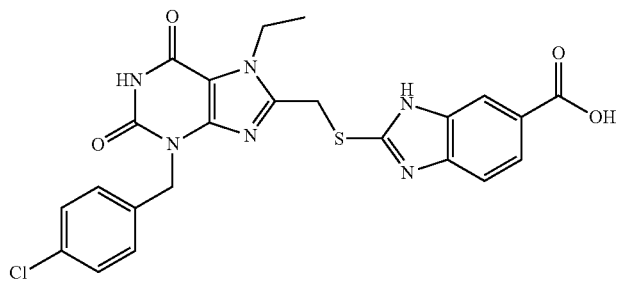 [SMILES: CCn1c(CSc2nc3ccc(C(=O)O)cc3[nH]2)nc2c1c(=O)[nH]c(=O)n2Cc1ccc(Cl)cc1]
67
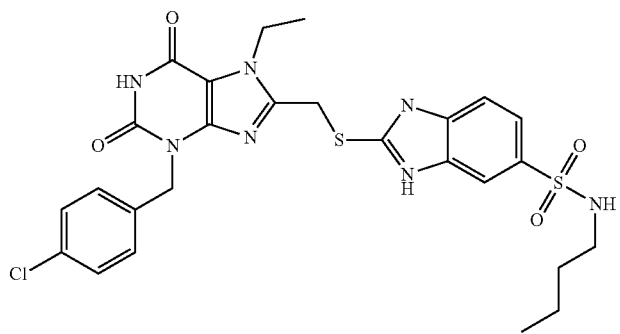 [SMILES: CCCCNS(=O)(=O)c1ccc2[nH]c(SCc3nc4c(c(=O)[nH]c(=O)n4Cc4ccc(Cl)cc4)n3CC)nc2c1]
69
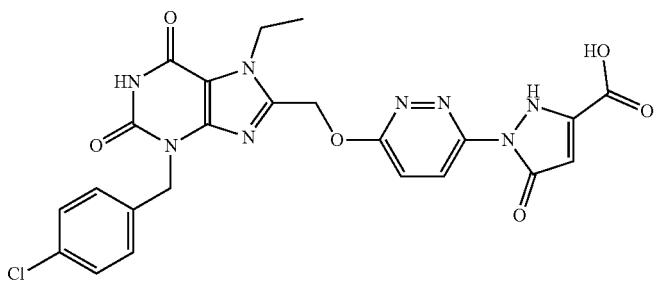 [SMILES: CCn1c(COc2ccc(-n3[nH]c(C(=O)O)cc3=O)nn2)nc2c1c(=O)[nH]c(=O)n2Cc1ccc(Cl)cc1]
70
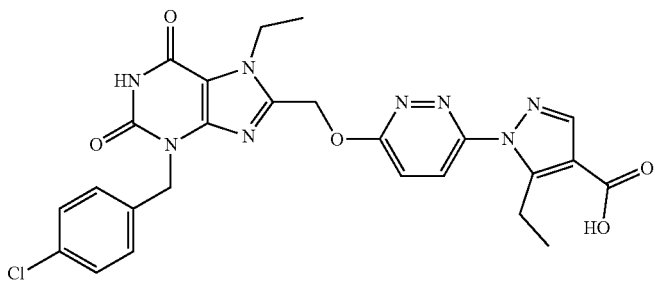 [SMILES: CCc1c(C(=O)O)cnn1-c1ccc(OCc2nc3c(c(=O)[nH]c(=O)n3Cc3ccc(Cl)cc3)n2CC)nn1]
72
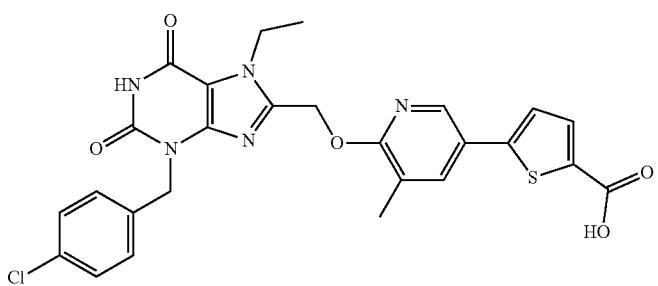 [SMILES: CCn1c(COc2ncc(-c3ccc(C(=O)O)s3)cc2C)nc2c1c(=O)[nH]c(=O)n2Cc1ccc(Cl)cc1]

73 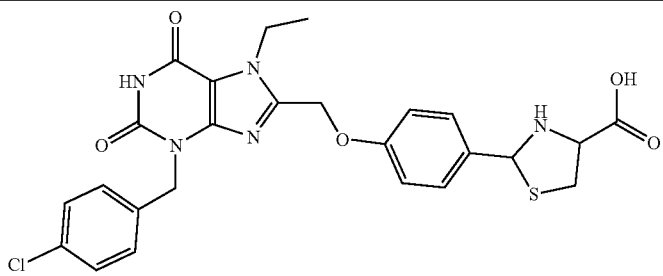

74 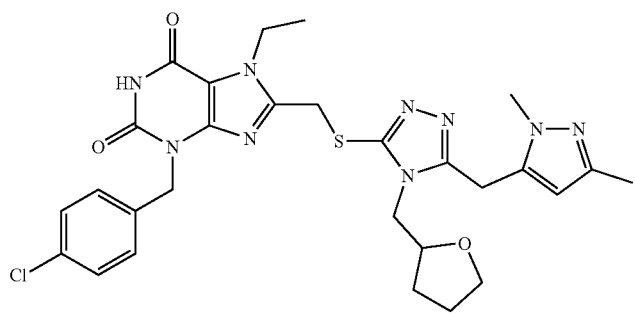 [SMILES: CCn1c(CSc2nnc(Cc3cc(C)nn3C)n2CC2CCCO2)nc2c1c(=O)[nH]c(=O)n2Cc1ccc(Cl)cc1]

75 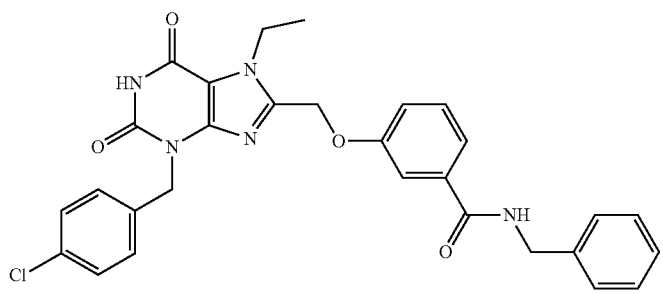 [SMILES: CCn1c(COc2cccc(C(=O)NCc3ccccc3)c2)nc2c1c(=O)[nH]c(=O)n2Cc1ccc(Cl)cc1]

79 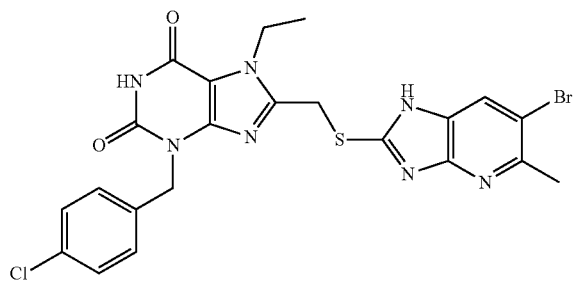 [SMILES: CCn1c(CSc2nc3nc(C)c(Br)cc3[nH]2)nc2c1c(=O)[nH]c(=O)n2Cc1ccc(Cl)cc1]

Preferably said inhibitor has an $IC_{50}$ equal to or less than 20 μM for BRD4 (BD1).

Preferably said inhibitor has an $IC_{50}$ equal to or less than 10 μM for BRD4 (BD1).

In a particular embodiment, $R_8$ is as defined above where $R_8$ is not a hydrogen atom.

According to one embodiment, the inhibitor of general formula (I) of the present invention comprises either Y, $R_3$ or $R_8$ as a linker-ligand for the E3 ubiquitin ligase, wherein the ligand for the E3 ubiquitin ligase is a cereblon ligand or a VHL ligand of following formula:

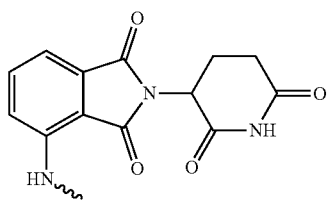

Cereblon ligand

-continued

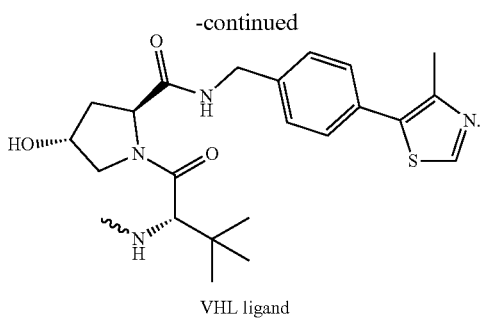

VHL ligand

Methods

The present invention also relates to a method for inhibiting a bromodomain of a BET protein by using the inhibitor of the present invention in the presence of a BET protein selected from the group consisting of BRD2, BRD3, BRD4 and BRDT.

The present invention also relates to a method for inhibiting a BRD4 protein, wherein said inhibitor binds to BD1 of BRD4, and wherein said inhibitor has an $IC_{50}$ for BRD4 (BD1) equal to or less than 50 µM, by using the inhibitor of the present invention in the presence of a BRD4 (BD1) protein.

The present invention also relates to a method for inhibiting a BRD4 protein by using the selective inhibitor as defined above in the presence of a BRD4 protein.

Preferably, said method as defined above is a method for inhibiting selectively a BRD4 protein.

The present invention also relates to an in vivo method for degrading a BET protein, by using the inhibitor of the present invention as described above in presence of the E3 ubiquitin ligase, wherein the inhibitor comprises either Y, $R_3$ or $R_8$ as a linker-ligand for the E3 ubiquitin ligase. In a preferred embodiment, said ligand for the E3 ubiquitin ligase is a cereblon ligand or a VHL ligand of following formula:

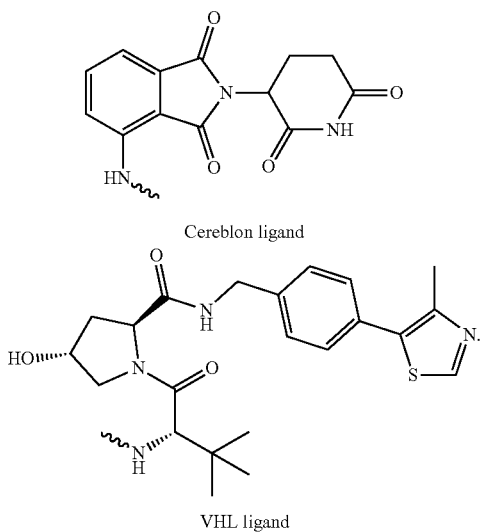

Cereblon ligand

VHL ligand

In a particular embodiment, the present invention relates to an in vivo method for degrading a BET protein, by using the inhibitor of the present invention as described above, in presence of cells which express the E3 ubiquitin ligase, wherein the inhibitor comprises either Y, $R_3$ or $R_8$ as a linker-ligand for the E3 ubiquitin ligase.

According to one embodiment, the present invention relates to a therapeutic use of the methods as defined above. In another embodiment, the present invention relates to non-therapeutic use of the methods as defined above.

Therapeutic Uses

It is known from the prior art that BET proteins facilitate the assembly of the transcriptional machinery and control gene expression in inflammation, viral infection and cancer biology[1-17] It has also been demonstrated that BET proteins are often deregulated in diseases, their transcription-regulating activity being altered and thus affecting numerous growth-promoting genes and cytokines.

Recent disclosure of pan-BET inhibitors (multi-targeted BET inhibitors) that attenuate BRD function has allowed the validation of these drug targets, shedding light on their roles in disease.

The present Inventors have found and demonstrated the inhibitory activity of xanthine derivative compounds of general formula (I) towards BET proteins. Therefore, BET protein inhibitors of the present invention, which are xanthine derivative compounds, can be used for treating diseases involving BET proteins. Such diseases are, but are not limited to cancer, inflammatory disease, sepsis, autoimmune disease, neurodegenerative disease, cardiovascular disorder, renal disorder, viral infection or obesity (see Patents applications published as US20140296246, EP2646446, WO201580707, US20140296243, EP2859000 and US20150148344).

Consequently, in another embodiment, the inhibitor of the present invention is a compound for use as a medicament.

The present invention also provides a pharmaceutical composition comprising as active principle, the inhibitor as defined above and a pharmaceutically acceptable excipient.

The present invention also relates to a method for treating a disease involving bromodomains of BET proteins, comprising administering to a patient an effective amount of the inhibitor of general formula (I) as defined above, or of a composition comprising said inhibitor. Such diseases are, but are not limited to cancer, inflammatory disease, sepsis, autoimmune disease, neurodegenerative disease, cardiovascular disorder, renal disorder, viral infection or obesity.

Preferably, the inhibitor is an inhibitor of the BRD4 protein wherein said inhibitor binds to BD1 of BRD4.

Preferably, said inhibitor has an $IC_{50}$ for BRD4 (BD1) equal to or less than 50 µM.

More preferably said inhibitor has an $IC_{50}$ equal to or less than 20 µM for BRD4 (BD1).

Even more preferably said inhibitor has an $IC_{50}$ equal to or less than 10 µM for BRD4 (BD1).

In a particular embodiment, the present invention provides a method for treating a patient having a cancer, inflammatory disease, sepsis, autoimmune disease, neurodegenerative disease, cardiovascular disorder, renal disorder, viral infection or obesity condition.

The present invention also relates to an inhibitor for use in the treatment of cancer, inflammatory disease, sepsis, autoimmune disease, neurodegenerative disease, cardiovascular disorder, renal disorder, viral infection or obesity.

In another embodiment, the disease to be treated is selected from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors. Solid tumors are, but not limited to, tumors of the colon, rectum, prostate, lung, pancreas, liver, kidney, cervix, stomach, ovaries, breast, skin, brain, meninges or central nervous system.

Synthesis

Compounds of formula (I) can be considered as purine derivatives. The synthesis of purines is well documented and purines of the invention can be prepared from either commercially available guanosine or alkylamine according to standard procedures described in following scheme 1 and 2 respectively.

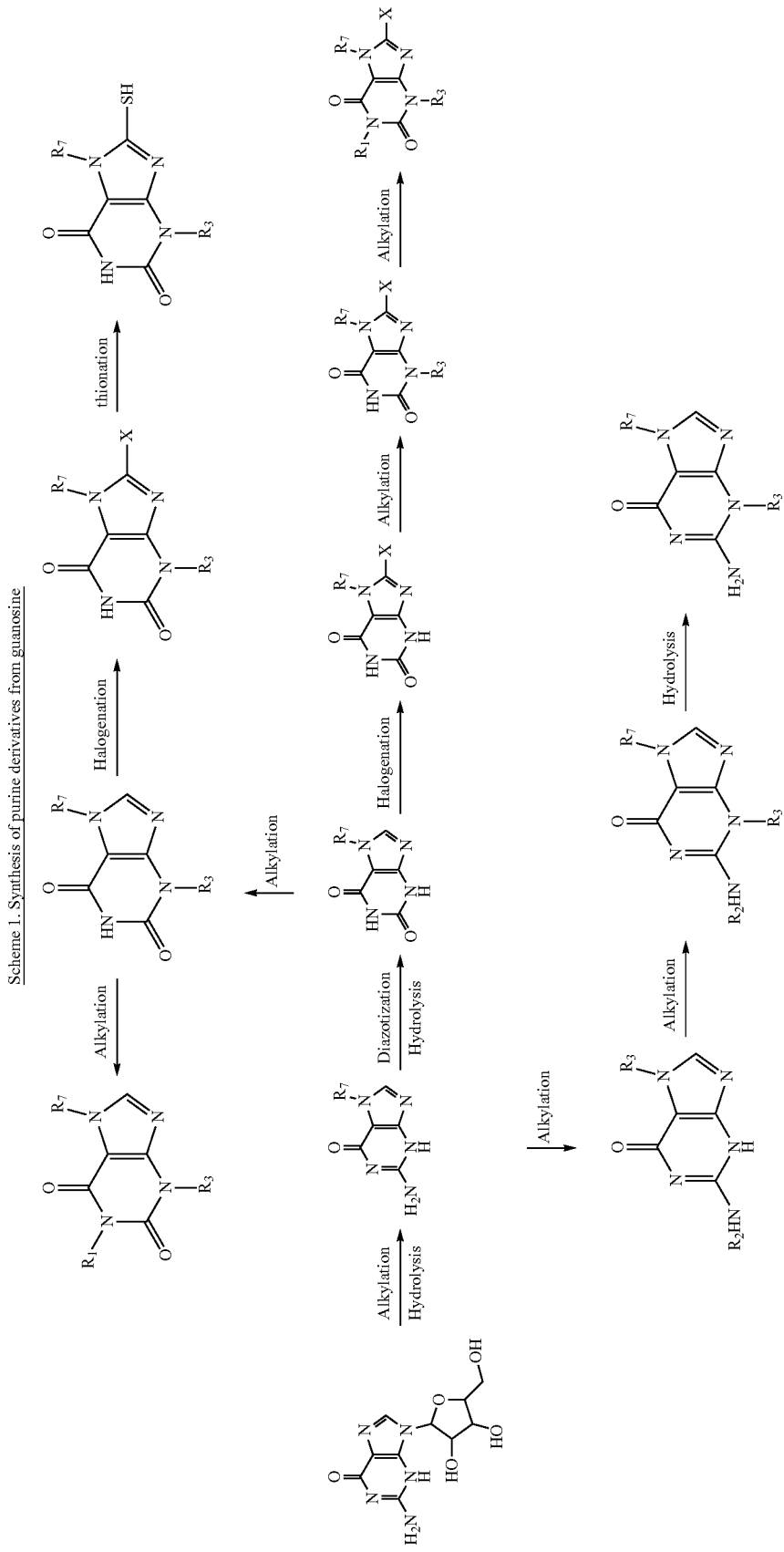
Scheme 1. Synthesis of purine derivatives from guanosine

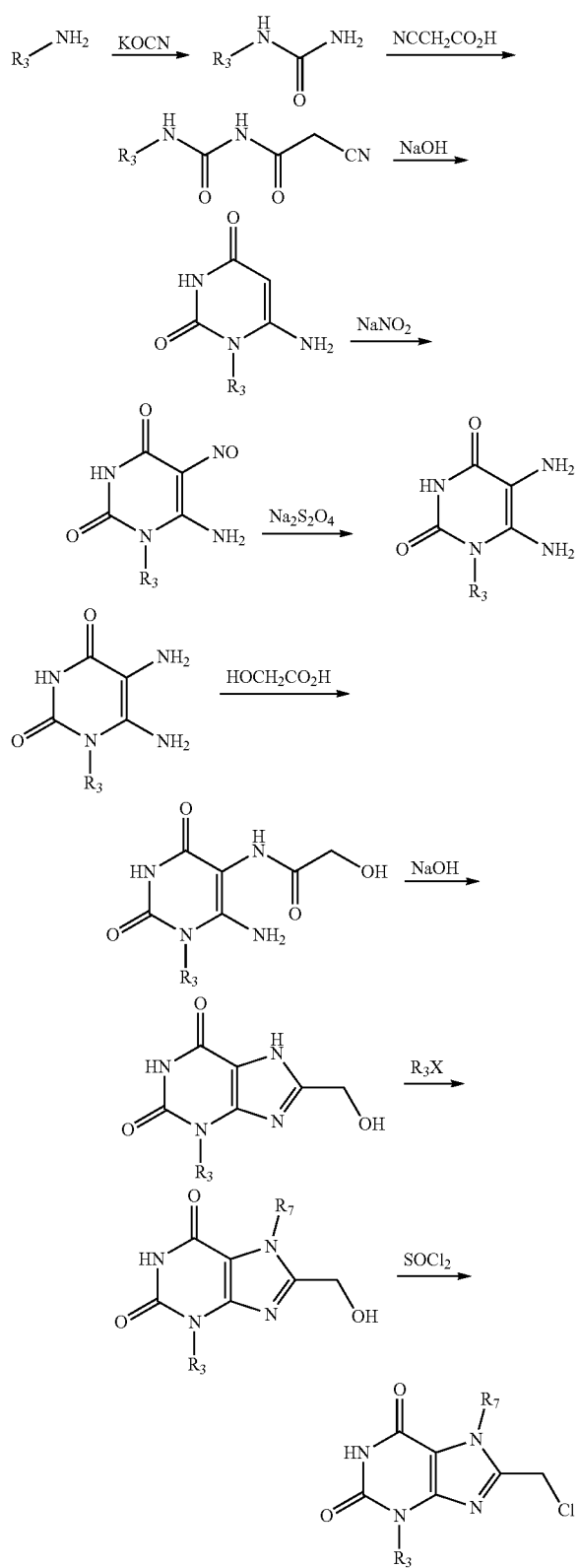

Scheme 2. Synthesis of purine derivatives from alkylamines

Typically, from guanosine, an appropriate sequence of alkylation, hydrolysis, diazotization, halogenation and halogeno-thiol exchange is used to prepare a wide series of variously substituted purine derivatives. Starting from alkylamine, the condensation with potassium cyanate affords alkylurea conversion into corresponding 6-aminouracil by treating with cyanoacetic acid and sodium hydroxide successively. Subsequent nitrosylation, and reduction leads to expected diaminouracil. Condensation with carboxylic acid followed by base induces ring closure acylation and affords the expected purines. For example, condensation with glycolic acid affords the 8-hydroxymethyl-purine derivatives useful to prepare other formula (I) compounds.

The selective bromodomain inhibitors of formula (I) as described herein can be prepared by coupling activated purine precursors described above with appropriate partner for nucleophilic displacement.

Design and synthesis of compounds 33a to 80a of the invention combines molecular modeling coupled to an automated synthesis robotic platform and a high throughput laboratory workstation (referred as DOTS). The full process has been set-up without any intermediary purification processes.

The in silico optimization strategy relies on 2 main steps: 1) the design of a diversity-oriented target-focused chemical library using medicinal chemistry relevant reactions and a collection of commercially available building blocks; 2) the virtual screening of this chemical library using S4MPLE, a conformational sampling tool, able to deal with hundreds of intra/intermolecular degrees of freedom in the context of one (conformer enumeration) or more molecules (docking). S4MPLE relies on a Lamarckian genetic algorithm and significant flexibility may be enabled (e.g. ligands, target side chains and backbone). Energy calculations are based on the AMBER force field and its generalized version GAFF for ligands.

A xanthine-focused chemical library of approximately 7000 compounds was generated using a Williamson-like reaction and a collection of building blocks. Interestingly, the original selective inhibitor (26b) was correctly generated and ranked at the top 1%. About 50 building blocks were purchased to prepare a representative set of compounds from the top 1%. The compounds have been synthetized using an automated robotic platform from Chemspeed by coupling activated purine precursors previously described with appropriate commercially available partner for nucleophilic displacement (scheme 1).

Scheme 1. Synthesis of bromodomain inhibitors of formula (I)

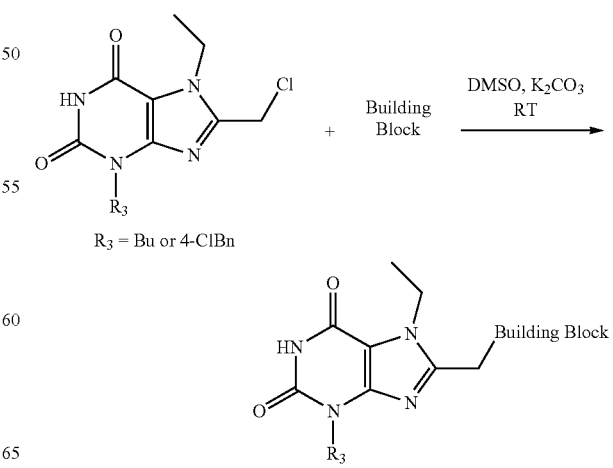

$R_3$ = Bu or 4-ClBn

The Accelerator Synthetizer SLT100 allows the efficient synthesis of the focused library in 96 well plates that can be directly transferred to a Labcyte Access/Echo® Laboratory Workstation to assess the compounds for their ability to disrupt bromodmain/histone complexes using the homogeneous time-resolved fluorescence (HTRF®) technology (IC50 µM).

Although the exemplary embodiments of the present invention have been disclosed for illustrative purposes, a person skilled in the art will appreciate that various modifications, additions and substitutions are possible, without departing from the scope and spirit of the invention as disclosed in the accompanying claims.

The present invention will now be illustrated using the following examples and FIGURES, which are given by way of illustration, and are in no way limiting.

EXAMPLES

Figure 1A:
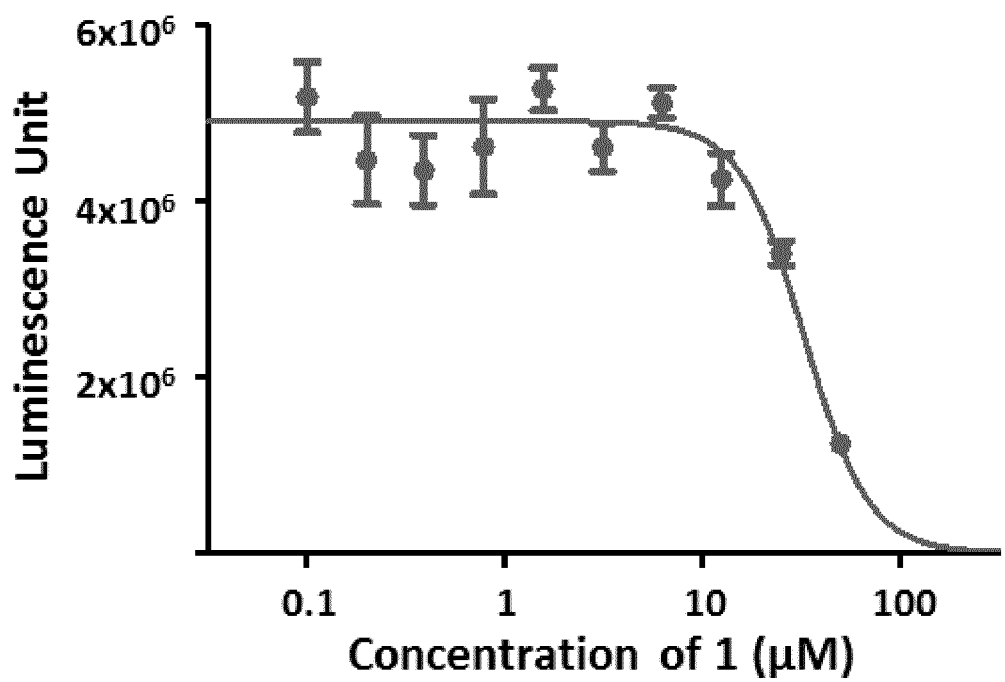
FIG. 1. Cell-based assays (A) Effect of 26b on Jurkat cell viability as a function of the compound concentration after 72 h incubation at 37° C. (B) C-myc pro-oncogene down-regulation profile in the presence of different concentrations of 26b at 0.5% DMSO after 24 h incubation (50 µg of loaded protein).

Preparation of the Compounds According to the Invention
General Synthesis of the Compounds According to the Invention Proton NMR spectra, 1H and 13C NMR, were recorded by using a Bruker AC400 or AC250 spectrometer. Chemical shifts, δ are expressed in ppm and coupling values, J, in hertz. Abbreviations for peaks are, br: broad, s: singlet, d: doublet, t: triplet, q: quadruplet, quint: quintuplet, sex: sextuplet and m: multiplet. The spectra recorded are consistent with the proposed structures. Reaction monitoring and purity of compounds were recorded by using analytical Agilent Infinity high performance liquid chromatography (Column Zorbax SB-C18 1.8 µM (2.1×50 mm); Mobile phase (A: 0.1% FA H$_2$O, B: 0.1% FA MeCN, Time/% B 0/10, 4/90, 7/90, 9/10, 10/10); Flow rate 0.3 mL/min; Diluent MeOH) with DAD at 230 nM. All tested compounds yielded data consistent with a purity of ≥95%.

Example 1: 3-Butyl-8-(6-butyl-5,7-dimethyl-[1,2,4]triazolo[1,5-a]pyrimidin-2-ylsulfanylmethyl)-7-ethyl-3,7-dihydro-purine-2,6-dione (26b)

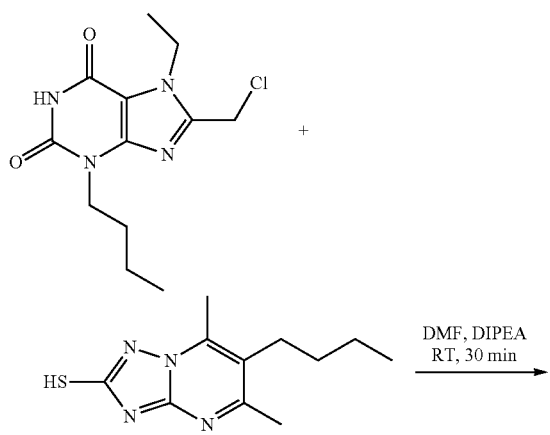

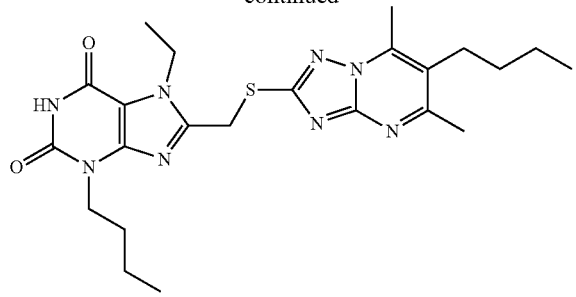

To a solution of 6-butyl-5,7-dimethyl-[1,2,4]triazolo[1,5-a]pyrimidine-2-thiol (35 mg, 0.15 mmol) in dimethylformamide (2 mL) was injected diisopropylethylamine (26 µL, 0.15 mmol). After 5 min under stirring, a solution of 3-butyl-8-chloromethyl-7-ethylxanthine (43 mg, 0.15 mmol) in dimethylformamide (2 mL) was added dropwise. The resulting mixture was stirred at room temperature for 30 min. The solvent was distilled off under reduced pressure and the residue purified by column chromatography (CH$_2$Cl$_2$-MeOH 10:0.5) to afford the 3-butyl-8-(6-butyl-5,7-dimethyl-[1,2,4]triazolo[1,5-a]pyrimidin-2-ylsulfanylmethyl)-7-ethyl-3,7-dihydro-purine-2,6-dione (64 mg, 88%) as white solid. Rf=0.29. 1H NMR (250 MHz, CDCl$_3$) δ 7.88 (1H, sbroad), 4.73 (2H, s), 4.49 (2H, q, J=7.1 Hz), 4.04 (2H, t, J=7.4 Hz), 2.76 (3H, s), 2.73-2.69 (2H, m), 2.69 (3H, s), 1.73 (2H, quint, J=7.4 Hz), 1.56-1.34 (6H, m), 1.40-1.28 (2H, m), 1.45 (3H, t, J=7.4 Hz), 1.01 (3H, t, J=7.1 Hz) and 0.95 (3H, t, J=7.4 Hz); 13C NMR (100 MHz, CDCl3) δ 165.0, 164.1, 154.1, 153.8, 150.6, 150.1, 149.2, 143.5, 121.8, 42.7, 41.4, 31.9, 30.2, 28.0, 26.8, 23.8, 22.9, 20.0, 16.6, 14.0, 13.9 and 13.8. LCMS C$_{23}$H$_{32}$N$_8$O$_2$S Rt=6.755 min, m/z=484.6, purity >99%. HRMS (ESI+) for C$_{23}$H$_{33}$N$_8$O$_2$S (M+H) calcd, 485.2442; found, 485.2442.

3-butyl-8-chloromethyl-7-ethylxanthine (19c)

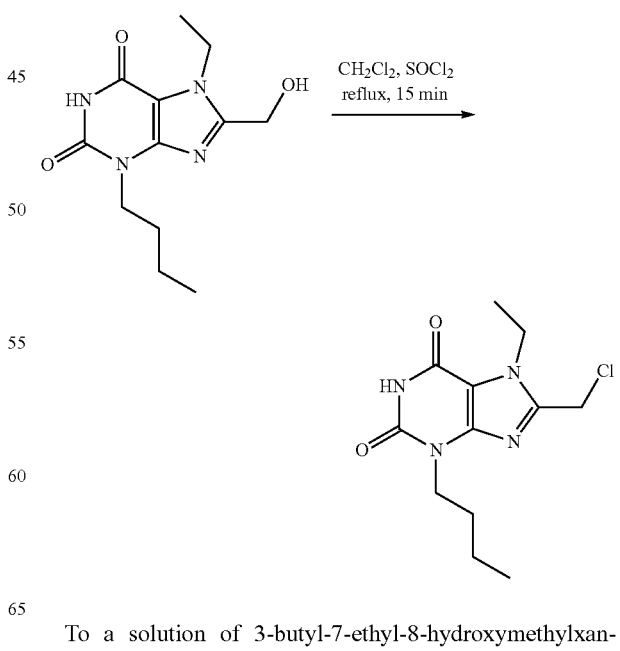

To a solution of 3-butyl-7-ethyl-8-hydroxymethylxanthine (345 mg, 1.3 mmol) in dichloromethane (5 mL) was injected thionyl chloride (283 μL, 3.9 mmol). The reaction mixture was refluxed 15 min. then the solvent was distillated off under reduced pressure. The residue was extended with Et₂O (20 mL) to allow crystallization and the precipitate was collected by filtration affording 3-butyl-8-chloromethyl-7-ethylxanthine (325 mg, 88%) as a light yellow powder. ¹H NMR (250 MHz, MeOD) δ 4.77 (2H, s), 4.38 (2H, q, J=7.1 Hz), 4.00 (2H, t, J=7.3 Hz), 1.70 (2H, quint, J=7.3 Hz), 1.50 (3H, t, J=7.1 Hz) 1.39 (2H, sex, J=7.3 Hz) and 0.94 (3H, t, J=7.3 Hz).

3-Butyl-7-ethyl-8-hydroxymethylxanthine (18a)

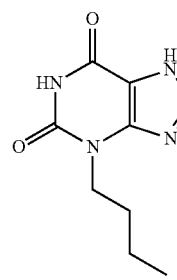

Under argon, at 0° C., to a mixture of 3-butyl-8-hydroxymethylxanthine (238 mg, 1 mmol) and potassium carbonate (152 mg, 1.1 mmol) in dimethylformamide (20 mL) was injected a solution of ethyl iodide (80 μL, 1 mmol) in dimethylformamide (5 mL). The resulting mixture was allowed to warm at room temperature and stirred at this temperature overnight. The solvent was distillated off under reduce pressure and the residue successively diluted with H₂O (10 mL), acidified with aqueous 10% HCl (10 mL) and extracted with CH₂Cl₂ (3×5 mL). The combined organic layers were dried over Na₂SO₄ and the solvent was distillated off to afford 3-butyl-7-ethyl-8-hydroxymethylxanthine (182 mg, 72%) as a light yellow solid. ¹H NMR (250 MHz, MeOD) δ 4.72 (2H, s), 4.40 (2H, q, J=7.2 Hz), 3.98 (2H, t, J=7.3 Hz), 1.69 (2H, quint, J=7.3 Hz), 1.45 (3H, t, J=7.2 Hz) 1.37 (2H, sex, J=7.3 Hz) and 0.93 (3H, t, J=7.3 Hz); ¹³C NMR (63 MHz, MeOD) δ 156.4, 153.7, 152.7, 150.4, 109.0, 56.9, 43.4, 42.1, 31.2, 20.9, 16.7 and 14.1.

3-Butyl-8-hydroxymethylxanthine (17a)

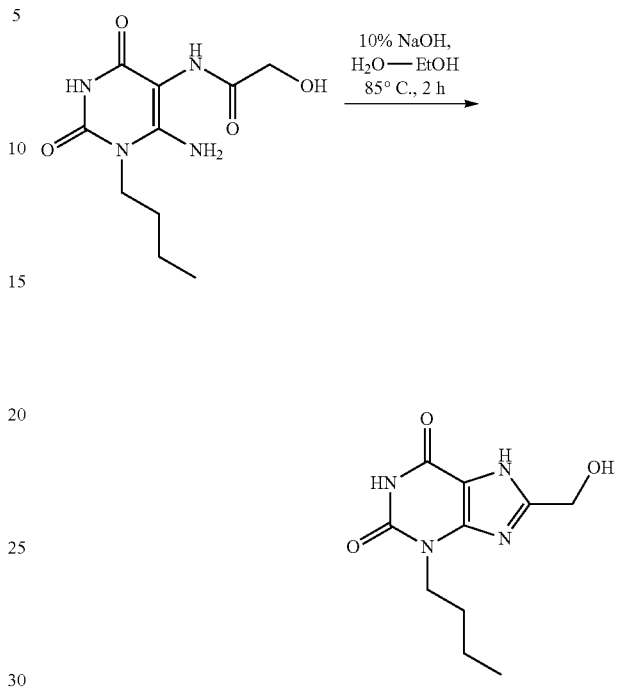

At 85° C., to a solution of N-(6-amino-1-butyl-2,4-dioxo-1,2,3,4-tetrahydropyrimidin-5-yl)-2-hydroxyacetamide (1.83 g, 7.1 mmol) in a mixture of ethanol (10 mL) and water (5 mL) was added dropwise a 10% aqueous sodium hydroxide (5 mL) over 30 min. After addition the reaction mixture was stirred at 85° C. for 2 h, allowed to cool at room temperature, diluted with H₂O (10 mL) and then acidified with aqueous 1N HCl until pH=1. After cooling in ice bath for few min. the precipitate was collected by filtration and generously washed with H₂O. The solid was dried overnight in oven at 80° C. affording 3-butyl-8-hydroxymethylxanthine (1.45 g, 81%) as a light yellow powder. ¹H NMR (250 MHz, DMSO-d6) δ 4.49 (2H, s), 3.89 (2H, t, J=7.3 Hz), 1.61 (2H, quint, J=7.3 Hz), 1.28 (2H, sex, J=7.3 Hz) and 0.90 (3H, t, J=7.3 Hz). ¹³C NMR (63 MHz, DMSO-d6) δ 154.5, 153.9, 150.9, 149.4, 106.8, 56.9, 41.7, 19.5 and 13.0.

N-(6-Amino-1-butyl-2,4-dioxo-1,2,3,4-tetrahydropyrimidin-5-yl)-2-hydroxyacetamide

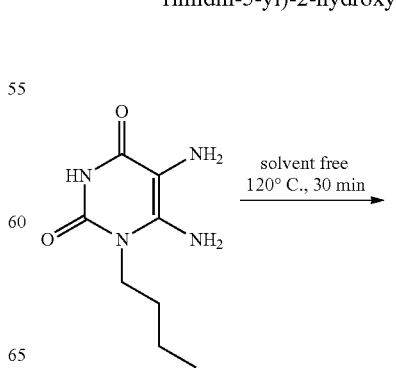

6-Amino-5-nitroso-1-butyluracil

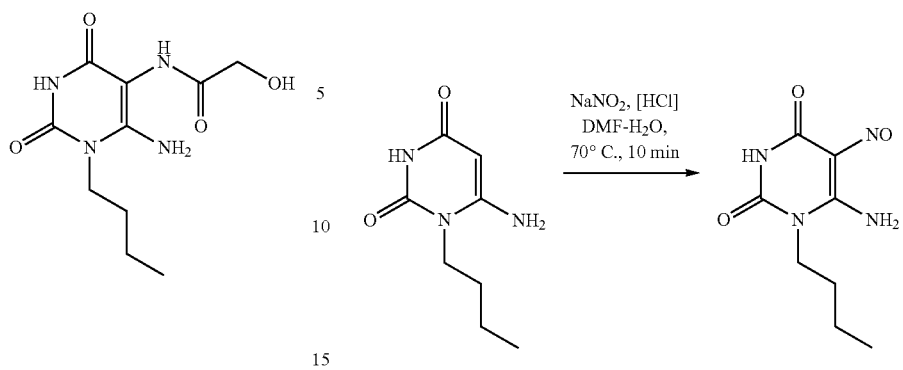

At 70° C., to a solution of 6-amino-1-butyluracil (7.7 g, 42 mmol) in a mixture of N,N-dimethylformamide (70 mL) and water (25 mL) was added sodium nitrite (1.27 g, 69 mmol) then concentrated hydrochloric acid (5 mL). After 10 min. under stirring at 70° C., the mixture was allowed to cool at room temperature and kept at 4° C. overnight. The precipitate was filtered off, washed with $H_2O$, and dried under reduced pressure, to afford 6-amino-5-nitroso-1-butyluracil 16 (7.68 g, 86%) as purple powder. $^1$H NMR (250 MHz, DMSO-d6) δ 12.62 (2H, sbroad), 10.89 (1H, sbroad), 3.76 (2H, t, J=7.4 Hz), 1.48 (2H, quint, J=7.4 Hz), 1.29 (2H, sex, J=7.4 Hz) and 0.91 (3H, t, J=7.4 Hz).

5,6-diamino-1-butyluracil

Under stirring and solvent free condition, a mixture of 5,6-diamino-1-butyluracil (2.75 g, 13.9 mmol) and glycolic acid (2.116 g, 28 mmol) was heated at 120° C. for 30 min. To the resulting solid, allowed to cool at room temperature, was successively added EtOH (20 mL), $H_2O$ (4 mL) and $Et_2O$ (60 mL). The precipitate was filtrated off and washed with $Et_2O$ to afford N-(6-amino-1-butyl-2,4-dioxo-1,2,3,4-tetrahydropyrimidin-5-yl)-2-hydroxyacetamide (3.29 g, 93%) as light yellow powder. $^1$H NMR (250 MHz, DMSO-d6) δ 10.57 (1H, sbroad), 8.09 (1H, s), 6.57 (2H, s), 5.34 (1H, sbroad), 3.93 (2H, s), 3.78 (2H, t, J=7.2 Hz), 1.49 (2H, quint, J=7.2 Hz), 1.30 (2H, sex, J=7.2 Hz) and 0.89 (3H, t, J=7.2 Hz).

6-Amino-1-butyluracil

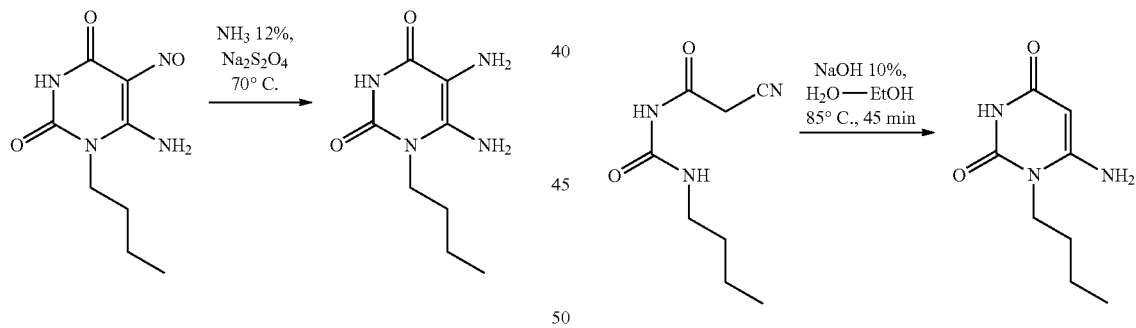

At 70° C., to a solution of 6-amino-5-nitroso-1-butyluracil (7.68 g, 36 mmol) in 12% aqueous solution of ammonia (150 mL) was added sodium hydrosulfite (19 g, 0.11 mol) in solid fraction over 15 min. After addition, the reaction mixture was allowed to cool at room temperature and kept at 4° C. for 1 h. The precipitate was collected by filtration, washed with $H_2O$, and dried under reduced pressure to afford 5,6-diamino-1-butyluracil 18 (4.9 g, 68%) as light green powder. $^1$H NMR (250 MHz, DMSO-d6) δ 10.51 (1H, sbroad), 6.13 (2H, sbroad), 3.76 (2H, t, J=7.3 Hz), 2.85 (2H, sbroad), 1.48 (2H, quint, J=7.3 Hz), 1.28 (2H, sex, J=7.3 Hz) and 0.88 (3H, t, J=7.3 Hz). $^{13}$C NMR (63 MHz, MeOD) δ 159.3, 152.9, 152.3, 124.4, 44.5, 30.8, 20.7 and 14.1.

At 85° C., to a suspension of N-butyl-N'-cyanoacetylurea (13.5 g, 73.8 mmol) in a mixture of water (30 mL) and ethanol (50 mL) was added dropwise a 10% aqueous sodium hydroxide (10 mL) over a period of 15 min. After addition, the resulting mixture was stirred at 85° C. for 45 min. The reaction solution was concentrated under reduced pressure to allow crystallization. The solid was collected by filtration and fully washed with $Et_2O$ to afford 6-amino-1-butyluracil (13 g, 96%) as white powder. $^1$H NMR (250 MHz, DMSO-d6) δ 10.29 (1H, sbroad), 6.77 (2H, sbroad), 4.52 (1H, s), 3.71 (2H, t, J=7.3 Hz), 1.46 (2H, quint, J=7.3 Hz), 1.27 (2H, sex, J=7.3 Hz) and 0.88 (3H, t, J=7.3 Hz).

N-Butyl-N'-cyanoacetylurea

Example 2: 3-Butyl-8-(6-butyl-5,7-dimethyl-[1,2,4]triazolo[1,5-a]pyrimidin-2-ylmethylsulfanyl)-7-ethyl-3,7-dihydro-purine-2,6-dione (32a)

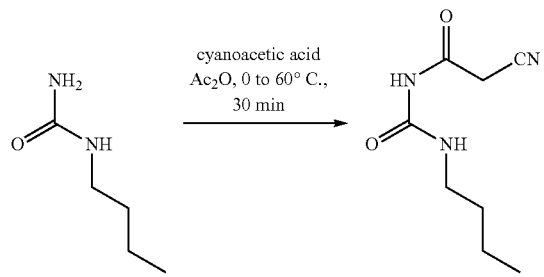

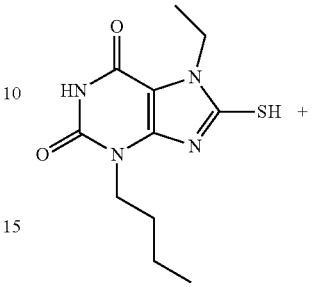

At 0° C., to a solution of cyanoacetic acid (10.18 g, 0.120 mol) in acetic anhydride (22.3 mL) was added butylurea (13.88 g, 0.12 mol) by solid fraction over 5 min. The mixture was successively stirred at 0° C. for 15 min., allowed to warm at room temperature, heated at 60° C. for 30 min, until completion of the reaction, then allowed to cool at room temperature. To the resulting precipitate was added Et$_2$O (60 mL) and the solid was collected by filtration to afford N-butyl-N'-cyanoacetylurea (18.5 g, 84%) as fine white needles. $^1$H NMR (250 MHz, DMSO-d6) δ 10.53 (1H, sbroad), 7.96 (1H, t, J=7.4 Hz), 3.91 (2H, s), 3.14 (2H, q, J=7.4 Hz), 1.44 (2H, quint, J=7.4 Hz), 1.28 (2H, sex, J=7.4 Hz), and 0.88 (3H, t, J=7.4 Hz).

Butylurea

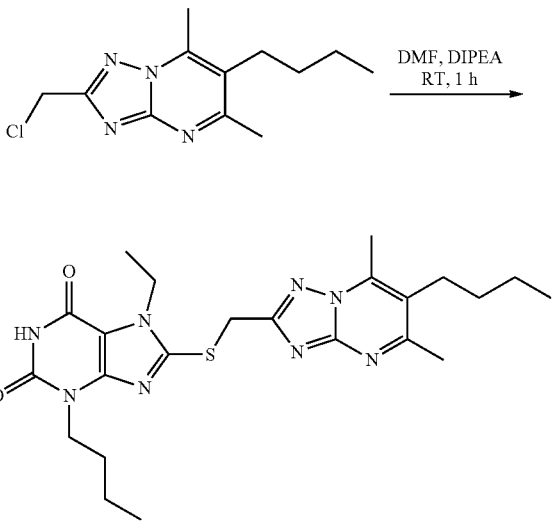

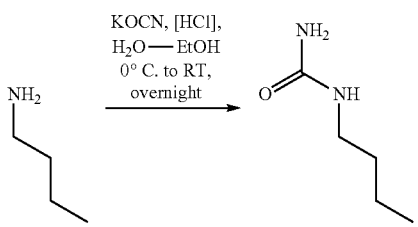

At 0° C., to butylamine (10.73 g, 0.147 mol) was added concentrated hydrochloric acid (14.7 ml, 0.176 mol) and the mixture was poured into hot ethanol (150 mL). The resulting solution was then added to a solution of potassium cyanate (14.61 g, 0.176 mol) in water (150 mL) and stirring was maintained at room temperature overnight. The reaction mixture was concentrated under reduced pressure until few volume to allow butylurea to crystallize (15 g, 88%) as white plates. $^1$H NMR (250 MHz, DMSO-d6) δ 6.02 (1H, t, J=6.7 Hz), 5.41 (2H, sbroad), 2.92 (2H, q, J=6.7 Hz), 1.34-1.19 (4H, m) and 0.84 (3H, t, J=6.7 Hz); $^{13}$C NMR (63 MHz, DMSO-d6) δ 160.0, 39.5, 32.4, 20.1 and 14.3.

To a solution of 3-butyl-7-ethyl-8-mercaptoxanthine (54 mg, 0.4 mmol) in dimethylformamide (2 mL) was injected diisopropylethylamine (70 μL, 0.4 mmol). After 5 min under stirring, a solution of 6-butyl-2-chloromethyl-5,7-dimethyl-[1,2,4]triazolo[1,5-a]pyrimidine (50 mg, 0.4 mmol) in dimethylformamide (2 mL) was added dropwise. The resulting mixture was stirred at room temperature for 1 h, until the substrate was consumed. The solvent was distilled off under reduced pressure and the residue purified by column chromatography (CH$_2$Cl$_2$-MeOH 10:0.5) to afford the 3-butyl-8-(6-butyl-5,7-dimethyl-[1,2,4]triazolo[1,5-a]pyrimidin-2-ylmethylsulfanyl)-7-ethyl-3,7-dihydro-purine-2,6-dione (63 mg, 65%) as white solid. Rf=0.44. $^1$H NMR (250 MHz, CDCl$_3$) δ 9.22 (1H, sbroad), 4.72 (2H, s), 4.25 (2H, q, J=7.1 Hz), 4.02 (2H, t, J=7.4 Hz), 2.73 (3H, s), 2.73-2.64 (2H, m), 2.64 (3H, s), 1.69 (2H, quint, J=7.4 Hz), 1.52-1.42 (4H, m), 1.40-1.28 (2H, m), 1.35 (3H, t, J=7.4 Hz), 0.96 (3H, t, J=7.1 Hz) and 0.89 (3H, t, J=7.4 Hz); $^{13}$C NMR (100 MHz, CDCl3) δ 164.5, 163.4, 162.5, 153.5, 150.9, 150.5, 149.9, 143.6, 122.0, 108.5, 46.3, 36.5, 31.7, 31.4, 31.0, 30.0, 29.0, 28.4, 27.9, 23.7, 22.8, 22.2, 13.9, 13.8 and 13.7. LCMS C$_{23}$H$_{32}$N$_8$O$_2$S Rt=6.197 min, m/z=484.6, purity >96%.

3-butyl-7-ethyl-8-mercaptoxanthine (15a)

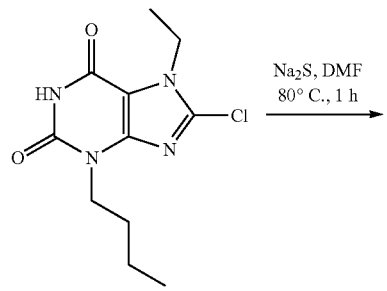

Under argon, a suspension of 3-butyl-8-chloro-7-ethylxanthine (270 mg, 1 mmol) and sodium sulfide (390 mg, 5 mmol) in dimethylformamide (20 mL) was heated at 80° C. for 1 h. The solvent was distilled off under reduced pressure and the residue was dissolved in water (30 mL), and then acidified with aqueous solution of 1N HCl until pH=4-5. The precipitate was collected by filtration and successively washed with H$_2$O and Et$_2$O to afford the 3-butyl-7-ethyl-8-mercaptoxanthine (238 mg, 89%) as white powder. $^1$H NMR (250 MHz, DMSO-d6) δ 11.28 (1H, sbroad), 4.23 (2H, q, J=7.2 Hz), 3.79 (2H, t, J=7.4 Hz), 1.56-1.42 (2H, m), 1.38-1.27 (2H, m), 1.22 (3H, t, J=7.2 Hz) and 0.90 (3H, t, J=7.4 Hz).

3-Butyl-8-chloro-7-ethylxanthine (12c)

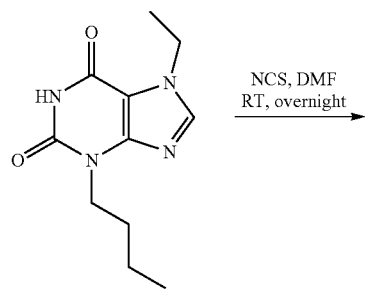

Under argon, to a solution of 3-butyl-7-ethylxanthine (1.0 g, 4.2 mmol) in dimethylformamide (30 mL) was added N-chlorosuccinimide (622 mg, 4.6 mmol) by solid fraction. The resulting mixture was stirred at room temperature overnight. The solvent was distilled off under reduced pressure and the residue was dissolved in CH$_2$Cl$_2$ (50 mL), then washed with H$_2$O. The solvent was distillated off under reduced pressure to afford the 3-butyl-8-chloro-7-ethylxanthine (1.1 g, quantitative) as white solid. $^1$H NMR (250 MHz, MeOD) δ 4.38 (2H, q, J=7.3 Hz), 3.98 (2H, t, J=7.3 Hz), 1.71 (2H, quint, J=7.3 Hz), 1.45-1.32 (5H, m) and 0.97 (3H, t, J=7.3 Hz).

3-Butyl-7-ethylxanthine (6a)

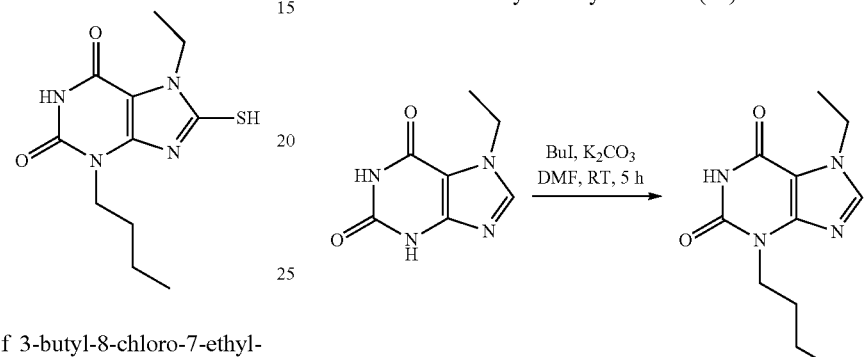

To a suspension of 7-ethylxanthine (3.61 g, 10 mmol) and potassium carbonate (3.04 g, 11 mmol) in dimethylformamide (300 mL) was injected butyl iodide (2.28 mL, 10 mmol). The mixture was stirred at room temperature for 5 h, until the complete consumption of substrate. The solvent was distilled off under reduced pressure and the residue was partitioned between CH$_2$Cl$_2$ (100 mL) and aqueous solution of 1N HCl. The aqueous layer was extracted with CH$_2$Cl$_2$ (3×20 mL) and the combined organic layers were dried over Na$_2$SO$_4$. The solvent was distilled off under reduced pressure until a few volume (15 mL) and a mixture Et$_2$O-petroleum 2:1 (150 mL) was added to allow a precipitation. The solid was collected by filtration affording the 3-butyl-7-ethylxanthine (2.58 g, 73%) as light yellow solid. $^1$H NMR (400 MHz, CDCl$_3$) δ 9.14 (1H, sbroad), 7.60 (1H, s), 4.33 (2H, q, J=7.2 Hz), 4.08 (2H, t, J=7.5 Hz), 1.75 (2H, quint, J=7.5 Hz), 1.53 (3H, t, J=7.2 Hz), 1.90 (2H, sex, J=7.5 Hz) and 0.95 (3H, t, J=7.5 Hz); $^{13}$C NMR (100 MHz, CDCl$_3$) δ 154.7, 150.9, 150.7, 140.7, 107.3, 42.7, 42.4, 30.2, 19.9, 16.4 and 13.7. HRMS (ESI+) for C$_{11}$H$_{17}$N$_4$O$_2$ (M+H) calcd, 237.1346; found, 237.1345.

7-Ethylxanthine (3a)

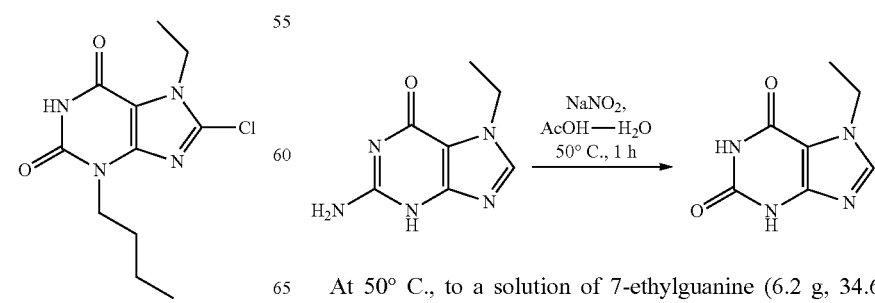

At 50° C., to a solution of 7-ethylguanine (6.2 g, 34.6 mmol) in a mixture of acetic acid (50 mL) and water (5 mL) was added dropwise a solution of sodium nitrite (9.6 g, 0.14 mol) in water (15 mL) over a period of 15 min. After addition the reaction mixture was stirred for 1 h then concentrated under reduced pressure. The residue was poured into cold H₂O (50 mL) and the precipitate collected by filtration was dried to afford 7-ethylxanthine (5.53 g, 89%) as white solid. ¹H NMR (250 MHz, DMSO-d6) δ 11.54 (1H, sbroad), 10.86 (1H, sbroad), 7.97 (1H, s), 4.20 (2H, q, J=7.1 Hz) and 1.37 (3H, t, J=7.1 Hz). HRMS (ESI+) for C₇H8N₄O₂(M+H) calcd, 181.0720; found, 181.0720.

7-ethylguanine (1c)

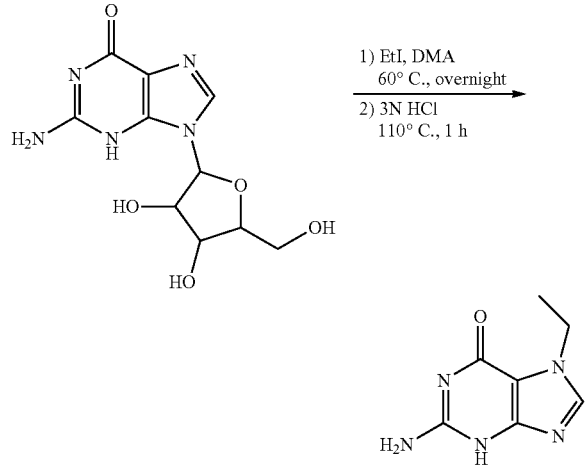

Under argon, a suspension of guanosine (10 g, 35.5 mmol) and ethyl iodide (6.8 mL, 85 mmol) in dimethylacetamide (100 mL) was heated at 60° C. overnight. Then reaction mixture was diluted with aqueous 3N HCl (90 mL) and heated at 110° C. for 1 h. The resulting solution was then treated with aqueous 10% NH₃ until pH>8 to allow the precipitation. The solid was collected by filtration and washed with Et₂O to afford 7-ethylguanine (6.16 g, 95%) as light brown powder. ¹H NMR (250 MHz, DMSO-d6) δ 7.95 (1H, s), 4.17 (2H, q, J=7.0 Hz) and 1.32 (3H, t, J=7.0 Hz); ¹³C NMR (63 MHz, DMSO-d6) δ 155.6, 151.5, 149.7, 142.1, 106.2, 41.5 and 16.4.

Example 3: 3-Butyl-8-(5,7-dimethyl-[1,2,4]triazolo[1,5-a]pyrimidin-2-ylsulfanyl)-7-ethyl-3,7-dihydro-purine-2,6-dione (28b)

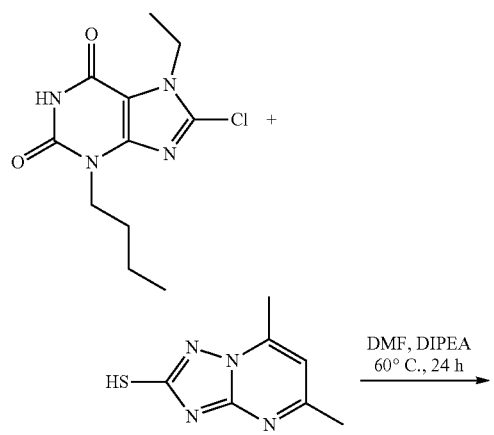

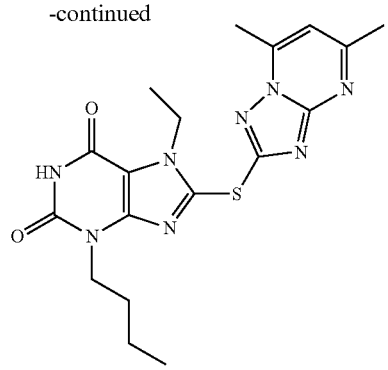

To a solution of 5,7-dimethyl-[1,2,4]triazolo[1,5-a]pyrimidine-2-thiol (58 mg, 0.32 mmol) in dimethylformamide (2 mL) was injected diisopropylethylamine (55 µL, 0.32 mmol). After 10 min under stirring, a solution of 3-butyl-8-chloromethyl-7-ethylxanthine (43 mg, 0.16 mmol) in dimethylformamide (2 mL) was added dropwise. The mixture was heated at 60° C. for 24 h then allowed to cool at room temperature. Na₂S₂O₄ was added in solid fraction and the resulting mixture was stirred at room temperature for additional 3 h. The solvent was distillated off under reduced pressure and the residue was purified by column chromatography (EtOAc-MeOH 10:0.5) to afford the 3-butyl-8-(5,7-dimethyl-[1,2,4]triazolo[1,5-a]pyrimidin-2-ylsulfanyl)-7-ethyl-3,7-dihydro-purine-2,6-dione (28 mg, 43%) as white solid. Rf=0.40. ¹H NMR (250 MHz, CDCl₃) δ 8.27 (1H, sbroad), 6.80 (1H, s), 4.53 (2H, q, J=7.1 Hz), 4.08 (2H, t, J=7.4 Hz), 2.72 (3H, s), 2.63 (3H, s), 1.80-1.63 (4H, m), 1.47 (3H, t, J=7.3 Hz), 1.38 (2H, sex, J=7.3 Hz) and 0.92 (3H, t, J=7.4 Hz).

Use of Compounds According to the Invention

Material and Methods

Example 4: HTRF Assay

HTRF assays were performed in white 384 Well Small Volume™ HiBase Polystyrene Microplates (Greiner) with a total working volume of 20 µL. Compounds were dispensed, with 200 nL per well (1% final DMSO), from a concentration stock of 1 mM in 100% DMSO and with serial DMSO dilutions, using a Mosquito Crystal pipetting robot platform (TTP labtech). The IC₅₀ measurements were performed in triplicates (Table 2 and 3). All HTRF reagents were purchased from CisBio Bioassays and reconstituted according to the supplier protocols. For each assay 14.7 µL of mix 1 (protein+peptide) is added in the assay wells, containing previously dispensed inhibitors, according to the final concentration and buffer described in Table 4, using a Biomek NX MC pipetting robot (Beckman). Then, 5.1 µL of mix 2 (donnor+acceptor) is added. HTRF signals were measured, after a final incubation (overnight at room temperature), using a PHERAstar FS (BMG Labtech) with an excitation filter at 337 nm and fluorescence wavelength measurement at 620 and 665 nm, an integration delay of 60 µs and an integration time of 500 µs. Results were analyzed with a two-wavelengths signal ratio: [intensity (665 nm)/intensity (620 nm)]*10⁴. Percentage of inhibition was calculated using the following equation: % inhibition=[(compound signal)−(min signal)]/[(max signal)−(min signal)]*100, where 'max signal' is the signal ratio with the compound vehicle alone (DMSO) and 'min signal' the signal ratio without peptide. For IC₅₀ measurements, values were normalized and fitted with Prism (GraphPad software) using the following equation: $Y=100/(1+((X/IC_{50})^{Hill\ slope}))$.

TABLE 2

Effect of various compounds of invention on BRD4(BD1) activity[a]

| Cmpd (IC$_{50}$ µM) | Cmpd (IC$_{50}$ µM) | Cmpd (IC$_{50}$ µM) | Cmpd (IC$_{50}$ µM) | Cmpd (IC$_{50}$ µM) | Cmpd (IC$_{50}$ µM) |
|---|---|---|---|---|---|
| 1a (NC) | 1b (NC) | 1c (NC) | 2a (NC) | 2b (NC) | 2c (NC) |
| 3a (NC) | 3b (NC) | 3c (NC) | 4a (NC) | 4b (9) | 4c (NC) |
| 5a (70.3 ± 4.9) | 5b (52.5 ± 7.3) | 5c (NC) | 6a (13.0 ± 0.3) | 6b (11.9 ± 0.6) | 6c (2.6 ± 0.1) |
| 7a (2.6 ± 0.1) | 7b (2.6 ± 0.1) | 7c (17.9 ± 1.3) | 8a (NC) | 8b (NC) | 8c (10.7 ± 0.4) |
| 9a (NC) | | | | | 10c (NC) |
| | 11b (NC) | 11c (NC) | 12a (NC) | 12b (<100) | 12c (NC) |
| | | | | | 14c (<100) |
| 15a (35.1 ± 2.9) | 15b (ND) | 15c (100) | 16a (NC) | | |
| 17a (NC) | 17b (NC) | 17c (NC) | 18a (NC) | 18b (NC) | 18c (NC) |
| 19a (93.3 ± 16.6) | | 19c (NC) | 20a (ND) | 20b (ND) | 21a (45.6 ± 4.9) |
| 21b (89.1 ± 9.3) | 22a (26.4 ± 0.7) | 22b (NC) | 23a (NC) | 23b (NC) | 24a (NC) |
| 24b (69.6 ± 5.2) | 25a (12.6 ± 0.3) | 25b (46.6 ± 4.6) | 26a (7.9 ± 0.2) | 26b (5.0 ± 0.1) | 27a (100) |
| 27b (20.4 ± 3.6) | 28a (NC) | 28b (NC) | 29a (NC) | 29b (ND) | 30a (18.3 ± 1.4) |
| 30b (ND) | 31a (46.8 ± 7.8) | 31b (59.6 ± 7.8) | 32a (54.0 ± 4.8) | | |

[a]Drug concentration that inhibits protein-protein interaction by 50%. Data are the mean ± standard deviation (SD) of three experiments.
NC abbreviation stands for Not Converged (IC$_{50}$ > maximal concentration of compound used).
ND abbreviation stands for Not Determined.

Example 4 Bis: HTRF Assay

After the efficient synthesis of the focused library in 96 well plates with the Accelerator Synthetizer SLT100, the focused library has been directly transferred to a Labcyte Access/Echo® Laboratory Workstation to assess the compounds for their ability to disrupt bromodmain/histone complexes using the homogeneous time-resolved fluorescence (HTRF®) technology (IC50 µM, table 2bis).

TABLE 2 bis

Effect of various compounds of invention on BRD4(BD1) activity[a]

| | HTRF (IC$_{50}$, µM) |
|---|---|
| 33 | 8.5 |
| 34 | 44.5 |
| 35 | 19.2 |
| 36 | 3 |
| 37 | 16.6 |
| 38 | 48.2 |
| 39 | 38.2 |
| 40 | 33 |
| 41 | 6.4 |
| 42 | 45.3 |
| 43 | 33.4 |
| 44 | 21.9 |
| 45 | 11.6 |
| 46 | 20.1 |
| 47 | 30.1 |
| 48 | 35.2 |
| 49 | 35.1 |
| 51 | 30.2 |
| 52 | 33.04 |
| 53 | 4.4 |
| 54 | 7.1 |
| 55 | 14.2 |
| 56 | 13.2 |
| 57 | 7.5 |
| 58 | 2.7 |
| 59 | 6.9 |
| 60 | 8.4 |
| 61 | 4.7 |
| 62 | 8.9 |
| 63 | 8.9 |
| 64 | 5.1 |
| 65 | 32.7 |
| 66 | 16.8 |
| 67 | 8.9 |
| 68 | 35.5 |
| 69 | 8.4 |
| 70 | 6.5 |
| 71 | 17.8 |
| 72 | 4.4 |
| 73 | 7.5 |
| 74 | 5.5 |
| 75 | 3.9 |
| 76 | 12.7 |
| 77 | 26.8 |
| 78 | 15.7 |
| 79 | 4.2 |
| 80 | 10.6 |

[a]Drug concentration that inhibits protein-protein interaction by 50%.

Example 5: Bromodomain Selectivity Profiles

Selectivity profiles of bromodomain inhibitors were performed as described in HTRF screen section. Concentration of histone peptide was optimized to ensure sufficient signal to noise ratio, sufficient sensitivity for detection of weak inhibitors and comparable data from one bromodomain to another. HTRF detection reagents (EPIgeneous™ Binding Domain kits) were purchased from Cisbio Bioassays and used according to supplier's protocol. GST tagged bromodomain proteins were purchased from BPS Bioscience and histone peptide from Anaspec.

TABLE 3

Selectivity profiles of compounds of invention towards the BET

| Bromodomain | IC$_{50}$ (µM)[a] | | | | | | | |
|---|---|---|---|---|---|---|---|---|
| | 4b | 6a | 7a | 22a | 25a | 26a | 26b | 27b[c] |
| BRD4(BD1) | 9 | 13.0 ± 0.3 | 2.6 ± 0.1 | 26.4 ± 0.7 | 12.6 ± 0.3 | 7.9 ± 0.2 | 5.0 ± 0.1 | 20.4 ± 3.6 |
| BRD3(BD1) | 14 | 4.8 ± 0.3 | 1.8 ± 1.1 | 31.7 ± 1.1 | 40.7 ± 2.2 | 43.5 ± 7.1 | 62.0 ± 7.8 | NC |
| BRD2(BD1) | NC | 18.8 ± 0.7 | 4.7 ± 0.1 | 30.0 ± 0.9 | 30.1 ± 1.3 | 31.9 ± 0.5 | 59.0 ± 2.9 | NC |
| BRDT(BD1) | 27 | 7.9 ± 0.4 | 2.3 ± 0.2 | >100 | 65.3 ± 8.1 | 42.5 ± 3.9 | >100 | NC |
| BRD4(BD2) | 5 | 8.1 ± 0.3 | 1.9 ± 0.1 | NC[d] | >100 | >100 | NC | NC |
| BRD3(BD2) | 4 | 5.8 ± 0.2 | 1.8 ± 0.2 | NC[d] | 23.9 ± 1.4 | 2.1 ± 0.5 | NC | NC |
| BRD2(BD2) | 7 | 6.6 ± 0.3 | 1.6 ± 0.2 | NC[d] | NC | 9.5 ± 0.5 | NC | NC |
| ATAD2[b] | ND | NC | NC | NC | >100 | 56.4 ± 7.9 | >100 | NC |

[a]Drug concentration that inhibits protein-protein interaction by 50%. Data are the mean ± standard deviation (SD) of three experiments. NC abbreviation stands for Not Converged. ND abbreviation stands for Not Determined.
[b]ATAD2 is used as a non-BET family member bromodomain control.
[c]Data above 25 µM have been excluded due to precipitation and fluorescence interference at 620 nm.
[d]Fluorescence interference at 620 nm with BD2.

TABLE 4

HTRF selectivity experimental procedures[a]

| | MIX 1 | | | MIX 2 | | | Assay | |
|---|---|---|---|---|---|---|---|---|
| Protein name | (nM) | Peptide name | (nM) | Donnor name | (nM) | Acceptor name | (nM) buffer[b] | DMSO |
| GST-BRD4(BD1) | 5 | H4 KAc 5/8/12/16 peptide | 25 | MAb Anti GST-Keu | 0.5 | Streptavidin d2 | 3.125 Buffer A | 1% |
| GST-BRD3(BD1) | 5 | H4 KAc 5/8/12/16 peptide | 10 | MAb Anti GST-Keu | 0.5 | Streptavidin d2 | 1.25 Buffer A | 1% |
| GST-BRD2(BD1) | 5 | H4 KAc 5/8/12/16 peptide | 15 | MAb Anti GST-Keu | 0.5 | Streptavidin d2 | 1.875 Buffer A | 1% |
| GST-BRDT(BD1) | 5 | H4 KAc 5/8/12/16 peptide | 50 | MAb Anti GST-Keu | 0.5 | Streptavidin XL665 | 6.3 Buffer A | 1% |
| GST-BRD4(BD2) | 5 | H4 KAc 5/8/12/16 peptide | 75 | MAb Anti GST-Keu | 0.5 | Streptavidin XL665 | 9.375 Buffer A | 1% |
| GST-BRD3(BD2) | 5 | H4 KAc 5/8/12/16 peptide | 150 | MAb Anti GST-Keu | 0.5 | Streptavidin XL665 | 18.75 Buffer A | 1% |
| GST-BRD2(BD2) | 5 | H4 KAc 5/8/12/16 peptide | 25 | MAb Anti GST-Keu | 0.5 | Streptavidin XL665 | 3.125 Buffer A | 1% |
| GST-ATAD2 | 5 | H4 KAc 5/8/12/16 peptide | 10 | MAb Anti GST-KTb | 0.5 | Streptavidin XL665 | 10 Buffer B | 1% |

[a]For each bromodomain, concentrations of protein, peptide, donor and acceptor have been optimized and are presented in this summary table also indicating the donor and acceptor type as well as the final DMSO concentration and buffer composition.
[b]Buffer A: 50 mM KPO$_4$, pH 7, 100 mM KF, BSA 0.1%; Buffer B: 50 mM Hepes, pH 7.5, 150 mM NaCl, BSA 0.1%.

Example 6: Cell-Based Assays

Cells and Cell Culture

The human leukemia cell line Jurkat (ATCC® TIB-152) was maintained in RPMI-1640 medium supplemented with 10% FBS at 37° C. and 5% CO$_2$. Human osteosarcoma cell line (U2OS, ATCC® HTB-96™) was maintained in DMEM supplemented with 10% FBS at 37° C. and 5% CO$_2$.

Cytotoxicity Experiments

In antiproliferative assays, compounds were assayed for their growth inhibiting activity towards the described cancer cell lines using the Cell Titer-Glo Luminescent Cell Viability Assay as described by the manufacturer (Promega Corporation). Briefly, 104 cells were plated onto 96 well-plates (white with clear bottom (3610, Corning Costar)) in 100 µL media per well immediately before assay. Compounds were added at different concentrations (ranging from 100 to 0.05 µM) to each well and cell cultures were incubated 37° C. during 72 h. Vehicle (DMSO) was used as control and all compounds were tested in constant percentage of DMSO (1%). After addition of 50 µL Cell Titer-GLO, Luminescence was measured using a Centro luminometer LB960 (Berthold). Dose-response curves were generated and effective dose 50 values (EC$_{50}$) were calculated using non-linear regression analysis (Graph Pad Prism).

Western Blot

Non-treated Jurkat cells and Jurkat cells treated during 24 h with compound of the invention 26b, or DMSO were lysed in RIPA lysis buffer (Tris HCl pH=7.5 50 mM, NaCl 150 mM, Triton 1%, SDS 0.1%, sodium deoxycholate 1%) supplemented with protease inhibitor cocktail (P8340, Sigma-Aldrich) and 1 mM PhenylMethylSulfonyl Fluoride (Sigma-Aldrich). 75 µg of protein were loaded onto 10% acrylamide SDS/PAGE and then transferred to nitrocellulose Hybond C-extra membranes, 45 micron (GE Healthcare). The membranes were saturated with 5% (wt/vol) skim milk in TBST [Tris-buffered saline/0.1% (vol/vol) Tween 20] 1 h at room temperature and incubated with anti-myc antibody (clone 9E10, sc40 Santa Cruz) at a 1:500 dilution in 0.5% (wt/vol) skimmed milk in TBST overnight at 4° C. Membranes were then washed with TBST, incubated with an HRP-conjugated anti-mouse secondary antibody (polyclonal goat anti mouse P0447, Pierce) at a 1:20,000 dilution in TBST 1 h at room temperature. Immunoreactive bands were revealed using SuperSignal™ West Pico Extended Duration Substrate (Pierce) detection reagents. Quantification was performed using ImageJ software.

Figure 1B:
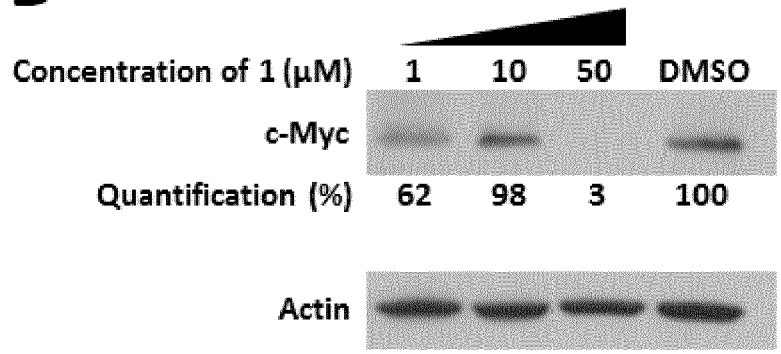

In cell-based assays, 26b reduced Jurkat T cells viability in a dose-dependent manner with an $EC_{50}$ of 27 µM. Also, 26b down regulated c-Myc, a pro-oncogene contributing to the pathogenesis of numerous human cancers, in the same range of concentration (FIGS. 1A and 1B).

Example 7: Specific Structural Elements of BET Protein Having a Key Role in the Selectivity The Inventors follow-up on of a previous mid-throughput screen (MTS) using the 2P213D chemical library, a structurally diverse 'protein-protein interaction inhibition (2P2I)-oriented' collection of compounds[18-23] by focusing on a selective BRD4 (BD1) acetylated-mimic xanthine inhibitor. Among the 17 hits that were identified following this screen, one xanthine derivative was found to present a low micromolar $IC_{50}$ measured by homogeneous time resolved fluorescence (HTRF) and an unforeseen selectivity profile among the BET family members. A structure-based investigation program around xanthine scaffold containing compounds was the starting point of this observed selectivity with a key role identified for the bromodomains ZA loop.

Results and Discussion

An MTS of the $2P2I_{3D}$ chemical library against BRD4 (BD1), identified 17 hits with affinities within the low micromolar range.[23] The inventors set-up isothermal titration calorimetry (ITC) as orthogonal assay and were able to validate a direct binding for 7 out of the 17 compounds tested, with ligand efficiency (LE) values ranging from 0.20 up to 0.23. Among them, 3-butyl-8-(6-butyl-5,7-dimethyl-[1,2,4]triazolo[1,5-a]pyrimidin-2-ylsulfanylmethyl)-7-ethylxanthine (26b), a xanthine derivative, presented a Kd of 1.4 µM, driven by a large favorable entropy term (−TΔS of −7.1 Kcal/mol) as demonstrated by ITC. This biophysical result suggested conformational changes and water rearrangement upon binding of the compound. Moreover, an HTRF experiment against seven out of the eight BD1 and BD2 BET domains (BRDT (BD2) was not available from the company Cisbio) pinpointed a 10 fold lower $IC_{50}$ for 3-butyl-8-(6-butyl-5,7-dimethyl-[1,2,4]triazolo[1,5-a]pyrimidin-2-ylsulfanylmethyl)-7-ethylxanthine (26b) towards BRD4(BD1) ($IC_{50}$ of 5 µM) as compared to its relatives BD1 ($IC_{50}$'s>50 µM), and no detectable inhibition of the BD2 counterparts (Table 3). In cell-based assays, 3-butyl-8-(6-butyl-5,7-dimethyl-[1,2,4]triazolo[1,5-a]pyrimidin-2-ylsulfanylmethyl)-7-ethylxanthine (26b) reduced Jurkat T cells viability in a dose-dependent manner with an $EC_{50}$ of 27 µM. Also, 3-butyl-8-(6-butyl-5,7-dimethyl-[1,2,4]triazolo[1,5-a]pyrimidin-2-ylsulfanylmethyl)-7-ethylxanthine (26b) down regulated c-Myc, a pro-oncogene contributing to the pathogenesis of numerous human cancers, in the same range of concentration. The Inventors next solved the crystal structure of 3-butyl-8-(6-butyl-5,7-dimethyl-[1,2,4]triazolo[1,5-a]pyrimidin-2-ylsulfanylmethyl)-7-ethylxanthine (26b) in complex with BRD4(BD1). The co-crystal revealed the globular domain organization for BRD4(BD1),[24] and a well-defined electron density for 3-butyl-8-(6-butyl-5,7-dimethyl-[1,2,4]triazolo[1,5-a]pyrimidin-2-ylsulfanylmethyl)-7-ethylxanthine (26b) with the expected binding mode of an acetyl-lysine mimetic[25] forming the canonical hydrogen bond with the conserved asparagine N140 and a water mediated hydrogen bond with Y97 also linking the inhibitor to the conserved water network at the bottom of the binding pocket. Surprisingly, the triazolopyrimidinyl moiety stacked against the ZA channel, occupying the space at the rim of the acetyl-lysine binding site, a binding mode that has also recently been reported for benzimidazolone derivative inhibitors targeting BAZ2B bromodomain.[26-28] This triazolo moiety establishes a hydrogen bond interaction with the main chain (NH amido group) of D88 a residue conserved throughout the BET family. This interaction orientates the triazolopyrimidinyl fragment in the ZA channel while its ring system is locked from one side by van der Walls contacts with L92, and from the other side with Q85—the pyrimidine ring sits tightly on this glutamine which is bent by 90° to adopt this complementary orientation. This BD1-conserved amino acid (except in BRDT (BD1)) is replaced by larger residues such as arginine or lysine in the BD2 sub-family. This difference could be responsible for the observed selectivity profile of 3-butyl-8-(6-butyl-5,7-dimethyl-[1,2,4]triazolo[1,5-a]pyrimidin-2-ylsulfanylmethyl)-7-ethylxanthine (26b) towards BRD4-BRD3-BRD2-(BD1) vs all the other BET tested.

In order to gain better understanding of this selectivity profile, the Inventors undertook a structure-based program aiming to define the structure/affinity and structure/selectivity relationships by decomposing this model compound.

The xanthine 2b and the corresponding mono- and unsymmetrically dialkylated derivatives 3a, 6a, and 7a were further analyzed by HTRF, ITC, and x-ray crystallography, when available (Table 1' and table 2). Chemical variations of the xanthine mimicking the reference probe ((6S)-4-(4-chlorophenyl)-2,3,9-trimethyl-6H-thieno[3,2-f][1,2,4]triazolo[4,3-a][1,4]diazepine-6-acetic acid 1,1-dimethylethyl ester (JQ1, PDB accession code 3MXF),[24] such as a substitution of the butyl group (compound 6a) by a chlorobenzyl one (compound 7a) allowed an optimization of the core with an $IC_{50}$ of 2.6 µM as measured by HTRF (2 fold increased potency) and a Kd of 1.8 µM as measured by ITC. This optimized core presented a favorable enthalpy change of −6.3 kcal/mol. More importantly, the selectivity profile of this optimized core 7a displayed a pan-BET inhibition profile, similarly to 6a. Analysis of the co-crystal structures confirmed a characteristic recognition of the pocket by this core, as exemplified by the superimposition of 3-butyl-8-(6-butyl-5,7-dimethyl-[1,2,4]triazolo[1,5-a]pyrimidin-2-ylsulfanylmethyl)-7-ethylxanthine (26b) with 7a. The core was thus not responsible (as expected) for the observed selectivity profiles of 3-butyl-8-(6-butyl-5,7-dimethyl-[1,2,4]triazolo[1,5-a]pyrimidin-2-ylsulfanylmethyl)-7-ethylxanthine (26b).

The Inventors next questioned whether the observed selectivity profile of 3-butyl-8-(6-butyl-5,7-dimethyl-[1,2,4]triazolo[1,5-a]pyrimidin-2-ylsulfanylmethyl)-7-ethylxanthine (26b) was due to the triazolo and/or to the pyrimidinyl moiety of the core extension. To address this purpose, a series of N-3, N-7 disubstituted triazoloxanthine derivatives 3-butyl-8-(6-butyl-5,7-dimethyl-[1,2,4]triazolo[1,5-a]pyrimidin-2-ylsulfanylmethyl)-7-ethylxanthine (26b) and 8-(6-Butyl-5,7-dimethyl-[1,2,4]triazolo[1,5-a]pyrimidin-2-ylsulfanylmethyl)-3-(4-chlorobenzyl)-7-ethyl-3,7-dihydro-purine-2,6-dione (27b), 8-(5-Amino-1H-[1,2,4]triazol-3-ylsulfanylmethyl)-3-(4-chlorobenzyl)-7-ethyl-3,7-dihydro-purine-2,6-dione (22a), 8-(5-Amino-1H-[1,2,4]triazol-3-ylsulfanylmethyl)-3-butyl-7-ethyl-3,7-dihydro-purine-2,6-dione (21b) were synthesized.

After evaluation, compound 8-(5-Amino-1H-[1,2,4]triazol-3-ylsulfanylmethyl)-3-(4-chlorobenzyl)-7-ethyl-3,7-dihydro-purine-2,6-dione (22a) revealed an $IC_{50}$ of 26.4 µM in HTRF which represents a 10-fold decrease in potency as compared to 7a (Table 2, table 2' and table 3). Compound 8-(5-Amino-1H-[1,2,4]triazol-3-ylsulfanylmethyl)-3-(4-chlorobenzyl)-7-ethyl-3,7-dihydro-purine-2,6-dione (22a), however, exhibited a shift of selectivity towards BET-BD1 domains (Table 3). The introduction of the triazolo fragment was thus bringing a decrease of potency, yet driving a commencement of selectivity among BET bromodomains (BD1 vs BD2).

A potential hydrogen bond between the triazolo fragment and D88, conserved in all the BET bromodomains, could be stabilized with certain bromodomains and not with others, due to differences in the dynamics of the ZA loop, which has been demonstrated to be crucial in the binding kinetics of several BET-BRDi.[24,31,32] Superimposition of BRD4 with or without compound 3-butyl-8-(6-butyl-5,7-dimethyl-[1,2,4]triazolo[1,5-a]pyrimidin-2-ylsulfanylmethyl)-7-ethylxanthine (26b) illustrates structural rearrangements with displacement of the ZA loop up to 2.7 Å. These rearrangements are not observed with the 'pan inhibitor' xanthine scaffold derivative (compound 7a), thus validating this assumption. The role of this loop and its associated variable dynamics would also explain the $IC_{50}$ observed for 3-butyl-8-(6-butyl-5,7-dimethyl-[1,2,4]triazolo[1,5-a]pyrimidin-2-ylsulfanylmethyl)-7-ethylxanthine (26b) towards BRD4(BD1) vs BRD3 (BD1) and BRD2(BD1), this hydrogen bond being more stable with BRD4(BD1). Analysis of the protein-ligand(s) interactions including hydrophobic and hydrogen-bonding contacts was carried out using LigPlot+.[33] This weak interaction prevented us from solving a non-ambiguous 3D structure of 8-(5-Amino-1H-[1,2,4]triazol-3-ylsulfanylmethyl)-3-(4-chlorobenzyl)-7-ethyl-3,7-dihydro-purine-2,6-dione (22a) in complex with BRD4(BD1). However, crystals with 50% occupancy of 8-(5-Amino-1H-[1,2,4]triazol-3-ylsulfanylmethyl)-3-(4-chlorobenzyl)-7-ethyl-3,7-dihydro-purine-2,6-dione (22a) highlighted that this compound was still interacting with BRD4(BD1) and that hydrogen bond between the triazolo moiety and the main chain (NH amido group) of D88 was present, with BRD4(BD1). The triazolo was thus explaining only partly the observed selectivity profiles of 3-butyl-8-(6-butyl-5,7-dimethyl-[1,2,4]triazolo[1,5-a]pyrimidin-2-ylsulfanylmethyl)-7-ethylxanthine (26b). An explanation for the selectivity profile of 3-butyl-8-(6-butyl-5,7-dimethyl-[1,2,4]triazolo[1,5-a]pyrimidin-2-ylsulfanylmethyl)-7-ethylxanthine (26b) was finally confirmed with the synthesis of 8-(6-Butyl-5,7-dimethyl-[1,2,4]triazolo[1,5-a]pyrimidin-2-ylsulfanylmethyl)-3-(4-chlorobenzyl)-7-ethyl-3,7-dihydro-purine-2,6-dione (27b), the N-chlorobenzyl analogue of 3-butyl-8-(6-butyl-5,7-dimethyl-[1,2,4]triazolo[1,5-a]pyrimidin-2-ylsulfanylmethyl)-7-ethylxanthine (26b). Of note, this compound was found to be less active than the original compound 3-butyl-8-(6-butyl-5,7-dimethyl-[1,2,4]triazolo[1,5-a]pyrimidin-2-ylsulfanylmethyl)-7-ethylxanthine (26b) ($IC_{50}$ values of 20 µM vs 5 µM, respectively). However, the selectivity profile of this compound was similar to that of 3-butyl-8-(6-butyl-5,7-dimethyl-[1,2,4]triazolo[1,5-a]pyrimidin-2-ylsulfanylmethyl)-7-ethylxanthine (26b), i.e., selective towards BRD4(BD1). Altogether, these data suggest that the $N_3,N_7$-dialkylated xanthine core (see 6a and 7a) is responsible for the pan-BET inhibition while condensed with triazolo moiety (see 8-(5-Amino-1H-[1,2,4]triazol-3-ylsulfanylmethyl)-3-(4-chlorobenzyl)-7-ethyl-3,7-dihydro-purine-2,6-dione (22a) it allows the preferential inhibition of BET-BD1 domains forming a hydrogen bond with the conserved D88 residue. Further condensation with pyrimidinyl moiety drives the corresponding triazolopyrimidinyl xanthine derivatives (3-butyl-8-(6-butyl-5,7-dimethyl-[1,2,4]triazolo[1,5-a]pyrimidin-2-ylsulfanylmethyl)-7-ethylxanthine (26b) and 8-(6-Butyl-5,7-dimethyl-[1,2,4]triazolo[1,5-a]pyrimidin-2-ylsulfanylmethyl)-3-(4-chlorobenzyl)-7-ethyl-3,7-dihydro-purine-2,6-dione (27b) to be selective towards BRD4(BD1) due to van der Waals interaction with the side chain of Q85. A steric clash prevents this interaction with the R present at the same position in BRDT(BD1) or the K present in the other BRDX(BD2) bromodomains. These findings suggest potential mechanism for the selectivity of BET bromodomains.

CONCLUSION

In this study, the Inventors investigated the key structural feature responsible for the selectivity of a xanthine-based BRD4(BD1) inhibitor identified through MTS.

This compound represents the first low micromolar selective inhibitor targeting BRD4(BD1) with a >10-fold ratio in binding affinity towards any other BET bromodomain tested, yet presenting low but dose-response down regulation of c-Myc levels in cell-based assay. The co-crystal structure revealed an original orientation of the triazolopyrimidinyl moiety, expanding into the ZA channel, setting the basis of a structure-selectivity relationship inside the BET family. Even though it is conserved throughout the BET family, the different dynamic behavior of the ZA loop could be exploited to tune the selectivity of BET inhibitors.

TABLE 1'

Effect of various substituted xanthine on BRD4(BD1) activity

| | Substituent | | | | BRD4(BD1) | | |
|---|---|---|---|---|---|---|---|
| Compd | $R_1$ | $R_3$ | $R_7$ | $R_8$ | $IC_{50}$ (µM)$^a$ | $K_D$ (µM)$^b$ | LE$^c$ |
| 2b | H | H | H | H | NA | — | NA |
| 3a | H | H | Et | H | NA | — | NA |
| 6a | H | Bu | Et | H | 13.0 ± 0.3 | — | 0.40 |
| 7a | H | 4-ClBn | Et | H | 2.6 ± 0.1 | 1.8 | 0.37 |

$^a$Drug concentration that inhibits protein-protein interaction by 50%. Data are the mean ± standard deviation (SD) of three experiments.
$^b$Kd determined by Isothermal Titration Calorimetry.
$^c$Ligand Efficiency (LE) defined as the ratio of the log of the $IC_{50}$ to the number (N) of non-hydrogen atoms of the compound LE = 1.4(−log($IC_{50}$)/N).

TABLE 2

Effect of various triazolo-substituted xanthine derivatives on BRD4(BD1) activity

| | Substituent | | | | BRD4(BD1) | | |
|---|---|---|---|---|---|---|---|
| Cmpd | $R_1$ | $R_3$ | $R_7$ | $R_8$ | $IC_{50}$ (µM)$^a$ | $K_D$ (µM)$^b$ | LE$^c$ |
| 21b | H | Bu | Et | (triazole-SCH$_2$ with NH and NH$_2$ substituents) | >50 | — | NA |

TABLE 2-continued

Effect of various triazolo-substituted xanthine derivatives on BRD4(BD1) activity

| Cmpd | $R_1$ | $R_3$ | $R_7$ | $R_8$ | $IC_{50}$ (μM)[a] | $K_D$ (μM)[b] | LE[c] |
|---|---|---|---|---|---|---|---|
| 22a | H | 4-ClBn | Et | (3-amino-5-methylthio-1H-1,2,4-triazole) | 26.4 ± 0.7 | — | 0.17 |
| 26b | H | Bu | Et | (2-methylthio-5,7-dimethyl-6-butyl-[1,2,4]triazolo[1,5-a]pyrimidine) | 5.0 ± 0.1 | 1.4 | 0.22 |
| 27b | H | 4-ClBn | Et | (2-methylthio-5,7-dimethyl-6-butyl-[1,2,4]triazolo[1,5-a]pyrimidine) | 20.4 ± 3.6 | — | 0.15 |

[a] Drug concentration that inhibits protein-protein interaction by 50%. Data are the mean ± standard deviation (SD) of three experiments.
[b] Kd determined by Isothermal Titration Calorimetry.
[c] Ligand Efficiency (LE) defined as the ratio of the $IC_{50}$ to the number (N) of non-hydrogen atoms of the compound LE = 1.4(-log $IC_{50}$)/N.

Protein Expression and Purification.

For Isothermal Titration Calorimetry (ITC) and crystallogenesis, BRD4(BD1) was produced and purified using a histidine tag affinity chromatography as described by Filipakopoulos et al.9 For these experiments, a pNIC28-BSA4 expression vector containing BRD4(BD1) and a Tobacco Etch Virus (TEV) protease cleavage site have kindly been provided by Stefan Knapp laboratory from the SGC at the University of Oxford. After size exclusion chromatography, the fractions presenting pure BRD4(BD1) after TEV cleavage of the histidine tag were pooled and concentrated to 25 mg/mL for crystallogenesis. For ITC assays, the protein was concentrated up to at 6 mg/mL and the DTT was removed using a buffer exchange column (PD10 from GE healthcare) equilibrated with 10 mM HEPES pH=7.5, 150 mM NaCl. For Homogeneous Time Resolved Fluorimetry (HTRF) experiments, a BRD4(BD1) synthetic gene that includes a TEV cleavage site was purchased from LifeTechnology in a pDONR transport vector before cloning into a pDESTTM15 expression vector for GST affinity purification. Protein production and purification was carried out using similar protocols and buffers as used for the His-BRD4(BD1) system. Purification was carried on GST affinity resin (Thermo Scientific) and reduced glutathione was used for protein release. GST-BRD4(BD1) was further purified by size exclusion chromatography on a Superdex 16/60 Hiload column (GE Healthcare) using 20 mM TRIS pH=8.0, 150 mM NaCl Buffer.

Isothermal Titration Calorimetry.

ITC was used to evaluate the thermodynamics parameters of the binding between BRD4(BD1) and the selected compounds, using ITC conditions previously described by Filippakopoulos et al.8 Purified BRD4(BD1) was extensively dialyzed in the ITC buffer containing 10 mM Hepes pH=7.5 and 150 mM NaCl. Compounds were diluted directly in the last protein dialysate prior to experiments. Titrations were carried out on a MicroCal ITC200 microcalorimeter (GE Healthcare, Piscataway, N.J.). Each experiment was designed using a titrant concentration (protein in the syringe) set 10 to 15 times the analyte concentration (compound in the cell generally between 10 and 35 μM) and using 13 injections at 35° C. A first small injection (generally 0.2 μL) was included in the titration protocol in order to remove air bubbles trapped in the syringe prior titration. Raw data were scaled after setting the zero to the titration saturation heat value. Integrated raw ITC data were fitted to a one site non-linear least squares fit model using the MicroCal Origin plugin as implemented in Origin 7 (Origin Lab). Finally, ΔG and TΔS values were calculated from the fitted ΔH and KA values using the equations ΔG=−R.T. ln KA and ΔG=ΔH−TΔS.

Crystallography.

BRD4(BD1)-Inhibitor co-crystallization was performed at 19° C. (292K) using the hanging drop vapor diffusion method. For the complex with 1 mM of compound 26b, 25 mg/mL of BRD4(BD1) preparation was mixed at a 1:1 ratio with the precipitant solution (200 mM ammonium sulfate, 100 mM Tris pH=8.5, 25% PEG3350) and crystals grew to diffracting quality within 3-5 days. For the complex with 2.5 mM of 7a, 16 mg/mL of BRD4(BD1) preparation was mixed at a 1:1 ratio with the precipitant solution (250 mM ammonium sulfate, 100 mM Tris pH=8.5, 19% PEG3350) and crystals grew to diffracting quality within 15 days. For the complex with 22a, 2.5 mM of compound and 12 mg/mL of BRD4(BD1) preparation was mixed at a 1:1 ratio with the precipitant solution (300 mM Na Formate, 100 mM NaCl, 22% PEG3350, 10% Ethylene glycol). Crystals grew to diffracting quality within 1 month. Crystals were cryoprotected using the precipitant solution supplemented with 10% ethylene glycol for 26b and 7a or with 10% glycerol for 22a and were flash frozen in liquid nitrogen. Data for 26b, 7a and 22a were respectively collected at the AFMB laboratory—Marseilles (Bruker AXS MICROSTAR equipped with a Mar345 detector), and on the ESRF beamlines ID23-2 and ID29. Indexing, integration and scaling were performed using XDS.10 Initial phases were calculated by molecular replacement with Phaser MR (CCP4 suite) 11 using a model of the first domain of BRD4 (extracted from the Protein Data Bank accession code: 2OSS). Initial models for the protein and the ligands were built in COOT.12 The cycles of refinement were carried out with Refmac5 (CCP4 suite). The models and structures factors have been deposited with Protein Data Bank accession code for compound 26b: 5EGU, compound 7a: 5EIS and compound 22a: 5EI4.

REFERENCES (1) Filippakopoulos, P.; Knapp, S. The bromodomain interaction module. *FEBS Lett.* 2012, 586, 2692-2704.

(2) Filippakopoulos, P.; Picaud, S.; Mangos, M.; Keates, T.; Lambert, J.-P.; Barsyte-Lovejoy, D.; Felletar, I.; Volkmer, R.; Muller, S.; Pawson, T.; Gingras, A.-C.; Arrowsmith, C. H.; Knapp, S. Histone recognition and large-scale structural analysis of the human bromodomain family. *Cell* 2012, 149, 214-231.

(3) Hewings, D. S.; Rooney, T. P.; Jennings, L. E.; Hay, D. A.; Schofield, C. J.; Brennan, P. E.; Knapp, S.; Conway, S. J. Progress in the development and application of small molecule inhibitors of bromodomain-acetyl-lysine interactions. *J. Med. Chem.* 2012, 55, 9393-9413.

(4) Kanno, T.; Kanno, Y.; Siegel, R. M.; Jang, M. K.; Lenardo, M. J.; Ozato, K. Selective recognition of acetylated histones by bromodomain proteins visualized in living cells. *Mol. Cell* 2004, 13, 33-43.

(5) Huang, H.; Zhang, J.; Shen, W.; Wang, X.; Wu, J.; Wu, J.; Shi, Y. Solution structure of the second bromodomain of Brd2 and its specific interaction with acetylated histone tails. *BMC struct. Biol.* 2007, 7, 1-12.

(6) LeRoy, G.; Rickards, B.; Flint, S. J. The double bromodomain proteins Brd2 and Brd3 couple histone acetylation to transcription. *Mol. Cell* 2008, 30, 51-60

(7) Baud, M. G.; Lin-Shiao, E.; Cardote, T.; Tallant, C.; Pschibul, A.; Chan, K. H.; Zengerle, M.; Garcia, J. R.; Kwan, T. T.; Ferguson, F. M.; Ciulli, A. Chemical biology. A bump-and-hole approach to engineer controlled selectivity of BET bromodomain chemical probes. *Science* 2014, 346, 638-641.

(8) Picaud, S.; Wells, C.; Felletar, I.; Brotherton, D.; Martin, S.; Savitsky, P.; Diez-Dacal, B.; Philpott, M.; Bountra, C.; Lingard, H.; Fedorov, O.; Müller, S.; Brennan, P. E.; Knapp, S.; Filippakopoulos, P. RVX-208, an inhibitor of BET transcriptional regulators with selectivity for the second bromodomain. *Proc. Natl. Acad. Sci. USA.* 2013, 110, 19754-19759.

(9) Schroder, S.; Cho, S.; Zeng, L.; Zhang, Q.; Kaehlcke, K.; Mak, L.; Lau, J.; Bisgrove, D.; Schnolzer, M.; Verdin, E.; Zhou, M.-M.; Ott, M. Two-pronged binding with bromodomain-containing protein 4 liberates positive transcription elongation factor b from inactive ribonucleoprotein complexes. *J. Biol. Chem.* 2012, 287, 1090-1099.

(10) Rahl, P. B.; Lin, C. Y.; Seila, A. C.; Flynn, R. A.; McCuine, S.; Burge, C. B.; Sharp, P. A.; Young, R. A. c-Myc regulates transcriptional pause release. *Cell* 2010, 141, 432-445.

(11) Belkina, A. C.; Denis, G. V. BET domain co-regulators in obesity, inflammation and cancer. *Nat. Rev. Cancer* 2012, 12, 465-477.

(12) Lovén, J.; Hoke, H. A.; Lin, C. Y.; Lau, A.; Orlando, D. A.; Vakoc, C. R.; Bradner, J. E.; Lee, T. I.; Young, R. A. Selective inhibition of tumor oncogenes by disruption of super-enhancers. Cell 2013, 153, 320-334.

(13) Boi, M.; Bonetti, P.; Ponzoni, M.; Tibiletti, M. G.; Stathis, A.; Cvitkovic, E.; Inghirami, G.; Zucca, E.; Bertoni, F. The brd-Inhibitor OTX015 shows pre-clinical activity in anaplastic large T-cell lymphoma (ALCL). *ASH Annual Meeting Abstracts, Blood* 2012, 120, 4872.

(14) Bonetti, P.; Boi, M.; Ponzoni, M.; Tibiletti, M. G.; Stahis, A.; Inghirami, G.; Noel, K.; Zucca, E.; Bertoni, F. *ASH Annual Meeting Abstracts, Blood* 2012, 120, 1657.

(15) Braun, T.; Coude, M.; Berrou, J.; Bertrand, S.; Riveiro, E.; Herait, P.; Baruchel, A.; Dombret, H.; Gardin, C.; Preclinical study of the bromodomain inhibitor OTX015 in acute myeloid (AML) and lymphoid (ALL) leukemias. *ASH Annual Meeting Abstracts, Blood* 2013, 122, 4218.

(16) Noel, J. K; Iwata, K.; Ooike, S.; Sugahara, K.; Nakamura, H.; Daibata, M. Development of the BET bromodomain inhibitor OTX015. *Mol. Cancer Ther.* 2013, 12, C244.

(17) Jahagirdar, R.; Zhang, H.; Azhar, S.; Tobin, J.; Attwell, S.; Yu, R.; Wu, J.; McLure, K. G.; Hansen, H. C.; Wagner, G. S.; Young, P. R.; Srivastava, R. A. K.; Wong, N. C. W.; Johansson, J. A novel BET bromodomain inhibitor, RVX-208, shows reduction of atherosclerosis in hyperlipidemic ApoE deficient mice. *Atherosclerosis* 2014, 236, 91-100.

(18) Bourgeas, R.; Basse, M.-J.; Morelli, X.; Roche, P. Atomic analysis of protein-protein interfaces with known inhibitors: the 2P2I database. *PLoS One* 2010, 5, e9598.

(19) Basse, M.-J.; Betzi, S.; Bourgeas, R.; Bouzidi, S.; Chetrit, B.; Hamon, V.; Morelli, X.; Roche, P. 2P2Idb: a structural database dedicated to orthosteric modulation of protein-protein interactions. *Nucleic Acids Res.* 2013, 41, D824-327. http://2p2idb.cnrs-mrs.fr

(20) Morelli, X.; Bourgeas, R.; Roche, P. Chemical and structural lessons from recent successes in protein-protein interaction inhibition (2P2I). *Curr. Opin. Chem. Biol.* 2011, 15, 475-481.

(21) Hamon, V; Bourgeas, R.; Ducrot, P.; Theret, I.; Xuereb, L.; Basse, M.-J.; Brunel, J.-M.; Combes, S.; Morelli, X.; Roche, P. 2P2I HUNTER: a tool for filtering orthosteric protein-protein interac interaction modulators via a dedicated support vector machine. *J. R. Soc. Interface* 2014, 11, 20130860.

(22) Hamon, V.; Brunel, J. M.; Combes, S.; Basse, J.-M.; Roche, P.; Morelli, X. 2P2Ichem: focused chemical libraries dedicated to orthosteric modulation of protein-protein interactions. *Med. Chem. Comm.* 2013, 4, 797-809.

(23) Zhang, X.; Betzi, S.; Morelli, X.; Roche, P. Focused chemical libraries—design and enrichment: an example of protein-protein interaction chemical space. *Future Med. Chem.* 2014, 6, 1291-1307.

(24) Filippakopoulos, P.; Qi, J.; Picaud, S.; Shen, Y.; Smith, W. B.; Fedorov, O.; Morse, E. M; Keates, T.; Hickman, T. T; Felletar, I.; Philpott, M.; Munro, S.; McKeown, M. R.; Wang, Y.; Christie, A. L.; West, N.; Cameron, M. J.; Schwartz, B.; Heightman, T. D.; La Thangue, N.; French, C. A.; Wiest, O.; Kung, A. L.; Knapp, S.; Bradner, J. E. Selective inhibition of BET bromodomains. *Nature* 2010, 468, 1067-1073.

(25) Vollmuth, F.; Blankenfeldt, W.; Geyer, M. Structures of the dual bromodomains of the P-TEFb-activating protein Brd4 at atomic resolution. *J. Biol. Chem.* 2009, 284, 36547-36556.

(26) Drouin, L.; McGrath, S.; Vidler, L. R.; Chaikuad, A.; Monteiro, O.; Tallant, C.; Philpott, M.; Rogers, C.; Fedorov, O.; Liu, M.; Akhtar, W.; Hayes, A.; Raynaud, F.; Müller, S.; Knapp, S.; Hoelder, S. Structure enabled design of BAZ2-ICR, a chemical probe targeting the bromodomains of BAZ2A and BAZ2B. *J. Med. Chem.* 2015, 58, 2553-2559.

(27) Bennett, J.; Fedorov, O.; Tallant, C.; Monteiro, O.; Meier, J.; Gamble, V., Savitsky, P.; Nunez-Alonso, G. A.; Haendler, B.; Rogers, C.; Brennan, P. E.; Müller, S.; Knapp, S. Discovery of a chemical tool inhibitor targeting the bromodomains of TRIM24 and BRPF. *J. Med. Chem.* 2015, DOI: 10.1021/acs.jmedchem.5b00458.

(28) Palmer, W. S.; Poncet-Montange, G.; Liu, G.; Petrocchi, A.; Reyna, N.; Subramanian, G.; Theroff, J.; Yau, A.; Kost-Alimova, M.; Bardenhagen, J. P.; Leo, E.; Shepard, H. E.; Tieu, T. N.; Shi, X.; Zhan, Y.; Zhao, S.; Barton, M. C.; Draetta, G.; Toniatti, C.; Jones, P.; Geck Do, M.; Andersen, J. N. Structure-guided design of IACS-9571, a selective high-affinity dual TRIM24-BRPF1 bromodomain inhibitor. *J. Med. Chem.* 2015, DOI: 10.1021/acs.jmedchem.5b00405.

(29) Vidal, A.; Giraud, I.; Madelmont, J.-C. Improved synthesis of 7-(alkyl/aryl)guanine. *Synthetic comm.* 2004, 34, 3359-3365.

(30) Kalla, R. V.; Elzein, E.; Perry, T.; Li, X.; Gimbel, A.; Yang, M.; Zeng, D.; Zablocki, J. Selective, high affinity A2B adenosine receptor antagonists: N-1 monosubstituted 8-(pyrazol-4-yl)xanthines. *Bioorg. Med. Chem. Lett.* 2008, 18, 1397-1401.

(31) Kuang, M.; Zhou, J.; Wang, L.; Liu, Z., Guo, J.; Wu, R. Binding Kinetics versus Affinities in BRD4 Inhibition. *J. Chem. Inf. Model.* 2015, 55, 1926-1935.

(32) Ran, T.; Zhang, Z.; Liu, K.; Lu, Y.; Li, H.; Xu, J.; Xiong, X.; Zhang, Y.; Xu, A.; Lu, S.; Liu, H.; Lu, T.; Chen, Y. Insight into the key interactions of bromodomain inhibitors based on molecular docking, interaction fingerprinting, molecular dynamics and binding free energy calculation. *Mol. Biosyst.* 2015, 11, 1295-1304.

(33) Laskowski, R. A.; Swindells, M. B. LigPlot+: multiple ligand-protein interaction diagrams for drug discovery. *J. Chem. Inf. Model.* 2011, 51, 2778-2786.

(34) Chem. Biol. 2015, 22 (6), 755-763. Hijacking the E3 Ubiquitin Ligase Cereblon to Efficiently Target BRD4. (PMID: 26051217).

(35) Angew. Chem. Int. Ed. Engl. 2015 doi: 10.1002/anie.201507634. [Epub ahead of print]. Modular PROTAC Design for the Degradation of Oncogenic BCR-ABL. (PMID: 26593377).

(36) Chem. Biol. 2015, 10 (8), 1831-1837. HaloPROTACS: Use of Small Molecule PROTACs to Induce Degradation of HaloTag Fusion Proteins. (PMID: 26070106)

Essentiellement les structures des PROTACs correspondraient au VHL ligand ou au Cereblon ligand dont les structures sont en PJ. Différents espaceurs Protac-molécules sont possibles.

The invention claimed is:

1. An inhibitor of a BET protein comprising a xanthine compound of formula (I)

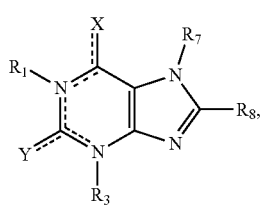

Formula (I)

wherein:

X represents an oxygen atom;

Y represents an oxygen atom, an amino group, or $NHR_o$;

wherein $R_o$ represents $-C(O)OR_p$ wherein $R_p$ represents a $C_1$-$C_4$ alkyl;

$R_1$ represents a hydrogen atom;

$R_3$ is selected from the group consisting of: ethyl, n-propyl, i-propyl, n-butyl, i-butyl, s-butyl, t-butyl, n-pentyl, n-hexyl, cyclopropyl, cyclobutyl, cyclopentyl and cyclohexyl or a benzyl optionally substituted by:

a halogen atom, or a $C_1$-$C_4$alkyl;

$R_7$ represents a $C_1$-$C_4$ alkyl;

$R_8$ represents $-SH$, $-CH_2-O-R_r$, or $-CH_2-S-R$, wherein $R_r$ represents one of the following groups optionally substituted by one or more $C_1$-$C_6$ alkyl, amino groups, halogen atoms, $(C_1$-$C_4)$alkanoic acid, $-S(O_2)-C_1$-$C_4)$alkyl, $-S(O_2)$-piperidine, $-S(O_2)-(N,N)$dimethylamine, $-S(O_2)$-morpholine, nitro groups, $-C(=O)-O-(C_1$-$C_4)$alkyl, $-S(O_2)-N(H)-(C_1$-$C_4)$alkyl, oxo-pyrazole optionally substituted by one or more $(C_1$-$C_4)$alkanoic acid, pyrazole optionally substituted by one or more $(C_1$-$C_4)$alkanoic acid or $(C_1$-$C_4)$ alkyl, phenyl, oxy-phenyl, pyrrolidine optionally substituted by one or more $(C_1$-$C_4)$alkanoic acid, thiazolidin optionally substituted by one or more $(C_1$-$C_4)$alkanoic acid, $-C(=O)-N(H)$-benzyl, $-N(H)$-quinazolinone, $-OH$, thiophenyl optionally substituted by one or more $(C_1$-$C_4)$alkanoic acid, methyl-tetrahydrofuran or $-CH_2$-pyrazole optionally substituted by one or more $(C_1$-$C_4)$ alkyl:

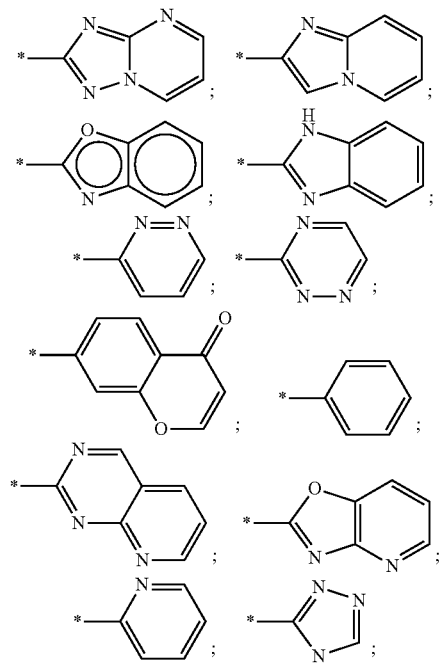

-continued

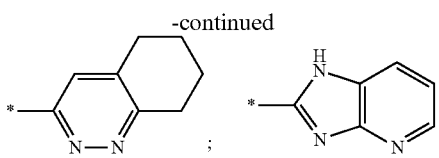

wherein * is the linking point to the sulfur atom or oxygen atom,
or a pharmaceutically acceptable salt thereof and/or tautomeric form thereof.

2. An inhibitor of a BET protein which is a xanthine compound of formula (I)

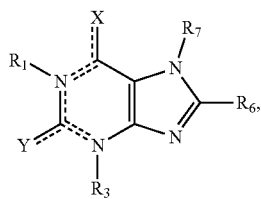

Formula (I)

wherein:
X represents an oxygen atom;
Y represents an oxygen atom, an amino group, or $NHR_o$;
 wherein $R_o$ represents —C(O)O$R_p$ wherein $R_p$ represents a $C_1$-$C_4$ alkyl;
$R_1$ represents a hydrogen atom;
$R_3$ is selected from the group consisting of: ethyl, n-propyl, i-propyl, n-butyl, i-butyl, s-butyl, t-butyl, n-pentyl, n-hexyl, cyclopropyl, cyclobutyl, cyclopentyl and cyclohexyl, or a benzyl, optionally substituted by:
a halogen atom, or
a $C_1$-$C_4$ alkyl;
$R_7$ represents a $C_1$-$C_4$ alkyl;
$R_8$ represents —CH$_2$—O—$R_s$ or —CH$_2$—S—$R_s$;
 wherein $R_s$ represents one of the following groups optionally substituted by one or more methyl, ethyl, butyl or amino groups, halogen atoms, ($C_1$-$C_4$)alkanoic acid, —S(O$_2$)—($C_1$-$C_4$)alkyl, —S(O$_2$)-piperidine, —S(O$_2$)—(N,N)dimethylamine, —S(O$_2$)-morpholine, nitro groups, —C(=O)—O—($C_1$-$C_4$) alkyl, —S(O$_2$)—N(H)—($C_1$-$C_4$)alkyl, oxo-pyrazole optionally substituted by one or more ($C_1$-$C_4$)alkanoic acid, pyrazole optionally substituted by one or more ($C_1$-$C_4$)alkanoic acid or ($C_1$-$C_4$)alkyl, thiazolidin optionally substituted by one or more ($C_1$-$C_4$)alkanoic acid, —C(=O)—N(H)-benzyl, —OH, thiophenyl optionally substituted by one or more ($C_1$-$C_4$)alkanoic acid, methyl-tetrahydrofuran or —CH$_2$-pyrazole optionally substituted by one or more ($C_1$-$C_4$) alkyl:

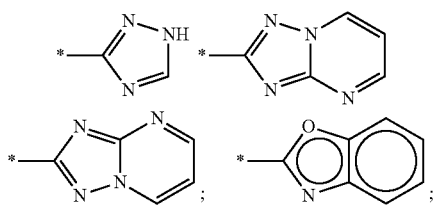

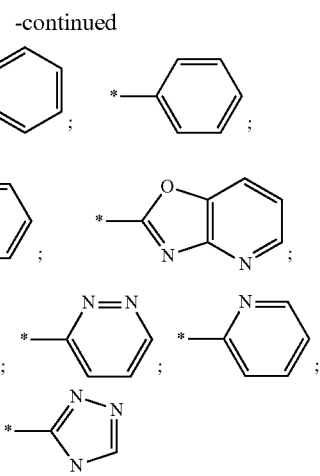

wherein * is the linking point to the sulfur atom or oxygen atom;
or a pharmaceutically acceptable salt thereof and/or tautomeric form thereof.

3. A pharmaceutical composition comprising as active principle, the inhibitor according to claim 1 and a pharmaceutically acceptable excipient.

4. A method for treating leukemia comprising administering to a mammal in need thereof a therapeutically effective amount of the inhibitor according to claim 1.

5. The inhibitor according to claim 1 wherein said inhibitor has an IC$_{50}$ for BRD4 (BD1) equal to or less than 50 µM.

6. The inhibitor according to claim 1 wherein said inhibitor has an IC$_{50}$ equal to or less than 20 µM for BRD4 (BD1).

7. The inhibitor according to claim 1 wherein said inhibitor has an IC$_{50}$ equal to or less than 10 µM for BRD4 (BD1).

8. A non-therapeutic method for inhibiting a bromodomain of a BET protein comprising contacting said bromodomain of a BET protein with the inhibitor according to claim 1, wherein said BET protein is selected from the group consisting of BRD2, BRD3, BRD4 and BRDT.

9. A non-therapeutic method for inhibiting the BRD4 protein, wherein said inhibitor binds to BD1 of BRD4, and wherein said inhibitor has an IC$_{50}$ for BRD4 (BD1) equal to or less than 50 µM, comprising contacting the inhibitor according to claim 1 with a BRD4 protein.

10. A non-therapeutic in vivo method for degrading a BET protein by using the inhibitor according claim 1 in the presence of cells which express the E3 ubiquitin ligase, wherein the inhibitor comprises either Y, $R_3$ or $R_8$ as a linker-ligand for the E3 ubiquitin ligase, said ligand being a cereblon ligand or a VHL ligand having the following formulas:

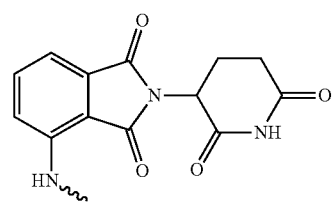

Cereblon ligand

-continued

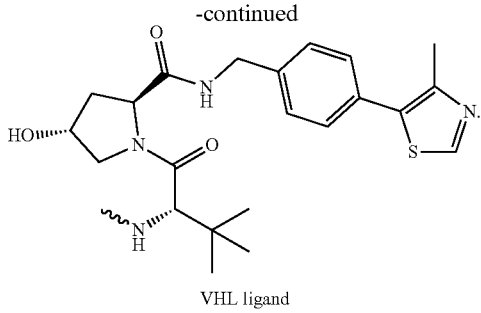

VHL ligand

11. A non-therapeutic method for inhibiting a bromodomain of a BET protein comprising contacting said bromodomain of a BET protein with the pharmaceutical composition according to claim 3, wherein the BET protein is selected from the group consisting of BRD2, BRD3, BRD4 and BRDT.

12. A pharmaceutical composition comprising as active principle, the inhibitor according to claim 2 and a pharmaceutically acceptable excipient.

13. A method for treating leukemia comprising administering to a mammal in need thereof a therapeutically effective amount of the inhibitor according to claim 2.

14. The inhibitor according to claim 2 wherein said inhibitor has an IC50 for BRD4 (BD1) equal to or less than 50 μM.

15. The inhibitor according to claim 2 wherein said inhibitor has an IC50 equal to or less than 20 μM for BRD4 (BD1).

16. The inhibitor according to claim 2 wherein said inhibitor has an IC50 equal to or less than 10 μM for BRD4 (BD1).

17. A non-therapeutic method for inhibiting a bromodomain of a BET protein comprising contacting said bromodomain of a BET protein with the inhibitor according to claim 2, wherein said BET protein is selected from the group consisting of BRD2, BRD3, BRD4 and BRDT.

18. A non-therapeutic method for inhibiting the BRD4 protein, wherein said inhibitor binds to BD1 of BRD4, and wherein said inhibitor has an $IC_{50}$ for BRD4 (BD1) equal to or less than 50 μM, comprising contacting the inhibitor according to claim 2 with a BRD4 protein.

* * * * *